US010329622B2

(12) United States Patent
McCann et al.

(10) Patent No.: US 10,329,622 B2
(45) Date of Patent: Jun. 25, 2019

(54) METHODS OF DETECTING BLADDER CANCER

(71) Applicant: Cepheid, Sunnyvale, CA (US)

(72) Inventors: Leena McCann, Santa Clara, CA (US); Stacey Ellen Wallace, Sunnyvale, CA (US); Edwin Wei-Lung Lai, Menlo Park, CA (US); Russell Higuchi, Alameda, CA (US)

(73) Assignee: Cepheid, Sunnyvale, CA (US)

( * ) Notice: Subject to any disclaimer, the term of this patent is extended or adjusted under 35 U.S.C. 154(b) by 0 days.

(21) Appl. No.: 14/199,292

(22) Filed: Mar. 6, 2014

(65) Prior Publication Data
US 2014/0309127 A1 Oct. 16, 2014

Related U.S. Application Data

(60) Provisional application No. 61/773,724, filed on Mar. 6, 2013.

(51) Int. Cl.
C12Q 1/6886 (2018.01)

(52) U.S. Cl.
CPC ..... *C12Q 1/6886* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,155,018 A | 10/1992 | Gillespie et al. | |
| 5,958,349 A | 9/1999 | Petersen et al. | |
| 6,403,037 B1 | 6/2002 | Chang et al. | |
| 6,440,725 B1 | 8/2002 | Pourahmadi et al. | |
| 6,783,736 B1 | 8/2004 | Taylor et al. | |
| 6,818,185 B1 | 11/2004 | Petersen et al. | |
| 7,351,538 B2 | 4/2008 | Fuchs et al. | |
| 7,402,422 B2 | 7/2008 | Fuchs et al. | |
| 8,114,588 B2 | 2/2012 | Yoshiki et al. | |
| 2004/0076955 A1* | 4/2004 | Mack | C07K 14/47 435/6.14 |
| 2010/0086932 A1 | 4/2010 | Asensio et al. | |

FOREIGN PATENT DOCUMENTS

| | | |
|---|---|---|
| EP | 2138848 A1 | 12/2009 |
| WO | 2013158972 A1 | 10/2013 |
| WO | 2014018926 A1 | 1/2014 |
| WO | 2014118334 A1 | 8/2014 |

OTHER PUBLICATIONS

Finch et al. (1999) Cloning of the Human Uroplakin 1B cDNA and Analysis of its Expression in Urothelial-Tumor Cell Lines and Bladder-Carcinoma Tissue. International Journal of Cancer, 80:533-538.*
Varga et al. (2004) Methylation of a CpG Island within the Uroplakin Ib Promoter: A Possible Mechanism for Loss of Uroplakin Ib Expression in Bladder Carcinoma. Neoplasia, 6(2):128-135.*
Whitehead et al. (2005) Variation in tissue-specific gene expression among natural populations. Genome Biology, 6:R13.*
Ginzinger, D. (2002) Gene quantification using real-time quantitative PCR: An emerging technology hits the mainstream. Experimental Hematology, 30:503-512.*
Elsamman et al. (2006) Differences in gene expression between noninvasive and invasive transitional cell carcinoma of the human bladder using complementary deoxyribonucleic acid microarray: Preliminary results. Urologic Oncology: Seminars and Original Investigations, 24:109-115.*
Sambrook et al. (2001) Molecular Cloning: A Laboratory Manual, 3rd Edition, Cold Spring Harbor Laboratory Press, New York, pp. 8.1-8.126.*
Affymetrix HG-U133 Plus 2.0 Annotation File (Accessed from: <http://www.affymetrix.com/Auth/analysis/downloads/na26/ivt/HG-U133_Plus_2.na26.annot.csv.zip> on Mar. 18, 2013, 1 page).*
Mengual et al. (2009) DNA Microarray Expression Profiling of Bladder Cancer Allows Identification of Noninvasive Diagnostic Markers. The Journal of Urology, 182:741-748.*
NM_006952 (*Homo Sapiens* uroplakin 1B (UPK1B) mRNA, NCBI Reference Sequence, GI:49619236, priority to Dec. 17, 2011, 5 pages).*
Aquino de Muro. "Probe Design, Production, and Applications", in: Walker et al., Medical Biomethods Handbook (New Jersey, Humana Press, 2005), pp. 13-23.*
National Cancer Institute "What You Need To Know About: Bladder Cancer" (NIH Publication No. 10-1559, published Aug. 2010).*
Affymetrix Human Gene ST 1.0 Array Annotation file excerpt Obtained from <http://www.affymetrix.com/Auth/analysis/downloads/na27/wtgene/HuGene-1_0-st-> on Dec. 30, 2016.*
Blalock et al. (2012) Gene Expression Analysis of Urine Sediment: Evaluation for Potential Noninvasive Markers of Interstitial Cystitis/Bladder Pain Syndrome. The Journal of Urology, 187:725-732.*
Rosser et al. (2009) Bladder Cancer-Associated Gene Expression Signatures Identified by Profiling of Exfoliated Urothelia. Cancer Epidemiology, Biomarkers, & Prevention, 18(2):444-453.*
Affymetrix Expression Probeset Details for HG-U133A:210064_S_AT (accessed from: https://www.affymetrix.com/analysis/netaffx/fullrecord.affx?pk=HG-U133A:210064_S_AT, accessed on: Jun. 27, 2017, 4 pages).*
Brabender J, et al. The molecular signature of normal squamous esophageal epithelium identifies the presence of a field effect and can discriminate between patients with Barrett's esophagus and patients with Barrett's-associated adenocarcinoma. Cancer Epidemiol Biomarkers Prev. 14:2113-2117. 2005.
Buchumensky V, et al. Cytokeratin 20: a new marker for early detection of bladder cell carcinoma. J Urol. 160(6 Pt 1):1971-4. 1998.

(Continued)

*Primary Examiner* — Neil P Hammell
(74) *Attorney, Agent, or Firm* — McNeill Baur PLLC

(57) ABSTRACT

Compositions and methods for detecting bladder cancer are provided. In some embodiments, methods of detecting low grade bladder cancer are provided. In some embodiments, methods of monitoring recurrence of bladder cancer are provided. In some embodiments, the methods comprise detecting androgen receptor (AR) and/or uroplakin 1B (UPK1B).

29 Claims, No Drawings
Specification includes a Sequence Listing.

(56) References Cited

OTHER PUBLICATIONS

Christoph F, et al. Urinary cytokeratin 20 mRNA expression has the potential to predict recurrence in superficial transitional cell carcinoma of the bladder. Cancer Lett. 245(1-2):121-6. 2007 (Epub 2006).

Damrauer JS, et al. Intrinsic subtypes of high-grade bladder cancer reflect the hallmarks of breast cancer biology. PNAS. 111:3110-3115. 2014.

Degraff DJ, et al. Loss of the urothelial differentiation marker FOXA1 is associated with high grade, late stage bladder cancer and increased tumor proliferation. PLoS One. 7(5):e36669. 2012.

Eissa S, et al. Comparison of CD44 and cytokeratin 20 mRNA in voided urine samples as diagnostic tools for bladder cancer. Clin Biochem. 41(16-17):1335-41. 2008.

Eissa S, et al. Comparison of cytokeratin 20 RNA and angiogenin in voided urine samples as diagnostic tools for bladder carcinoma. Clin Biochem. 37(9):803-10. 2004.

Eissa S, et al. The clinical relevance of urine-based markers for diagnosis of bladder cancer. Med Oncol. 28(2):513-8. 2011.

Elsamman E, et al. Differences in gene expression between noninvasive and invasive transitional cell carcinoma of the human bladder using complementary deoxyribonucleic acid microarray: preliminary results. Urol Oncol. 24(2):109-15. 2006.

Gallagher EM, et al. Recurrence of urothelial carcinoma of the bladder: a role for insulin-like growth factor-II loss of imprinting and cytoplasmic E-cadherin immunolocalization. Clin Cancer Res. 14(21):6829-38. 2008.

GenBank Accession No. NM_000044, 11 pages. 2014.
GenBank Accession No. NM_000756, 4 pages. 2014.
GenBank Accession No. NM_001011645, 7 pages. 2014.
GenBank Accession No. NM_006952, 4 pages. 2014.
GenBank Accession No. NM_007193, 4 pages. 2014.
GenBank Accession No. NM_007313, 7 pages. 2014.
GenBank Accession No. NM_019010, 5 pages. 2014.

Guo B, et al. Quantitative detection of cytokeratin 20 mRNA in urine samples as diagnostic tools for bladder cancer by real-time PCR. Exp Oncol. 31(1):43-7. 2009.

International Search Report and Written Opinion for of the International Searching Authority PCT/US2014/021199, dated Jun. 10, 2014, 20 pages.

International Search Report and Written Opinion of the International Searching Authority for PCT/US2013/037334, dated Jun. 19, 2013, 13 pages.

Ishii Y, et al. Bladder cancer discovered by ovarian metastasis: cytokeratin expression is useful when making differential diagnosis. Int J Urol. 12(1):104-7. 2005.

Izquierdo L, et al. Molecular characterization of upper urinary tract tumours. BJU Int. 106(6):868-72. 2010 (Epub 2009).

Jiang J, et al. Cytokeratin 7 and cytokeratin 20 in primary urinary bladder carcinoma and matched lymph node metastasis. Arch Pathol Lab Med. 125(7):921-3. 2001.

Kawahito Y, et al. Corticotropin releasing hormone in colonic mucosa in patients with ulcerative colitis. Gut. 37(4):544-51. 1995.

Kim J, et al. Reduced expression and homozygous deletion of annexin A10 in gastric carcinoma. Int J Cancer. 125(8):1842-50. 2009.

Kim JK, et al. Decreased expression of annexin A10 in gastric cancer and its overexpression in tumor cell growth suppression. Oncol Rep. 24(3):607-12. 2010.

Langner C, et al. Prognostic value of keratin subtyping in transitional cell carcinoma of the upper urinary tract. Virchows Arch. 445(5):442-8. 2004.

Lassmann S, et al. Identification of occult tumor cells in node negative lymph nodes of colorectal cancer patients by cytokeratin 20 gene and protein expression. Int J Colorectal Dis. 19(2):87-94. 2004 (Epub 2003).

Lee LG, et al. Seven-Color, Homogeneous Detection of Six PCR Products. BioTechniques. 27:342-349. 1999.

Liu DW, Choice of endogenous control for gene expression in nonsmall cell lung cancer. European Respiratory Journal. 26:1002-1008. 2005.

Liu SH, et al. Down-regulation of annexin A10 in hepatocellular carcinoma is associated with vascular invasion, early recurrence, and poor prognosis in synergy with p53 mutation. Am J Pathol. 160(5):1831-7. 2002.

Lobban et al. Uroplakin Gene Expression by Normal and Neoplastic Human Urothelium. Am J Pathol. 153:1957-1967. 1998.

Lopez-Beltran A, et al. Invasive micropapillary urothelial carcinoma of the bladder. Hum Pathol. 41(8):1159-64. 2010.

Lu J, et al. MicroRNA expression profiles classify human cancers. Nature. 435:834-838. 2005.

Lu SH, et al. Expression and prognostic significance of gastric-specific annexin A10 in diffuse- and intestinal-type gastric carcinoma. J Gastroenterol Hepatol. 26(1):90-7. 2011.

Marin-Aguilera M, et al. Utility of urothelial mRNA markers in blood for staging and monitoring bladder cancer. Urology. 79(1):240. e9-15. 2012 (Epub 2011).

Mengual L, et al. Gene expression signature in urine for diagnosing and assessing aggressiveness of bladder urothelial carcinoma. Clin Cancer Res. 16(9):2624-33. 2010.

Mengual L, et al. Partially degraded RNA from bladder washing is a suitable sample for studying gene expression profiles in bladder cancer. Eur Urol. 50(6):1347-55; Editorial Comment 1355-6. 2006.

Minas V, et al. Intratumoral CRH modulates immuno-escape of ovarian cancer cells through FasL regulation. Br J Cancer. 97(5):637-45. 2007.

Miyamoto H, et al. GATA binding protein 3 is down-regulated in bladder cancer yet strong expression is an independent predictor of poor prognosis in invasive tumor. Human Pathology. 43:2033-2040. 2012.

Moon HS, et al. Benzyldihydroxyoctenone, a novel anticancer agent, induces apoptosis via mitochondrial-mediated pathway in androgen-sensitive LNCaP prostate cancer cells. Bioorganic & Medicinal Chemistry Letters. 19:742-744. 2009.

Munksgaard PP, et al. Low ANXA10 expression is associated with disease aggressiveness in bladder cancer. Br J Cancer. 105(9):1379-87. 2011.

Olsburgh J, et al. Uroplakin gene expression in normal human tissues and locally advanced bladder cancer. J Pathol. 199:41-49. 2003.

Ozdemir NO, et al. IMP3 expression in urothelial carcinomas of the urinary bladder. Turk Patoloji Derg. 27(1):31-7. 2011.

Pignot G, et al. Hedgehog pathway activation in human transitional cell carcinoma of the bladder. Br J Cancer. 106(6):1177-86. 2012.

Plesea IA, et al. Detection and morphological profile of early stages bladder carcinoma: preliminary study. Virhows Arch. 459(Suppl 1):S296. 2011.

Pu XY, et al. The value of combined use of survivin, cytokeratin 20 and mucin 7 mRNA for bladder cancer detection in voided urine. J Cancer Res Clin Oncol. 134(6):659-65. 2008 (Epub 2007).

Qian J, et al. Characteristics of hepatic igf-ii expression and monitored levels of circulating igf-ii mRNA in metastasis of hepatocellular carcinoma. Am J Clin Pathol. 134(5):799-806. 2010.

Raica M, et al. Cytokeratin 20, 34betaE12 and overexpression of HER-2/neu in urine cytology as predictors of recurrences in superficial urothelial carcinoma. Rom J Morphol Embryol. 46(1):11-5. 2005.

Retz M, et al. Mucin 7 and cytokeratin 20 as new diagnostic urinary markers for bladder tumor. J Urol. 169(1):86-9. 2003.

Ribal MJ, et al. Molecular staging of bladder cancer with RT-PCR assay for CK20 in peripheral blood, bone marrow and lymph nodes: comparison with standard histological staging. Anticancer Res. 26(1A):411-9. 2006.

Sanchez-Carbayo M, et al. Gene discovery in bladder cancer progression using cDNA microarrays. Am J Pathol. 163(2):505-16. 2003.

Shulman et al. Evaluation of Four Different Systems for Extraction of RNA from Stool Suspensions Using MS-2 Coliphage as an Exogenous Control for RT-PCR Inhibition. PLoS One. 7(7):e39455. 2012.

(56) References Cited

OTHER PUBLICATIONS

Siracusano S, et al. The simultaneous use of telomerase, cytokeratin 20 and CD4 for bladder cancer detection in urine. Eur Urol. 47(3):327-33. 2005 (Epub 2004).

Soong R, et al. Quantitative reverse transcription-polymerase chain reaction detection of cytokeratin 20 in noncolorectal lymph nodes. Clin Cancer Res. 7(11):3423-9. 2001.

Varallyay et al. MicroRNA detection by northern blotting using locked nucleic acid probes. Nature Protocols. 3:190-196. 2008.

Varga AE, et al. Methylation of a CpG Island with the Uroplakin Ib promoter: A possible mechanism for loss of uroplakin Ib expression in bladder carcinoma. Neoplasia. 6(2): 128-135. 2004.

Walkerpeach et al. Ribonuclease-resistant RNA controls (Armored RNA) for reverse transcription-PCR, branched DNA, and genotyping assays for hepatitis C virus. Clin Chem. 45:2079-2085. 1999.

Watson JA, et al. Urinary insulin-like growth factor 2 identifies the presence of urothelial carcinoma of the bladder. BJU Int. 103(5):694-7. 2009 (Epub 2008).

Weber T, et al. Detection of disseminated medullary thyroid carcinoma cells in cervical lymph nodes by cytokeratin 20 reverse transcription-polymerase chain reaction. World J Surg. 26(2):148-52. 2002 (Epub 2001).

Wilkinson. A rapid and convenient method for isolation of nuclear, cytoplasmic and total cellular RNA. Nucleic Acids Res. 6:10934. 1988.

Wilkinson. RNA isolation: a mini-prep method. Nucleic Acids Res. 16:10933. 1988.

Williams E, et al. Androgen receptor expression in genitourinary neoplasms. Modern Pathology. 26(52):258A Feb. 2013, and 102nd Annual Meeting of the United States and Canadian Academy of Pathology (USCAP); Baltimore MD, USA, 2013.

Wu X, et al. Uroplakin II as a promising marker for molecular diagnosis of nodal metastases from bladder cancer: comparison with cytokeratin 20. J Urol. 174(6):2138-42, Editorial Comment 2142-3. 2005.

Ye YK, et al. CK20 and Ki-67 as significant prognostic factors in human bladder carcinoma. Clin Exp Med. 10(3):153-8. 2010.

Zheng Y, et al. Dihydrotestosterone upregulates the expression of epidermal growth factor receptor and ERBB2 in androgen receptor-positive bladder cancer cells. Endocrine Related Cancer. 18:451-464. 2011.

D'Sullivan et al., "A Multigene Urine Test for the Detection and Stratification of Bladder Cancer in Patients Presenting with Hematuria," The Journal of Urology, vol. 188, pp. 741-747 (Sep. 2012).

Lobban et al., "Uroplakin Gene Expression by Normal and Neoplastic Human Urothelium," American Journal of Pathology, vol. 153, No. 6, pp. 1957-1967(Dec. 1998).

Olsburgh et al., "Uroplakin gene expression in normal human tissues and locally advanced bladder cancer." Journal of Pathology, 199:41-49 (2003).

Wallace et al., "Development of a 90-Minute Integrated Noninvasive Urinary Assay for Bladder Cancer Detection," The Journal of Urology, vol. 199, Issue 3, pp. 655-662, Mar. 2018.

Affymetrix Package Insert, GeneChip® Human Gene 1.0 ST Array, downloaded on Apr. 3, 2018, at http://tools.thermofisher.com/content/sfs/manuals/hugene_1_0_st_insert.pdf.

\* cited by examiner

METHODS OF DETECTING BLADDER CANCER

1. FIELD OF THE INVENTION

Compositions and methods for detecting bladder cancer are provided. In particular, bladder cancer markers and panels of markers useful in the detection of bladder cancer are provided.

2. BACKGROUND 386,000 cases of bladder cancer are diagnosed globally each year, including 70,500 cases per year in the United States. The incidence of bladder cancer is three times higher in men than in women. The highest incidence and prevalence are found in the European Union, North America, North Africa, and the Middle East Smoking is the greatest risk factor for bladder cancer. Additional risk factors include chemical exposure, chemotherapy (such as Cytoxan), radiation treatment, and chronic bladder infection.

Bladder tumors include papillary tumors, which are urothelial carcinomas that grow narrow, finger-like projections; and nonpapillary (sessile) tumors, such as carcinoma-in-situ, which are less common but have a high risk of becoming invasive.

Symptoms of bladder cancer can include abdominal pain, blood in the urine, bone pain or tenderness, fatigue, painful urination, frequent urination, urinary urgency, incontinence, and weight loss. Diagnosis is generally based on imaging, urinalysis, and/or biopsy.

The prognosis for bladder cancer depends on the stage of cancer at diagnosis. The prognosis for early tumors is favorable, while the prognosis for advanced tumors is poor. Long-term follow up is recommended to detect cancer recurrence, which occurs in up to 70% of bladder cancers. For the first two years, cystoscopy and urine cytology are recommended every 3 to 4 months, and then at longer intervals in subsequent years, often for the patient's lifetime. These methods are invasive and costly, making bladder cancer one of the most expensive cancers to treat from diagnosis until death.

Existing non-invasive diagnostic tests include Immuno-Cyt™ (Scimedx, Denville, N.J.) and UroVysion® (Abbott Molecular, Abbott Park, Ill.) ImmunoCyt™ is a cytology assay that uses a cocktail of three monoclonal antibodies labeled with fluorescent markers to detect certain cellular markers of bladder cancer in exfoliated cells isolated from urine samples ImmunoCyt™ is used in conjunction with standard urine cytology to improve cytology's sensitivity at detecting tumor cells. UroVysion® is also a cytology-based assay, which detects aneupoloidy in certain chromosomes via fluorescent in situ hybridization (FISH). Determination of the results is conducted by enumerating signals through microscopic examination of the nucleus of cells in urine.

Improved methods for early detection of bladder cancer are needed. In particular, an accurate urine-based diagnostic test that does not rely on cytology could reduce the need for costly and invasive cystoscopy and labor-intensive and potentially subjective cytology assays.

3. SUMMARY

Compositions and methods for detecting bladder cancer are provided. In particular, bladder cancer markers and panels of markers useful in the detection of bladder cancer are provided. In some embodiments, the levels of androgen receptor (AR) and/or uroplakin 1B (UPK1B) mRNA, and optionally, at least one mRNA selected from CRH, IGF2, KRT20 and ANXA10 mRNA, are measured, for example, by quantitative RT-PCR, and the results can be used to determine whether or not a subject has bladder cancer. In some embodiments, the levels of AR and/or UPK1B mRNA, and optionally at least one mRNA selected from CRH, IGF2, KRT20 and ANXA10, are normalized to an endogenous control. In some embodiments, the endogenous control is ABL mRNA. In some embodiments, an endogenous control is selected that is expected to be expressed at similar levels in bladder urothelial cells from subjects with and without bladder cancer. In some embodiments, the sample is a urine sample. In some embodiments, the present methods are used to monitor subjects with a history of bladder cancer for tumor recurrence. In some embodiments, the subject has been treated with Bacillus Calmette-Guerin (BCG) within the past three months. In some embodiments, the present methods are used to detect bladder cancer in subjects with no history of bladder cancer. In some such embodiments, the subjects have symptoms of bladder cancer. Nonlimiting exemplary symptoms of bladder cancer include abdominal pain, blood in the urine, bone pain or tenderness, fatigue, painful urination, frequent urination, urinary urgency, incontinence, and weight loss. In some embodiments, the bladder cancer is low grade bladder cancer.

In some embodiments, methods for detecting the presence of bladder cancer in a subject are provided. In some embodiments, a method comprises detecting the levels of each marker of a set of bladder cancer markers in a sample from the subject, wherein the set of bladder cancer markers comprises androgen receptor (AR) or uroplakin 1B (UPK1B), or both AR and UPK1B. In some embodiments, detection of an elevated level of AR and/or UPK1B indicates the presence of bladder cancer in the subject.

In some embodiments, methods of monitoring anti-androgen therapy in a subject with bladder cancer are provided. In some embodiments, the methods comprise detecting the levels of each marker of a set of bladder cancer markers in a sample from the subject at a first time point, wherein the set of bladder cancer markers comprises androgen receptor (AR), or uroplakin 1B (UPK1B), or both AR and UPK1B. In some embodiments, a decrease in the level of the at least one marker at the first time point relative to a second time point indicates that the subject is responding to anti-androgen therapy. In some embodiments, the methods comprise comparing the level of the at least one marker at the first time point to the level of the at least one marker at the second time point. In some embodiments, the subject is undergoing anti-androgen therapy at the first time point. In some embodiments, the second time point is prior to the subject beginning anti-androgen therapy. In some embodiments, the subject is undergoing anti-androgen therapy at the second time point.

In some embodiments, the set of bladder cancer markers further comprises at least one marker selected from corticotrophin releasing hormone (CRH), insulin-like growth factor 2 (IGF2), keratin 20 (KRT20) and annexin 10 (ANXA10). In some embodiments, the set of bladder cancer markers comprises: a) AR, CRH, IGF1, KRT20, and ANXA10; b) AR, CRH, IGF1, and KRT20; c) UPK1B, CRH, IGF1, KRT20, and ANXA10; d) UPK1B, CRH, IGF1, and KRT20; e) AR, UPK1B, CRH, IGF1, KRT20, and ANXA10; or d) AR, UPK1B, CRH, IGF1, and KRT20.

In some embodiments, a method further comprises detecting an endogenous control. In some embodiments, the endogenous control is selected from ABL, GUSB, GAPDH, TUBB, and UPK1a. In some embodiments, the endogenous control is ABL. In some embodiments, a method comprises detecting an exogenous control. In some embodiments, the exogenous control is an RNA. In some such embodiments, the exogenous control is an Armored RNA®.

In some embodiments, detecting comprises RT-PCR. In some embodiments, detecting comprises quantitative RT-PCR. In some embodiments, a method comprises comparing a Ct value or a ΔCt value to a threshold Ct value or ΔCt value. In some embodiments, ΔCt is the Ct value for the endogenous control minus the Ct value for the marker. In some embodiments, the RT-PCR reaction takes less than three hours or less than 2 hours from an initial denaturation step through a final extension step.

In some embodiments, a method comprises contacting RNA from the sample with a set of bladder cancer marker primer pairs, wherein the set of bladder cancer marker primer pairs comprises a first primer pair for detecting AR, or a first primer pair for detecting UPK1B, or a first primer pair for detecting AR and a second primer pair for detecting UPK1B. In some embodiments, the set of bladder cancer marker primer pairs comprises a third primer pair for detecting a marker selected from CRH, IGF1, KRT20, and ANXA10. In some embodiments, the set of bladder cancer marker primer pairs comprises a fourth primer pair for detecting a marker selected from CRH, IGF1, KRT20, and ANXA10, wherein the third primer pair and the fourth primer pair detect different markers. In some embodiments, the set of bladder cancer marker primer pairs comprises a fifth primer pair for detecting a marker selected from CRH, IGF1, KRT20, and ANXA10, wherein the third primer pair, the fourth primer pair, and the fifth primer pair detect different markers. In some embodiments, wherein each bladder cancer marker primer pair produces an amplicon that is 50 to 500 nucleotides long, 50 to 400 nucleotides long, 50 to 300 nucleotides long, 50 to 200 nucleotides long, or 50 to 150 nucleotides long. In some embodiments, at least one, at least two, or at least three bladder cancer marker primer pair spans an intron in the genomic sequence. In some embodiments, each bladder cancer marker primer pair spans an intron in the genomic sequence.

In some embodiments, the primer pair for detecting AR comprises a first primer comprising at least 8, at least 9, at least 10, at least 11, at least 12, at least 13, at least 14, or at least 15, at least 16, at least 17, or at least 18 nucleotides of SEQ ID NO: 54 and a second primer comprising at least 8, at least 9, at least 10, at least 11, at least 12, at least 13, at least 14, or at least 15, at least 16, at least 17, or at least 18 nucleotides of SEQ ID NO: 55, wherein each primer is less than 50, less than 45, less than 40, less than 35, or less than 30 nucleotides long. In some embodiments, the primer pair for detecting UPK1B comprises a first primer comprising at least 8, at least 9, at least 10, at least 11, at least 12, at least 13, at least 14, or at least 15, at least 16, at least 17, or at least 18 nucleotides of SEQ ID NO: 51 and a second primer comprising at least 8, at least 9, at least 10, at least 11, at least 12, at least 13, at least 14, or at least 15, at least 16, at least 17, or at least 18 nucleotides of SEQ ID NO: 52, wherein each primer is less than 50, less than 45, less than 40, less than 35, or less than 30 nucleotides long.

In some embodiments, a method further comprises contacting RNA from the sample with an endogenous control primer pair. In some such embodiments, the endogenous control primer pair is for detecting an endogenous control is selected from ABL, GUSB, GAPDH, TUBB, and UPK1a. In some embodiments, the endogenous control primer pair is for detecting ABL. In some embodiments, the endogenous control primer pair comprises a first primer comprising SEQ ID NO: 8 and a second primer comprising SEQ ID NO: 9, wherein each primer is less than 50, less than 45, less than 40, less than 35, or less than 30 nucleotides long. In some embodiments, the endogenous control primer pair comprises a first primer comprising SEQ ID NO: 41 and a second primer comprising SEQ ID NO: 42, wherein each primer is less than 50, less than 45, less than 40, less than 35, or less than 30 nucleotides long. In some embodiments, the endogenous control primer pair comprises a first primer comprising at least 8, at least 9, at least 10, at least 11, at least 12, at least 13, at least 14, or at least 15, at least 16, at least 17, or at least 18 nucleotides of SEQ ID NO: 8 and a second primer comprising at least 8, at least 9, at least 10, at least 11, at least 12, at least 13, at least 14, or at least 15, at least 16, at least 17, or at least 18 nucleotides of SEQ ID NO: 9, wherein each primer is less than 50, less than 45, less than 40, less than 35, or less than 30 nucleotides long. In some embodiments, the endogenous control primer pair comprises a first primer comprising at least 8, at least 9, at least 10, at least 11, at least 12, at least 13, at least 14, or at least 15, at least 16, at least 17, or at least 18 nucleotides of SEQ ID NO: 41 and a second primer comprising at least 8, at least 9, at least 10, at least 11, at least 12, at least 13, at least 14, or at least 15, at least 16, at least 17, or at least 18 nucleotides of SEQ ID NO: 42, wherein each primer is less than 50, less than 45, less than 40, less than 35, or less than 30 nucleotides long.

In some embodiments, a method comprises contacting RNA from the sample with an exogenous control primer pair. In some such embodiments, the exogenous control primer pair is for detecting an exogenous RNA. In some embodiments, the exogenous control primer pair comprises a first primer comprising SEQ ID NO: 23 and a second primer comprising SEQ ID NO: 24, wherein each primer is less than 50, less than 45, less than 40, less than 35, or less than 30 nucleotides long. In some embodiments, the exogenous control primer pair comprises a first primer comprising SEQ ID NO: 44 and a second primer comprising SEQ ID NO: 45, wherein each primer is less than 50, less than 45, less than 40, less than 35, or less than 30 nucleotides long. In some embodiments, the exogenous control primer pair comprises a first primer comprising at least 8, at least 9, at least 10, at least 11, at least 12, at least 13, at least 14, or at least 15, at least 16, at least 17, or at least 18 nucleotides of SEQ ID NO: 23 and a second primer comprising at least 8, at least 9, at least 10, at least 11, at least 12, at least 13, at least 14, or at least 15, at least 16, at least 17, or at least 18 nucleotides of SEQ ID NO: 24, wherein each primer is less than 50, less than 45, less than 40, less than 35, or less than 30 nucleotides long. In some embodiments, the exogenous control primer pair comprises a first primer comprising at least 8, at least 9, at least 10, at least 11, at least 12, at least 13, at least 14, or at least 15, at least 16, at least 17, or at least 18 nucleotides of SEQ ID NO: 44 and a second primer comprising at least 8, at least 9, at least 10, at least 11, at least 12, at least 13, at least 14, or at least 15, at least 16, at least 17, or at least 18 nucleotides of SEQ ID NO: 45, wherein each primer is less than 50, less than 45, less than 40, less than 35, or less than 30 nucleotides long.

In some embodiments, the method comprises forming a set of bladder cancer marker amplicons, wherein the set of bladder cancer marker amplicons comprises an AR amplicon, or a UPK1B amplicon, or both an AR amplicon and a UPK1B amplicon, and contacting the bladder cancer marker amplicons with a set of bladder cancer marker probes, wherein the set of bladder cancer marker probes comprises a first probe for detecting the AR amplicon, or a first probe for detecting the UPK1B amplicon, or a first probe for detecting the AR amplicon and a second probe for detecting the UPK1B amplicon. In some embodiments, the set of bladder cancer marker amplicons comprises a third amplicon selected from a CRH amplicon, a IGF1 amplicon, a KRT20 amplicon, and a ANXA10 amplicon, and wherein the set of bladder cancer marker probes comprises a third probe for detecting the third amplicon. In some embodiments, the set of bladder cancer marker amplicons comprises a fourth amplicon selected from a CRH amplicon, a IGF1 amplicon, a KRT20 amplicon, and a ANXA10 amplicon, wherein the set of bladder cancer marker probes comprises a fourth probe for detecting the fourth amplicon, and wherein the third amplicon and the fourth amplicon are different. In some embodiments, the set of bladder cancer marker amplicons comprises a fifth amplicon selected from a CRH amplicon, a IGF1 amplicon, a KRT20 amplicon, and a ANXA10 amplicon, wherein the set of bladder cancer marker probes comprises a fifth probe for detecting the fifth amplicon, and wherein the third amplicon, the fourth amplicon, and the fifth amplicon are different.

In some embodiments, the probe for detecting AR comprises at least 8, at least 9, at least 10, at least 11, at least 12, at least 13, at least 14, or at least 15, at least 16, at least 17, or at least 18 nucleotides of SEQ ID NO: 56, wherein the probe is less than 50, less than 45, less than 40, less than 35, or less than 30 nucleotides long. In some embodiments, the probe for detecting UPK1B comprises at least 8, at least 9, at least 10, at least 11, at least 12, at least 13, at least 14, or at least 15, at least 16, at least 17, or at least 18 nucleotides of SEQ ID NO: 53, wherein the probe is less than 50, less than 45, less than 40, less than 35, or less than 30 nucleotides long. In some embodiments, each bladder cancer marker probe comprises a dye, and wherein each dye is detectably different from the other three labels. In some embodiments, each bladder cancer marker probe comprises a fluorescent dye and a quencher molecule.

In some embodiments, a method comprises forming an endogenous control amplicon, and contacting the endogenous control amplicon with an endogenous control probe. In some embodiments, the endogenous control probe comprises at least 8, at least 9, at least 10, at least 11, at least 12, at least 13, at least 14, or at least 15, at least 16, at least 17, or at least 18 nucleotides of SEQ ID NO: 10, 11, 12, or 43, wherein the endogenous control probe is less than 50, less than 45, less than 40, less than 35, or less than 30 nucleotides long. In some embodiments, the endogenous control probe comprises a dye that is detectably different from the dyes of the bladder cancer marker probes.

In some embodiments, a method comprises forming an exogenous control amplicon, and contacting the exogenous control amplicon with an exogenous control probe. In some embodiments, the exogenous control probe comprises at least 8, at least 9, at least 10, at least 11, at least 12, at least 13, at least 14, or at least 15, at least 16, at least 17, or at least 18 nucleotides of SEQ ID NO: 25 or 46, wherein the exogenous control probe is less than 50, less than 45, less than 40, less than 35, or less than 30 nucleotides long. In some embodiments, the exogenous control probe comprises a dye that is detectably different from the dyes of the bladder cancer marker probes and the endogenous control probe.

In some embodiments, the set of bladder cancer markers are detected in a single multiplex reaction.

In some embodiments, the sample comprises urothelial cells. In some embodiments, the sample is selected from a urine sample and a bladder washing sample. In some embodiments, the subject has a history of bladder cancer. In some embodiments, the subject is being monitored for recurrence of bladder cancer.

In some embodiments, compositions are provided. In some embodiments, a composition comprises a set of bladder cancer marker primer pairs, wherein the set of bladder cancer marker primer pairs comprises a first primer pair for detecting AR, or a first primer pair for detecting UPK1B, or a first primer pair for detecting AR and a second primer pair for detecting UPK1B. In some embodiments, the set of bladder cancer marker primer pairs comprises a third primer pair for detecting a marker selected from CRH, IGF1, KRT20, and ANXA10. In some embodiments, the set of bladder cancer marker primer pairs comprises a fourth primer pair for detecting a marker selected from CRH, IGF1, KRT20, and ANXA10, wherein the third primer pair and the fourth primer pair detect different markers. In some embodiments, the set of bladder cancer marker primer pairs comprises a fifth primer pair for detecting a marker selected from CRH, IGF1, KRT20, and ANXA10, wherein the third primer pair, the fourth primer pair, and the fifth primer pair detect different markers.

In some embodiments, each bladder cancer marker primer pair produces an amplicon that is 50 to 500 nucleotides long, 50 to 400 nucleotides long, 50 to 300 nucleotides long, 50 to 200 nucleotides long, or 50 to 150 nucleotides long. In some embodiments, at least one, at least two, or at least three bladder cancer marker primer pair spans an intron in the genomic sequence. In some embodiments, each bladder cancer marker primer pair spans an intron in the genomic sequence.

In some embodiments, the primer pair for detecting AR comprises a first primer comprising at least 8, at least 9, at least 10, at least 11, at least 12, at least 13, at least 14, or at least 15, at least 16, at least 17, or at least 18 nucleotides of SEQ ID NO: 54 and a second primer comprising at least 8, at least 9, at least 10, at least 11, at least 12, at least 13, at least 14, or at least 15, at least 16, at least 17, or at least 18 nucleotides of SEQ ID NO: 55, wherein each primer is less than 50, less than 45, less than 40, less than 35, or less than 30 nucleotides long. In some embodiments, the primer pair for detecting UPK1B comprises a first primer comprising at least 8, at least 9, at least 10, at least 11, at least 12, at least 13, at least 14, or at least 15, at least 16, at least 17, or at least 18 nucleotides of SEQ ID NO: 51 and a second primer comprising at least 8, at least 9, at least 10, at least 11, at least 12, at least 13, at least 14, or at least 15, at least 16, at least 17, or at least 18 nucleotides of SEQ ID NO: 52, wherein each primer is less than 50, less than 45, less than 40, less than 35, or less than 30 nucleotides long.

In some embodiments, a composition further comprises a set of bladder cancer marker probes, wherein the set of bladder cancer marker probes comprises a first probe for detecting an AR amplicon, or a first probe for detecting a UPK1B amplicon, or a first probe for detecting an AR amplicon and a second probe for detecting a UPK1B amplicon. In some embodiments, the set of bladder cancer marker probes comprises a third probe for detecting a third amplicon selected from a CRH amplicon, a IGF1 amplicon, a KRT20 amplicon, and a ANXA10 amplicon. In some embodiments, the set of bladder cancer marker probes comprises a fourth probe for detecting a fourth amplicon selected from a CRH amplicon, a IGF1 amplicon, a KRT20 amplicon, and a ANXA10 amplicon, wherein the third amplicon and the fourth amplicon are different. In some embodiments, the set of bladder cancer marker probes comprises fourth probe for detecting a fifth amplicon selected from a CRH amplicon, a IGF1 amplicon, a KRT20 amplicon, and a ANXA10 amplicon, wherein the third amplicon, the fourth amplicon, and the fifth amplicon are different.

In some embodiments, the probe for detecting AR comprises at least 8, at least 9, at least 10, at least 11, at least 12, at least 13, at least 14, or at least 15, at least 16, at least 17, or at least 18 nucleotides of SEQ ID NO: 56, wherein the probe is less than 50, less than 45, less than 40, less than 35, or less than 30 nucleotides long. In some embodiments, the probe for detecting UPK1B comprises at least 8, at least 9, at least 10, at least 11, at least 12, at least 13, at least 14, or at least 15, at least 16, at least 17, or at least 18 nucleotides of SEQ ID NO: 53, wherein the probe is less than 50, less than 45, less than 40, less than 35, or less than 30 nucleotides long. In some embodiments, each bladder cancer marker probe comprises a dye, and wherein each dye is detectably different from the other three labels. In some embodiments, each bladder cancer marker probe comprises a fluorescent dye and a quencher molecule.

In some embodiments, a composition further comprises an endogenous control primer pair for detecting an endogenous control. In some embodiments, the endogenous control is selected from ABL, GUSB, GAPDH, TUBB, and UPK1a. In some embodiments, the endogenous control is ABL. In some embodiments, the endogenous control primer pair comprises a first primer comprising SEQ ID NO: 8 and a second primer comprising SEQ ID NO: 9, wherein each primer is less than 50, less than 45, less than 40, less than 35, or less than 30 nucleotides long. In some embodiments, the endogenous control primer pair comprises a first primer comprising SEQ ID NO: 41 and a second primer comprising SEQ ID NO: 42, wherein each primer is less than 50, less than 45, less than 40, less than 35, or less than 30 nucleotides long. In some embodiments, the endogenous control primer pair comprises a first primer comprising at least 8, at least 9, at least 10, at least 11, at least 12, at least 13, at least 14, or at least 15, at least 16, at least 17, or at least 18 nucleotides of SEQ ID NO: 8 and a second primer comprising at least 8, at least 9, at least 10, at least 11, at least 12, at least 13, at least 14, or at least 15, at least 16, at least 17, or at least 18 nucleotides of SEQ ID NO: 9, wherein each primer is less than 50, less than 45, less than 40, less than 35, or less than 30 nucleotides long. In some embodiments, the endogenous control primer pair comprises a first primer comprising at least 8, at least 9, at least 10, at least 11, at least 12, at least 13, at least 14, or at least 15, at least 16, at least 17, or at least 18 nucleotides of SEQ ID NO: 41 and a second primer comprising at least 8, at least 9, at least 10, at least 11, at least 12, at least 13, at least 14, or at least 15, at least 16, at least 17, or at least 18 nucleotides of SEQ ID NO: 42, wherein each primer is less than 50, less than 45, less than 40, less than 35, or less than 30 nucleotides long.

In some embodiments, a composition further comprises an endogenous control probe for detecting an endogenous control amplicon. In some embodiments, the endogenous control is selected from ABL, GUSB, GAPDH, TUBB, and UPK1a. In some embodiments, the endogenous control is ABL. In some embodiments, the endogenous control probe comprises at least 8, at least 9, at least 10, at least 11, at least 12, at least 13, at least 14, or at least 15, at least 16, at least 17, or at least 18 nucleotides of SEQ ID NO: 10, 11, 12, or 43, wherein the endogenous control probe is less than 50, less than 45, less than 40, less than 35, or less than 30 nucleotides long. In some embodiments, the endogenous control probe comprises a dye that is detectably different from the dyes of the bladder cancer marker probes.

In some embodiments, a composition is a lyophilized composition. In some embodiments, the composition is a solution. In some embodiments, the composition further comprises urothelial cells. In some embodiments, the urothelial cells are from a urine sample.

Further embodiments and details of the inventions are described below.

4. DETAILED DESCRIPTION

4.1. Definitions

To facilitate an understanding of the present invention, a number of terms and phrases are defined below:

As used herein, the terms "detect", "detecting" or "detection" may describe either the general act of discovering or discerning or the specific observation of a detectably labeled composition.

As used herein, the term "detectably different" refers to a set of labels (such as dyes) that can be detected and distinguished simultaneously.

As used herein, the terms "patient" and "subject" are used interchangeably to refer to a human. In some embodiments, the methods described herein may be used on samples from non-human animals.

As used herein, "bladder cancer" is a tumor, such as a transitional cell carcinoma, arising from the lining of the bladder, and includes low grade and high grade bladder cancers, as well as metastatic bladder cancer. "Low grade bladder cancer" refers to superficial tumors that project into the interior of the bladder cavity. Low grade bladder cancers have a high rate of recurrence. "High grade bladder cancer" refers to a fast-growing and/or invasive tumor that invades the bladder wall. High grade bladder cancers have the potential to spread (i.e., metastasize) to other areas of the body. "Metastatic bladder cancer" refers to invasive bladder cancer that has spread to one or more locations in the body beyond the bladder.

As used herein, the terms "oligonucleotide," "polynucleotide," "nucleic acid molecule," and the like, refer to nucleic acid-containing molecules, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "oligonucleotide," refers to a single-stranded polynucleotide having fewer than 500 nucleotides. In some embodiments, an oligonucleotide is 8 to 200, 8 to 100, 12 to 200, 12 to 100, 12 to 75, or 12 to 50 nucleotides long. Oligonucleotides may be referred to by their length, for example, a 24 residue oligonucleotide may be referred to as a "24-mer."

As used herein, the term "complementary" to a target RNA (or target region thereof), and the percentage of "complementarity" of the probe sequence to that of the target RNA sequence is the percentage "identity" to the sequence of target RNA or to the reverse complement of the sequence of the target RNA. In determining the degree of "complementarity" between probes used in the compositions described herein (or regions thereof) and a target RNA, such as those disclosed herein, the degree of "complementarity" is expressed as the percentage identity between the sequence of the probe (or region thereof) and sequence of the target RNA or the reverse complement of the sequence of the target RNA that best aligns therewith. The percentage is calculated by counting the number of aligned bases that are identical as between the 2 sequences, dividing by the total number of contiguous nucleotides in the probe, and multiplying by 100. When the term "complementary" is used, the subject oligonucleotide is at least 90% complementary to the target molecule, unless indicated otherwise. In some embodiments, the subject oligonucleotide is at least 91%, at least 92%, at least 93%, at least 94%, at least 95%, at least 96%, at least 97%, at least 98%, at least 99%, or 100% complementary to the target molecule.

A "primer" or "probe" as used herein, refers to an oligonucleotide that comprises a region that is complementary to a sequence of at least 8 contiguous nucleotides of a target nucleic acid molecule, such as an mRNA or a DNA reverse-transcribed from an mRNA. In some embodiments, a primer or probe comprises a region that is complementary to a sequence of at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of a target molecule. When a primer or probe comprises a region that is "complementary to at least x contiguous nucleotides of a target molecule," the primer or probe is at least 95% complementary to at least x contiguous nucleotides of the target molecule. In some embodiments, the primer or probe is at least 96%, at least 97%, at least 98%, at least 99%, or 100% complementary to the target molecule.

A "sample," as used herein, includes urine samples (including samples derived from urine samples), and other types of human samples. As used herein, urine samples include, but are not limited to, whole urine, a sample comprising cells from a urine sample, a sample comprising the cell pellet isolated by centrifugation of a urine sample, a sample comprising cells isolated by filtration of a urine sample, and the like. In some embodiments, a urine sample comprises a preservative, such as a preservative that causes damage, such as lysis, of red and/or white blood cells. In some embodiments, a sample is a human sample other than a urine sample, such as a tissue sample (including a bladder tissue and/or bladder tumor sample), a blood sample (including whole blood, serum, plasma, etc.), etc. In some embodiments, a sample is a bladder washing sample.

As used herein, "corticotrophin releasing hormone" or "CRH" refers to an mRNA that encodes CRH, as well as the CRH protein. In some embodiments, CRH is human CRH. Nonlimiting exemplary human CRH mRNA sequences are found at GenBank Accession No. NM_000756, and at SEQ ID NO: 1.

As used herein, "insulin-like growth factor 2" or "IGF2" refers to an mRNA that encodes IGF2, as well as the IGF2 protein. In some embodiments, IGF2 is human IGF2. Nonlimiting exemplary human IGF2 mRNA sequences are shown in SEQ ID NOs: 2 to 4.

As used herein, "keratin 20" or "KRT20" refers to an mRNA that encodes KRT20, as well as the KRT20 protein. In some embodiments, KRT20 is human KRT20. Nonlimiting exemplary human KRT20 mRNA sequences are found at GenBank Accession No. NM_019010, and at SEQ ID NO: 5.

As used herein, "annexin A10" or "ANXA10" refers to an mRNA that encodes ANXA10, as well as the ANXA10 protein. In some embodiments, ANXA10 is human ANXA10. Nonlimiting exemplary human ANXA10 mRNA sequences are found at GenBank Accession No. NM_007193, and at SEQ ID NO: 6.

As used herein, "androgen receptor" or "AR" refers to an mRNA that encodes AR, as well as the AR protein. In some embodiments, AR is human AR. Nonlimiting exemplary human AR mRNA sequences are found at GenBank Accession Nos. NM_000044 and NM_001011645, and at SEQ ID NOs: 49 and 57.

As used herein, "uroplakin 1B" or "UPK1B" refers to an mRNA that encodes UPK1B, as well as the UPK1B protein. In some embodiments, UPK1B is human UPK1B. Nonlimiting exemplary human UPK1B mRNA sequences are found at GenBank Accession No. NM_006952 and at SEQ ID NO: 50.

An "endogenous control," as used herein refers to a moiety that is naturally present in the sample to be used for detection, and which can be used to normalize the levels of the bladder cancer markers described herein (including, but not limited to, AR, UPK1B, CRH, IGF2, KRT20, and ANXA10). Thus, an endogenous control is typically a moiety that is present at similar levels from cell to cell, and at similar levels in cells from subjects with bladder cancer and cells from subjects without bladder cancer. In some embodiments, an endogenous control is an RNA (such as an mRNA, tRNA, ribosomal RNA, etc.). Nonlimiting exemplary endogenous controls include ABL mRNA, GUSB mRNA, GAPDH mRNA, TUBB mRNA, and UPK1a mRNA. Nonlimiting exemplary human ABL mRNA sequences are found at GenBank Accession No. NM_007313, and at SEQ ID NO: 7. In some embodiments, an endogenous control is selected that can be detected in the same manner as the bladder cancer markers are detected and, in some embodiments, simultaneously with the bladder cancer markers.

An "exogenous control," as used herein, refers to a moiety that is added to a sample to be used for detection. An exogenous control is typically selected that is not expected to be present in the sample to be used for detection, or is present at very low levels in the sample such that the amount of the moiety naturally present in the sample is either undetectable or is detectable at a much lower level than the amount added to the sample as an exogenous control. In some embodiments, an exogenous control comprises a nucleotide sequence that is not expected to be present in the sample type used for detection of the bladder cancer markers. In some embodiments, an exogenous control comprises a nucleotide sequence that is not known to be present in the species from whom the sample is taken. In some embodiments, an exogenous control comprises a nucleotide sequence from a different species than the subject from whom the sample was taken. In some embodiments, an exogenous control comprises a nucleotide sequence that is not known to be present in any species. In some embodiments, an exogenous control is selected that can be detected in the same manner as the bladder cancer markers are detected and, in some embodiments, simultaneously with the bladder cancer markers. In some embodiments, an exogenous control is an RNA. In some embodiments, an RNA is an Armored RNA®, which comprises RNA packaged in a bacteriophage protective coat. See, e.g., Walker-Peach et al., *Clin. Chem.* 45:12: 2079-2085 (1999).

In the sequences herein, "U" and "T" are used interchangeably, such that both letters indicate a uracil or thymine at that position. One skilled in the art will understand from the context and/or intended use whether a uracil or thymine is intended and/or should be used at that position in the sequence. For example, one skilled in the art would understand that native RNA molecules typically include uracil, while native DNA molecules typically include thymine Thus, where an RNA sequence includes "T", one skilled in the art would understand that that position in the native RNA is likely a uracil.

In the present disclosure, "a sequence selected from" encompasses both "one sequence selected from" and "one or more sequences selected from." Thus, when "a sequence selected from" is used, it is to be understood that one, or more than one, of the listed sequences may be chosen.

In the present disclosure, a method that comprises detecting a "a set of bladder cancer markers consisting of . . . " involves detection of only the bladder cancer markers of the set, and not any further bladder cancer markers. The method may comprise additional components or steps, however, such as detecting endogenous and/or exogenous controls. Similarly, a method or composition that comprises "a set of bladder cancer marker primer pairs" and/or "a set of bladder cancer marker probes" can include primer pairs and/or probes for only the bladder cancer markers of the set, and not for any other bladder cancer markers. The method or composition may comprise additional components, however, such as one or more endogenous control primer pairs and/or one or more exogenous control primer pairs.

4.2. Detecting Bladder Cancer

The present inventors have developed an assay for detecting bladder cancer that involves detecting androgen receptor (AR) and/or uroplakin 1B (UPK1B), and optionally, at least one marker selected from CRH, IGF2, KRT20 and ANXA10. The presently described assays have several advantages over existing and previously described diagnostics for bladder cancer. For example, the present assays do not rely on cytology, which can be costly, and requires trained cytologists for accurate interpretation of results. Instead, the present assays rely on the polymerase chain reaction (PCR), and can be carried out in a substantially automated manner, for example, using the GeneXpert® system (Cepheid, Sunnyvale, Calif.). The present assays can be completed in under 3 hours, and in some embodiments, under 2 hours, using an automated system, for example, the GeneXpert® system. Existing tests can require several days for a laboratory to complete and send results. In addition, the present assay can be carried out on much smaller volumes of urine (in some embodiments, 5 ml or less). Thus, the present assays, which rely on PCR rather than cytology, allows for a fast, one-pot reaction for diagnosis of bladder cancer, which in many instances can be carried out at the point of care using an automated system such as GeneXpert®.

4.2.1. General Methods

Compositions and methods for detecting bladder cancer are provided. In some embodiments, compositions and methods for detecting low grade bladder cancer are provided. In some embodiments, compositions and methods of detecting high grade bladder cancer are provided. In some embodiments, compositions and methods for monitoring the recurrence of bladder cancer are provided.

In some embodiments, a method of detecting bladder cancer comprises detecting the level of AR in a sample. In some embodiments, a method of detecting bladder cancer comprises detecting the level of UPK1B in a sample. In some embodiments, a method of detecting bladder cancer comprises detecting the level of AR and UPK1B in a sample. In some embodiments, a method of detecting bladder cancer comprises detecting the level of at least one additional marker selected from CRH, IGF2, KRT20 and ANXA10. In some embodiments, a method of detecting bladder cancer comprises detecting the levels of a set of bladder cancer markers comprising, or consisting of, AR, CRH, IGF2, KRT20, and ANXA10; or UPK1B, CRH, IGF2, KRT20, and ANXA10; or AR, CRH, IGF2, and KRT20; or UPK1B, CRH, IGF2, and KRT20.

In some embodiments, a method of detecting bladder cancer further comprises detecting the level of at least one endogenous control. In some embodiments, a method of detecting bladder cancer further comprises detecting the level of at least one exogenous control. In some embodiments, a method of detecting bladder cancer further comprises detecting the levels of at least one endogenous control and at least one exogenous control.

In some embodiments, a method of detecting bladder cancer comprises detecting the level of AR mRNA in a sample. In some embodiments, a method of detecting bladder cancer comprises detecting the level of UPK1B mRNA in a sample. In some embodiments, a method of detecting bladder cancer comprises detecting the level of AR mRNA and UPK1B mRNA in a sample. In some embodiments, a method of detecting bladder cancer comprises detecting the level of at least one additional marker selected from CRH, IGF2, KRT20, and ANXA10 mRNA. In some embodiments, a method of detecting bladder cancer comprises detecting the levels of a set of bladder cancer markers comprising, or consisting of, AR, CRH, IGF2, KRT20, and ANXA10 mRNA; or UPK1B, CRH, IGF2, KRT20, and ANXA10 mRNA; or AR, CRH, IGF2, and KRT20 mRNA; or UPK1B, CRH, IGF2, and KRT20 mRNA.

In some embodiments, a method of detecting bladder cancer further comprises detecting the level of at least one endogenous control RNA. In some embodiments, a method of detecting bladder cancer further comprises detecting the level of at least one exogenous control RNA. In some embodiments, a method of detecting bladder cancer further comprises detecting the levels of at least one endogenous control RNA and at least one exogenous control RNA.

In the present disclosure, the term "target RNA" is used for convenience to refer to AR and UPK1B, and also to other target RNAs, such as CRH, IGF2, KRT20 and ANXA10 mRNAs and exogenous and/or endogenous control RNAs. Thus, it is to be understood that when a discussion is presented in terms of a target RNA, that discussion is specifically intended to encompass AR, UPK1B, CRH, IGF2, KRT20 and ANXA10 mRNAs, and/or other target RNAs.

In some embodiments, the level of one or more target RNAs is detected in a urine sample. In some embodiments, the level of one or more target RNAs is determined in a urine sample that has been preserved in a manner that causes damage, such as lysis, to red blood cells and/or white blood cells. In some embodiments, the level of one or more target RNAs is detected in urothelial cells isolated from a urine sample, either with or without preservative treatment. In some embodiments, the urothelial cells are isolated by filtration.

In some embodiments, detection of an elevated level of AR mRNA in a sample from a subject indicates the presence of bladder cancer in the subject. In some embodiments, detection of an elevated level of UPK1B in a sample from a subject indicates the presence of bladder cancer in the subject. In some embodiments, detection of an elevated level of one or more target RNAs selected from CRH, IGF2, KRT20 and ANXA10 in a sample from a subject indicates the presence of bladder cancer in the subject. In some embodiments, the detecting is done quantitatively. In other embodiments, the detecting is done qualitatively. In some embodiments, detecting a target RNA comprises forming a complex comprising a polynucleotide and a nucleic acid selected from a target RNA, a DNA amplicon of a target RNA, and a complement of a target RNA. In some embodiments, detecting a target RNA comprises RT-PCR. In some embodiments, detecting a target RNA comprises quantitative RT-PCT. In some embodiments, the level of the target RNA is compared to a normal or control level of the target RNA.

In some embodiments, the levels of target RNAs, such as AR, UPK1B, CRH, IGF2, KRT20 and ANXA10 mRNA, can be measured in samples collected at one or more times from a patient to monitor the status or progression of bladder cancer in the patient. In some embodiments, a patient with a history of bladder cancer, such as a history of low grade bladder cancer or a history of high grade bladder cancer, is monitored by detecting the levels of AR and/or UPK1B mRNA, and optionally at least one mRNA selected from CRH, IGF2, KRT20 and ANXA10, at regular or semi-regular intervals. In some such embodiments, the patient is monitored by detecting the levels of the target RNAs at least once per month, at least once every two months, at least once every three months, at least once every four months, at least once every five months, at least once every six months, at least once every nine months, at least once per year, or at least once every two years.

In some embodiments, the levels of target RNAs, such as UPK1B, CRH, IGF2, KRT20 and ANXA10 mRNA, can be measured in samples collected at one or more times from a patient to monitor response to anti-androgen therapy. Non-limiting exemplary anti-androgen agents include flutamide (Eulexin®), bicalutamide (Casodex®), and nilutamide (Nilandron®). In some embodiments, a patient undergoing anti-androgen therapy for bladder cancer is monitored by detecting the levels of AR and/or UPK1B mRNA, and optionally at least one mRNA selected from CRH, IGF2, KRT20 and ANXA10, at regular or semi-regular intervals. In some such embodiments, the patient is monitored by detecting the levels of the target RNAs at least once per month, at least once every two months, at least once every three months, at least once every four months, at least once every five months, at least once every six months, at least once every nine months, at least once per year, or at least once every two years. In some embodiments, a reduction in the level of AR and/or UPK1B during treatment indicates that the bladder cancer is responding to the anti-androgen therapy.

In some embodiments, a sample to be tested is a urine sample (such as a voided urine sample), or is derived from a urine sample. In some embodiments, a preservative is added to the urine sample, for example, to damage (e.g., lyse) red and/or white blood cells present in the urine sample. By damaging or lysing red and/or white blood cells prior to isolation of urothelial cells, contamination by the red and/or white blood cells can be reduced. In some embodiments, the urine sample is centrifuged to concentrate the urothelial cells. In some embodiments, the urine sample is filtered to isolate the urothelial cells from other urine and preservative materials. In some such embodiments, the filter is part of a GeneXpert cartridge (Cepheid, Sunnyvale, Calif.).

In some embodiments, less than 5 ml, less than 4 ml, less than 3 ml, or less than 2 ml of urine are used in the present methods. In some embodiments, the urine sample is analyzed without a centrifugation step. Thus, in some embodiments, the present methods are carried out in the absence of centrifugation. In some embodiments, a larger volume of urine may be used, and in some such embodiments, a centrifugation step may be used to concentrate the urothelial cells prior to analysis.

In some embodiments, the sample to be tested is another bodily fluid, such as blood, sputum, mucus, saliva, semen, etc. In some embodiments, a sample to be tested is a blood sample. In some embodiments, the blood sample is whole blood. In some embodiments, the blood sample is a sample of blood cells. In some embodiments, the blood sample is plasma. In some embodiments, the blood sample is serum.

The clinical sample to be tested is, in some embodiments, fresh (i.e., never frozen). In other embodiments, the sample is a frozen specimen. In some embodiments, the sample is a tissue sample, such as a formalin-fixed paraffin embedded sample. In some embodiments, the sample is a liquid cytology sample.

In some embodiments, the methods described herein are used for early detection of bladder cancer in a sample of urothelial cells, such as those obtained from voided urine. In some embodiments, the methods described herein are used for monitoring for recurrence of bladder cancer using a sample of urothelial cells, such as those obtained from voided urine.

In some embodiments, the sample to be tested is obtained from an individual who has one or more of the following risk factors: history of smoking, hematuria, history of bladder or other cancers, and exposure to known carcinogens such as benzene. In some embodiments, the sample is obtained from an individual who has diagnostic signs or clinical symptoms that may be associated with bladder cancer, such as blood in the urine, frequent urination, urinary urgency, incontinence, difficulty urinating, abdominal pain, unexplained weight loss and/or loss of appetite. In some embodiments, the sample to be tested is obtained from an individual who has previously been diagnosed with low grade or high grade bladder cancer. In some such embodiments, the individual is monitored for recurrence of bladder cancer.

Bladder cancer can be divided into stages, which indicate the growth pattern of the primary tumor. Table A shows the stages of bladder cancer according to the American Joint Committee on Cancer (AJCC). The stages shown cover only the "T" portion of the "TNM" system. The "T" portion refers to the primary tumor, while "N" refers to spread of the cancer to the lymph nodes, and "M" refers to whether the cancer has metastasized to distant sites.

TABLE A

Bladder cancer stages

| Stage | description |
|---|---|
| T0 | No evidence of primary tumor |
| Ta | Non-invasive papillary carcinoma |
| Tis/CIS | Non-invasive flat carcinoma (carcinoma in situ) |
| T1 | Tumor has grown from the lining of the bladder into the connective tissue, but has not grown into the muscle layer of the bladder |

TABLE A-continued

Bladder cancer stages

| Stage | description |
|---|---|
| T2 | Tumor has grown into the muscle layer |
| T2a | Tumor has grown into the inner half of the muscle layer |
| T2b | Tumor has grown into the outer half of the muscle layer |
| T3 | Tumor has grown through the muscle layer of the bladder and into the fatty tissue that surrounds it |
| T3a | Tumor's spread to fatty tissue can only be seen under a microscope |
| T3b | Tumor's spread to fatty tissue can be seen on imaging tests or can be seen or felt by surgeon |
| T4 | Tumor has spread beyond the fatty tissue to nearby organs or structures |
| T4a | Tumor has spread to the stroma of the prostate, or to the uterus and/or vagina |
| T4b | Tumor has spread to the pelvic wall or abdominal wall |

In some embodiments, methods described herein can be used for routine screening of healthy individuals with no risk factors. In some embodiments, methods described herein are used to screen asymptomatic individuals having one or more of the above-described risk factors.

In some embodiments, the methods described herein can be used to detect low grade bladder cancer. In some embodiments, the methods described herein can be used to detect high grade bladder cancer. In some embodiments, the methods described herein detect at least 15%, at least 17%, at least 20%, at least 22%, at least 25%, at least 27%, at least 30%, at least 31%, at least 32%, at least 33%, at least 34%, or at least 35% of low grade bladder cancers. In some embodiments, the methods described herein detect at least 85%, at least 87%, at least 90%, at least 91%, at least 92%, at least 93%, at least 94%, at least 95%, at least 96%, at least 97%, at least 98%, or at least 99% of high grade bladder cancers.

In some embodiments, the methods described herein can be used to assess the effectiveness of a treatment for bladder cancer in a patient. In some embodiments, target RNA levels, such as the levels of AR and/or UPK1B mRNA, and optionally, at least one mRNA selected from CRH, IGF2, KRT20 and ANXA10, are determined at various times during the treatment, and are compared to target RNA levels from an archival sample taken from the patient before the beginning of treatment. In some embodiments, target RNA levels are compared to target RNA levels from an archival normal sample taken from the patient. Ideally, target RNA levels in the normal sample evidence no aberrant changes in target RNA levels.

In some embodiments, use of the levels of AR and/or UPK1B mRNA, and optionally, at least one mRNA selected from CRH, IGF2, KRT20 and ANXA10, for monitoring recurrence of bladder cancer is provided. In some embodiments, an elevated level of one or more, two or more, three or more, or four or more, five or more, or all six mRNAs indicates that bladder cancer has recurred in the patient.

In any of the embodiments described herein, RNA levels may be detected concurrently or simultaneously in the same or separate assay reactions. In some embodiments, RNA levels are detected at different times, e.g., in serial assay reactions.

In some embodiments, a method comprises detecting the levels of AR and/or UPK1B mRNA, and optionally, at least one mRNA selected from CRH, IGF2, KRT20 and ANXA10 in a sample from a subject, wherein detection of a level of any one of the mRNAs that is greater than a normal level of the RNA indicates the presence of bladder cancer in the subject. In some embodiments, detection of elevated levels of two, three, four, five, or six bladder cancer marker mRNAs indicates the presence of bladder cancer in the subject. In some embodiments, detection of elevated levels of at least two, at least three, at least four, or at least five of the bladder cancer marker mRNAs indicates a greater risk of high grade bladder cancer.

In some embodiments, a method of facilitating diagnosis of bladder cancer in a subject is provided. Such methods comprise detecting the level of AR and/or UPK1B mRNA, and optionally, at least one mRNA selected from CRH, IGF2, KRT20 and ANXA10 in a sample from the subject. In some embodiments, information concerning the levels of AR and/or UPK1B mRNA, and optionally, at least one mRNA selected from CRH, IGF2, KRT20 and ANXA10 in the sample from the subject is communicated to a medical practitioner. A "medical practitioner," as used herein, refers to an individual or entity that diagnoses and/or treats patients, such as a hospital, a clinic, a physician's office, a physician, a nurse, or an agent of any of the aforementioned entities and individuals. In some embodiments, detecting the levels of AR and/or UPK1B mRNA, and optionally, at least one mRNA selected from CRH, IGF2, KRT20 and ANXA10 is carried out at a laboratory that has received the subject's sample from the medical practitioner or agent of the medical practitioner. The laboratory carries out the detection by any method, including those described herein, and then communicates the results to the medical practitioner. A result is "communicated," as used herein, when it is provided by any means to the medical practitioner. In some embodiments, such communication may be oral or written, may be by telephone, in person, by e-mail, by mail or other courier, or may be made by directly depositing the information into, e.g., a database accessible by the medical practitioner, including databases not controlled by the medical practitioner. In some embodiments, the information is maintained in electronic form. In some embodiments, the information can be stored in a memory or other computer readable medium, such as RAM, ROM, EEPROM, flash memory, computer chips, digital video discs (DVD), compact discs (CDs), hard disk drives (HDD), magnetic tape, etc.

In some embodiments, methods of detecting the presence bladder cancer are provided. In some embodiments, methods of diagnosing bladder cancer are provided. In some embodiments, the method comprises obtaining a sample from a subject and providing the sample to a laboratory for detection of levels of AR and/or UPK1B mRNA, and optionally, at least one mRNA selected from CRH, IGF2, KRT20 and ANXA10 in the sample. In some embodiments, the method further comprises receiving a communication from the laboratory that indicates the level of AR and/or UPK1B mRNA, and optionally, at least one mRNA selected from CRH, IGF2, KRT20 and ANXA10 in the sample. In some embodiments, bladder cancer is present if the level of any one of the four mRNAs is greater than a normal or control level of the mRNA. A "laboratory," as used herein, is any facility that detects the levels of target RNA in a sample by any method, including the methods described herein, and communicates the level to a medical practitioner. In some embodiments, a laboratory is under the control of a medical practitioner. In some embodiments, a laboratory is not under the control of the medical practitioner.

When a laboratory communicates the level of a target RNA to a medical practitioner, in some embodiments, the laboratory communicates a numerical value representing the level of the RNA in the sample, with or without providing a numerical value for a normal level. In some embodiments, the laboratory communicates the level of the RNA by providing a qualitative value, such as "high," "low," "elevated," "decreased," "positive" (such as "AR positive" or "AR and CRH positive"), etc. In some embodiments, the laboratory communicates a suggested diagnosis, such as "bladder cancer positive" or "positive for cancer," and the like; or simply "cancer positive" or "cancer negative."

As used herein, when a method relates to detecting bladder cancer, determining the presence of bladder cancer, monitoring for bladder cancer, and/or diagnosing bladder cancer, the method includes activities in which the steps of the method are carried out, but the result is negative for the presence of bladder cancer. That is, detecting, determining, monitoring, and diagnosing bladder cancer include instances of carrying out the methods that result in either positive or negative results.

In some embodiments, more than one RNA is detected simultaneously in a single reaction. In some embodiments, AR mRNA and at least one mRNA selected from CRH, IGF2, KRT20 and ANXA10 are detected simultaneously in a single reaction. In some embodiments, UPK1B mRNA and at least one mRNA selected from CRH, IGF2, KRT20 and ANXA10 are detected simultaneously in a single reaction. In some embodiments, AR and UPK1B mRNA and at least one mRNA selected from CRH, IGF2, KRT20 and ANXA10 are detected simultaneously in a single reaction. In some embodiments, at least one endogenous control and/or at least one exogenous control are detected simultaneously with the bladder cancer markers in a single reaction.

4.2.2. Exemplary Controls

In some embodiments, a normal level (a "control") of a target RNA, such as AR and/or UPK1B mRNA, and optionally, at least one mRNA selected from CRH, IGF2, KRT20 and ANXA10, can be determined as an average level or range that is characteristic of normal urothelial cells or other reference material, against which the level measured in the sample can be compared. The determined average or range of a target RNA in normal subjects can be used as a benchmark for detecting above-normal levels of the target RNA that are indicative of bladder cancer. In some embodiments, normal levels of a target RNA can be determined using individual or pooled RNA-containing samples from one or more individuals, such as from normal urothelial cells isolated from urine of healthy individuals.

In some embodiments, determining a normal level of a target RNA comprises detecting a complex comprising a polynucleotide for detection hybridized to a nucleic acid selected from a target RNA, a DNA amplicon of the target RNA, and a complement of the target RNA. That is, in some embodiments, a normal level can be determined by detecting a DNA amplicon of the target RNA, or a complement of the target RNA rather than the target RNA itself. In some embodiments, a normal level of such a complex is determined and used as a control. The normal level of the complex, in some embodiments, correlates to the normal level of the target RNA. Thus, when a normal level of a target is discussed herein, that level can, in some embodiments, be determined by detecting such a complex.

In some embodiments, a normal level of a target RNA is, or has been, determined by the same method as the level of the target RNA from a patient sample. In some such embodiments, the method is RT-PCR (such as real-time RT-PCR, quantitative RT-PCR, etc.).

In some embodiments, a control comprises RNA from cells of a single individual, e.g., from normal urothelial cells isolated from urine of a healthy individual. In some embodiments, a control comprises RNA from blood, such as whole blood or serum, of a single individual. In some embodiments, a control comprises RNA from a pool of cells from multiple individuals. In some embodiments, a control comprises RNA from a pool of urine from multiple individuals. In some embodiments, a control comprises commercially-available human RNA (see, for example, Ambion). In some embodiments, a normal level or normal range has already been predetermined prior to testing a sample for an elevated level.

In some embodiments, the normal level of a target RNA can be determined from one or more continuous cell lines, typically cell lines previously shown to have levels of RNAs that approximate the levels in normal urothelial cells.

In some embodiments, quantitation of target RNA levels requires assumptions to be made about the total RNA per cell and the extent of sample loss during sample preparation. In order to correct for differences between different samples or between samples that are prepared under different conditions, the quantities of target RNAs in some embodiments are normalized to the levels of at least one endogenous control and/or at least one exogenous control.

In some embodiments, a control RNA is an endogenous control RNA. An endogenous control RNA may be any RNA suitable for the purpose, for example, RNAs that are present at approximately constant levels from cell to cell and in urothelial cells from both bladder cancer and non-bladder cancer patients. Nonlimiting exemplary endogenous control RNAs include ABL, GUSB, GAPDH, TUBB, and UPK1a. In some embodiments, one endogenous control is used for normalization. In some embodiments, more than one endogenous control is used for normalization.

In some embodiments, the level of a target RNA, such as AR and/or UPK1B mRNA, and optionally, at least one of CRH, IGF2, KRT20 and ANXA10 mRNA, is normalized to an endogenous control RNA. Normalization may comprise, for example, determination of the difference of the level of the target RNA to the level of the endogenous control RNA. In some such embodiments, the level of the RNAs are represented by a Ct value obtained from quantitative PCR. In some such embodiments, the difference is expressed as $\Delta$Ct. $\Delta$Ct may be calculated as Ct[target RNA]−Ct[endogenous control] or Ct[endogenous control]−Ct[target RNA]. In certain embodiments, $\Delta$Ct=Ct[endogenous control]−Ct[marker]. In some embodiments, a threshold $\Delta$Ct value is set, above or below which bladder cancer is indicated. In some such embodiments, the $\Delta$Ct threshold is set as the $\Delta$Ct value below which 95% of normal samples are correctly characterized. In some such embodiments, a $\Delta$Ct value that is higher than the threshold $\Delta$Ct value is indicative of bladder cancer.

In some embodiments, linear discriminant analysis (LDA) is used, for example, to combine two or more of the markers into a single combined scale. In some such embodiments, a single threshold value is used for the markers included in the LDA.

In some embodiments, a control RNA is an exogenous control RNA. In some such embodiments, the exogenous control RNA is an Armored RNA®, which is protected by a bacteriophage coat. An exogenous control RNA may, in some embodiments, be used to determine if the detection assay reaction has failed, and therefore the results are not meaningful. For example, if an exogenous control RNA is not amplified in the assay reaction, then a negative result for the target RNAs is likely not meaningful because the levels reflect the reaction failing rather than the target RNA levels being low. Reaction failure can occur for any number of reasons, including, but not limited to, the presence of a reaction inhibitor in the sample (an "inhibitory sample"), compromised reagents, the presence of an RNAse, etc. An exogenous RNA control may be added at any stage of the sample collection and analysis. For example, in some embodiments, the exogenous control RNA is added to the sample at the time preservative is added, is added to the sample when it is received by the diagnostic laboratory, is added to the sample immediately prior to analysis, or is added to the sample during analysis (as a nonlimiting example, during or after lysis of the urothelial cells but before addition of the amplification reagents).

In some embodiments, the level of a target RNA, such as such as AR, UPK1B, CRH, IGF2, KRT20 or ANXA10 mRNA, is compared to a reference level, e.g., from a confirmed bladder cancer. In some such embodiments, a similar level of a target RNA relative to the reference sample indicates bladder cancer.

In some embodiments, a level of a target RNA, such as AR, UPK1B, CRH, IGF2, KRT20 or ANXA10 mRNA, that is at least about 20%, 30%, 40%, 50%, 60%, 70%, 80%, or 90% greater than a normal level of the respective target RNA indicates the presence of bladder cancer. In some embodiments, a level of a target RNA, such as AR, UPK1B, CRH, IGF2, KRT20 or ANXA10 mRNA, that is at least about two-fold, at least about 3-fold, at least about 4-fold, at least about 5-fold, at least about 6-fold, at least about 7-fold, at least about 8-fold, at least about 9-fold, or at least about 10-fold greater than a normal level of the respective target RNA indicates the presence of bladder cancer.

In some embodiments, a control level of a target RNA, such as AR, UPK1B, CRH, IGF2, KRT20 or ANXA10 mRNA, is determined contemporaneously, such as in the same assay or batch of assays, as the level of the target RNA in a sample. In some embodiments, a control level of a target RNA is not determined contemporaneously as the level of the target RNA in a sample. In some such embodiments, the control level has been determined previously.

In some embodiments, the level of an endogenous control and/or an exogenous control is determined contemporaneously, such as in the same assay or batch of assays, as the level of the target RNA in a sample. In some embodiments, an assay comprises reagents for determining the levels of AR and/or UPK1B mRNA, and optionally, at least one mRNA selected from CRH, IGF2, KRT20 and ANXA10, and an endogenous control simultaneously in the same assay reaction. In some embodiments, an assay comprises reagents for determining the levels of AR and/or UPK1B mRNA, and optionally, at least one mRNA selected from CRH, IGF2, KRT20 and ANXA10, and an exogenous control simultaneously in the same assay reaction. In some embodiments, an assay comprises reagents for determining the levels of AR and/or UPK1B mRNA, and optionally, at least one mRNA selected from CRH, IGF2, KRT20, ANXA10, an endogenous control, and an exogenous control simultaneously in the same assay reaction. In some such embodiments, for example, an assay reaction comprises primer sets for amplifying AR and/or UPK1B, and optionally, at least one mRNA selected from CRH, IGF2, KRT20 and ANXA10, a primer set for amplifying an endogenous control and/or a primer set for amplifying an exogenous control, and detectably different labeled probes for detecting the amplification products (such as, for example, TaqMan® probes with detectably different dyes for each different amplicon to be detected).

In some embodiments, the level of a target RNA is not compared to a control level, for example, when it is known that the target RNA is present at very low levels, or not at all, in normal cells. In such embodiments, detection of a high level of the target RNA in a sample is indicative of bladder cancer.

4.2.3. Exemplary Sample Preparation 4.2.3.1. Exemplary Urine Preservatives

In some embodiments, a preservative is added to the urine sample. In some embodiments, the preservative is added within one hour, two hours, three hours, or six hours of the time the urine sample was collected (e.g., voided). In some embodiments, a preservative is added to the urine sample within one hour, two hours, three hours, or six hours before the sample is analyzed by the methods described herein.

In some embodiments, a preservative causes damage, such as lysis, of red blood cells and/or white blood cells, but does not damage urothelial cells. Red blood cells and/or white blood cells may be present in the urine as a result of a tumor and/or infection. In some such embodiments, adding the preservative allows for improved enrichment of the urothelial cells, for example by filtration. In some embodiments, a preservative lowers the pH of the urine sample and improves solubility of urine salts. In some such embodiments, the preservative facilitates passage of the salts through a filter in a filtration step. A desirable pH of preserved urine to be passed through a filter is between about 2.5 and 4. In some embodiments, a desirable pH of preserved urine is between about 2.7 and 3.7. In some embodiments, a desirable pH of preserved urine is between about 3 and 3.5. In some embodiments, a desirable pH of preserved urine is about 3.2.

In some embodiments a preservative is added such that the urine/preservative sample comprises 0.875M to 2.625M guanidine hydrochloride, 0.25% to 0.75% N-acetyl-L-cysteine, 6.25 to 18.75 mM sodium citrate, and 0.625% to 1.875% Tween-20, and has a pH of 3 to 3.5. In some embodiments a preservative is added such that the urine/preservative sample comprises about 1.75 M guanidine hydrochloride, about 0.5% N-acetyl-L-cysteine, about 12.5 mM sodium citrate, and about 1.25% Tween-20, and has a pH of about 3.2.

A nonlimiting exemplary commercial preservative is PreservCyt (Hologic, Bedford, Mass.).

4.2.3.2. Exemplary Cell Enrichment

In some embodiments, urothelial cells are enriched by centrifugation. In some such embodiments, the cell pellet is resuspended in the supernatant and/or a preservative. Resuspension of the cell pellet can be used to adjust the concentration of cells in solution. The resuspended cell pellet may be used (for example, with lysis) in the methods described herein, or may be subject to an additional enrichment step, such as filtration.

In some embodiments, urothelial cells are enriched by filtration. Nonlimiting exemplary filter pore sizes that may be suitable for capturing urothelial cells include 0.8 µm, 2 µm, 8 µm, and 10 µm. In some embodiments, a filter pore size is selected that allows pass-through or red blood cells and/or white blood cells, while retaining most urothelial cells. In some embodiments, a filter is located within a GeneXpert cartridge designed for carrying out a bladder cancer diagnostic assay described herein.

4.2.3.3. Exemplary mRNA Preparation

Target RNA can be prepared by any appropriate method. Total RNA can be isolated by any method, including, but not limited to, the protocols set forth in Wilkinson, M. (1988) Nucl. Acids Res. 16(22):10,933; and Wilkinson, M. (1988) Nucl. Acids Res. 16(22): 10,934, or by using commercially-available kits or reagents, such as the TRIzol® reagent (Invitrogen), Total RNA Extraction Kit (iNtRON Biotechnology), Total RNA Purification Kit (Norgen Biotek Corp.), RNAqueous™ (Ambion), MagMAX™ (Ambion), RecoverAll™ (Ambion), RNeasy (Qiagen), etc.

In some embodiments, RNA levels are measured in a sample in which RNA has not first been purified from the cells. In some such embodiments, the cells are subject to a lysis step to release the RNA. Nonlimiting exemplary lysis methods include sonication (for example, for 2-15 seconds, 8-18 µm at 36 kHz); chemical lysis, for example, using a detergent; and various commercially available lysis reagents (such as Rneasy lysis buffer, Qiagen). In some embodiments, RNA levels are measured in a sample in which RNA has been isolated.

In some embodiments, RNA is modified before a target RNA, such as AR, UPK1B, CRH, IGF2, KRT20 or ANXA10 mRNA, is detected. In some embodiments, all of the RNA in the sample is modified. In some embodiments, just the particular target RNAs to be analyzed are modified, e.g., in a sequence-specific manner. In some embodiments, RNA is reverse transcribed. In some such embodiments, RNA is reverse transcribed using MMLV reverse transcriptase. Nonlimiting exemplary conditions for reverse transcribing RNA using MMLV reverse transcriptase include incubation from 5 to 20 minutes at 40° C. to 50° C.

When a target RNA is reverse transcribed, a DNA complement of the target RNA is formed. In some embodiments, the complement of a target RNA is detected rather than a target RNA itself (or a DNA copy of the RNA itself). Thus, when the methods discussed herein indicate that a target RNA is detected, or the level of a target RNA is determined, such detection or determination may be carried out on a complement of a target RNA instead of, or in addition to, the target RNA itself. In some embodiments, when the complement of a target RNA is detected rather than the target RNA, a polynucleotide for detection is used that is complementary to the complement of the target RNA. In some such embodiments, a polynucleotide for detection comprises at least a portion that is identical in sequence to the target RNA, although it may contain thymidine in place of uridine, and/or comprise other modified nucleotides.

4.2.4. Exemplary Analytical Methods

As described above, methods are presented for detecting bladder cancer. The methods comprise detecting a panel of bladder cancer markers comprises AR and/or UPK1B, and optionally, at least one marker selected from CRH, IGF2, KRT20 and ANXA10. In some embodiments, the method further comprises detecting at least one endogenous control and/or at least one exogenous control. In some embodiments, detection of an elevated level of at least one, at least two, at least three, at least four, at least five, or six bladder cancer markers indicates the presence of bladder cancer. In some embodiments, the bladder cancer is low grade bladder cancer. In some embodiments, the bladder cancer is high grade bladder cancer. In some embodiments, the bladder cancer is a recurrence of bladder cancer in a patient with a history of bladder cancer.

Any analytical procedure capable of permitting specific and quantifiable (or semi-quantifiable) detection of a target RNA, such as AR, UPK1B, CRH, IGF2, KRT20 and ANXA10 mRNAs, may be used in the methods herein presented. Such analytical procedures include, but are not limited to, RT-PCR methods, and other methods known to those skilled in the art.

In some embodiments, the method of detecting a target RNA, such as AR, UPK1B, CRH, IGF2, KRT20 or ANXA10 mRNA, comprises amplifying cDNA complementary to the target RNA. Such amplification can be accomplished by any method. Exemplary methods include, but are not limited to, real time PCR, endpoint PCR, and amplification using T7 polymerase from a T7 promoter annealed to a cDNA, such as provided by the SenseAmp Plus™ Kit available at Implen, Germany.

When a target RNA or a cDNA complementary to a target RNA is amplified, in some embodiments, a DNA amplicon of the target RNA is formed. A DNA amplicon may be single stranded or double-stranded. In some embodiments, when a DNA amplicon is single-stranded, the sequence of the DNA amplicon is related to the target RNA in either the sense or antisense orientation. In some embodiments, a DNA amplicon of a target RNA is detected rather than the target RNA itself. Thus, when the methods discussed herein indicate that a target RNA is detected, or the level of a target RNA is determined, such detection or determination may be carried out on a DNA amplicon of the target RNA instead of, or in addition to, the target RNA itself. In some embodiments, when the DNA amplicon of the target RNA is detected rather than the target RNA, a polynucleotide for detection is used that is complementary to the complement of the target RNA. In some embodiments, when the DNA amplicon of the target RNA is detected rather than the target RNA, a polynucleotide for detection is used that is complementary to the target RNA. Further, in some embodiments, multiple polynucleotides for detection may be used, and some polynucleotides may be complementary to the target RNA and some polynucleotides may be complementary to the complement of the target RNA.

In some embodiments, the method of detecting one or more target RNAs, such as AR and/or UPK1B mRNA, and optionally, at least one mRNA selected from CRH, IGF2, KRT20 or ANXA10, comprises RT-PCR, as described below. In some embodiments, detecting one or more target RNAs comprises real-time monitoring of an RT-PCR reaction, which can be accomplished by any method. Such methods include, but are not limited to, the use of TaqMan®, Molecular beacon, or Scorpion probes (i.e., energy transfer (ET) probes, such as FRET probes) and the use of intercalating dyes, such as SYBR green, EvaGreen, thiazole orange, YO-PRO, TO-PRO, etc.

Nonlimiting exemplary conditions for amplifying cDNA that has been reverse transcribed from the target RNAs are as follows. An exemplary cycle comprises an initial denaturation at 90° C. to 100° C. for 2 to 5 minutes, followed by cycling that comprises denaturation at 90° C. to 100° C. for 1 to 10 seconds, annealing at 60° C. to 70° C. for 10 to 30 seconds, and extension at 60° C. to 75° C. for 10 to 40 seconds. In some embodiments, for the first cycle following the initial denaturation step, the cycle denaturation step is omitted. In some embodiments, Taq polymerase is used for amplification. In some embodiments, the cycle is carried out at least 10 times, at least 15 times, at least 20 times, at least 25 times, at least 30 times, at least 35 times, or at least 45 times. In some such embodiments, Taq is used with a hot start function. In some embodiments, the amplification reaction occurs in a GeneXpert cartridge, and amplification of the four bladder cancer marker target RNAs occurs in the same reaction. In some embodiments, detection of AR and/or UPK1B mRNA, and optionally, at least one mRNA selected from CRH, IGF2, KRT20 and ANXA10 occurs in less than 3 hours, less than 2.5 hours, or less than 2 hours, from initial denaturation through the last extension.

In some embodiments, detection of a target RNA comprises forming a complex comprising a polynucleotide that is complementary to a target RNA or to a complement thereof, and a nucleic acid selected from the target RNA, a DNA amplicon of the target RNA, and a complement of the target RNA. Thus, in some embodiments, the polynucleotide forms a complex with a target RNA. In some embodiments, the polynucleotide forms a complex with a complement of the target RNA, such as a cDNA that has been reverse transcribed from the target RNA. In some embodiments, the polynucleotide forms a complex with a DNA amplicon of the target RNA. When a double-stranded DNA amplicon is part of a complex, as used herein, the complex may comprise one or both strands of the DNA amplicon. Thus, in some embodiments, a complex comprises only one strand of the DNA amplicon. In some embodiments, a complex is a triplex and comprises the polynucleotide and both strands of the DNA amplicon. In some embodiments, the complex is formed by hybridization between the polynucleotide and the target RNA, complement of the target RNA, or DNA amplicon of the target RNA. The polynucleotide, in some embodiments, is a primer or probe.

In some embodiments, a method comprises detecting the complex. In some embodiments, the complex does not have to be associated at the time of detection. That is, in some embodiments, a complex is formed, the complex is then dissociated or destroyed in some manner, and components from the complex are detected. An example of such a system is a TaqMan® assay. In some embodiments, when the polynucleotide is a primer, detection of the complex may comprise amplification of the target RNA, a complement of the target RNA, or a DNA amplicon of a target RNA.

In some embodiments the analytical method used for detecting at least one target RNA in the methods set forth herein includes real-time quantitative RT-PCR. In some embodiments, the analytical method used for detecting at least one target RNA includes the use of a TaqMan® probe. The assay uses energy transfer ("ET"), such as fluorescence resonance energy transfer ("FRET"), to detect and quantitate the synthesized PCR product. Typically, the TaqMan® probe comprises a fluorescent dye molecule coupled to the 5'-end and a quencher molecule coupled to the 3'-end, such that the dye and the quencher are in close proximity, allowing the quencher to suppress the fluorescence signal of the dye via FRET. When the polymerase replicates the chimeric amplicon template to which the TaqMan® probe is bound, the 5'-nuclease of the polymerase cleaves the probe, decoupling the dye and the quencher so that the dye signal (such as fluorescence) is detected. Signal (such as fluorescence) increases with each RT-PCR cycle proportionally to the amount of probe that is cleaved.

In some embodiments, quantitation of the results of real-time RT-PCR assays is done by constructing a standard curve from a nucleic acid of known concentration and then extrapolating quantitative information for target RNAs of unknown concentration. In some embodiments, the nucleic acid used for generating a standard curve is an RNA (for example, an endogenous control, or an exogenous control). In some embodiments, the nucleic acid used for generating a standard curve is a purified double-stranded plasmid DNA or a single-stranded DNA generated in vitro.

In some embodiments, where the amplification efficiencies of the target nucleic acids and the endogenous reference are approximately equal, quantitation is accomplished by the comparative Ct (cycle threshold, e.g., the number of PCR cycles required for the fluorescence signal to rise above background) method. Ct values are inversely proportional to the amount of nucleic acid target in a sample. In some embodiments, Ct values of a target RNA can be compared with a control or calibrator, such an exogenous control RNA. In some embodiments, the Ct values of the exogenous control and the target RNA are normalized to an appropriate endogenous control. Nonlimiting exemplary endogenous controls are discussed herein.

In some embodiments, a threshold Ct (or a "cutoff Ct") value for a target RNA, below which bladder cancer is indicated, has previously been determined. In such embodiments, a control sample may not be assayed concurrently with the test sample. In some embodiments, as discussed herein, a ΔCt threshold value is determined, above which bladder cancer is indicated, has previously been determined.

In addition to the TaqMan® assays, other real-time RT-PCR chemistries useful for detecting and quantitating PCR products in the methods presented herein include, but are not limited to, Molecular Beacons, Scorpion probes and intercalating dyes, such as SYBR Green, EvaGreen, thiazole orange, YO-PRO, TO-PRO, etc., which are discussed below.

In various embodiments, real-time RT-PCR detection is utilized to detect, in a single multiplex reaction, all four bladder cancer markers of the panel described herein, and optionally, at least one endogenous control and/or at least one exogenous control. In some multiplex embodiments, a plurality of probes, such as TaqMan® probes, each specific for a different RNA target, is used. In some embodiments, each target RNA-specific probe is spectrally distinguishable from the other probes used in the same multiplex reaction.

In some embodiments, quantitation of real-time RT PCR products is accomplished using a dye that binds to double-stranded DNA products, such as SYBR Green, EvaGreen, thiazole orange, YO-PRO, TO-PRO, etc. In some embodiments, the assay is the QuantiTect SYBR Green PCR assay from Qiagen. In this assay, total RNA is first isolated from a sample. Total RNA is subsequently poly-adenylated at the 3'-end and reverse transcribed using a universal primer with poly-dT at the 5'-end. In some embodiments, a single reverse transcription reaction is sufficient to assay multiple target RNAs. Real-time RT-PCR is then accomplished using target RNA-specific primers and an miScript Universal Primer, which comprises a poly-dT sequence at the 5'-end. SYBR Green dye binds non-specifically to double-stranded DNA and upon excitation, emits light. In some embodiments, buffer conditions that promote highly-specific annealing of primers to the PCR template (e.g., available in the QuantiTect SYBR Green PCR Kit from Qiagen) can be used to avoid the formation of non-specific DNA duplexes and primer dimers that will bind SYBR Green and negatively affect quantitation. Thus, as PCR product accumulates, the signal from SYBR Green increases, allowing quantitation of specific products.

Real-time RT-PCR is performed using any RT-PCR instrumentation available in the art. Typically, instrumentation used in real-time RT-PCR data collection and analysis comprises a thermal cycler, optics for fluorescence excitation and emission collection, and optionally a computer and data acquisition and analysis software.

In some embodiments, the analytical method used in the methods described herein is a DASL® (cDNA-mediated Annealing, Selection, Extension, and Ligation) Assay. In some embodiments, total RNA is isolated from a sample to be analyzed by any method. Total RNA may then be polyadenylated (>18 A residues are added to the 3'-ends of the RNAs in the reaction mixture). The RNA is reverse transcribed using a biotin-labeled DNA primer that comprises from the 5' to the 3' end, a sequence that includes a PCR primer site and a poly-dT region that binds to the poly-dA tail of the sample RNA. The resulting biotinylated cDNA transcripts are then hybridized to a solid support via a biotin-streptavidin interaction and contacted with one or more target RNA-specific polynucleotides. The target RNA-specific polynucleotides comprise, from the 5'-end to the 3'-end, a region comprising a PCR primer site, region comprising an address sequence, and a target RNA-specific sequence.

In some DASL® embodiments, the target RNA-specific sequence comprises at least 8, at least 9, at least 10, at least 11, at least 12, at least 13, at least 14, at least 15, at least 16, at least 17, at least 18, at least 19 contiguous nucleotides having a sequence that is the same as, or complementary to, at least 8, at least 9, at least 10, at least 11, at least 12, at least 13, at least 14, at least 15, at least 16, at least 17, at least 18, at least 19 contiguous nucleotides of a bladder cancer marker target RNA, an endogenous control RNA, or an exogenous control RNA.

After hybridization, the target RNA-specific polynucleotide is extended, and the extended products are then eluted from the immobilized cDNA array. A second PCR reaction using a fluorescently-labeled universal primer generates a fluorescently-labeled DNA comprising the target RNA-specific sequence. The labeled PCR products are then hybridized to a microbead array for detection and quantitation.

In some embodiments, the analytical method used for detecting and quantifying the levels of the at least one target RNA in the methods described herein is a bead-based flow cytometric assay. See Lu J. et al. (2005) Nature 435:834-838, which is incorporated herein by reference in its entirety. An example of a bead-based flow cytometric assay is the xMAP® technology of Luminex, Inc. (See index.html in the technology folder of the luminexcorp website. In some embodiments, total RNA is isolated from a sample and is then labeled with biotin. The labeled RNA is then hybridized to target RNA-specific capture probes (e.g., FlexmiR™ products sold by Luminex, Inc. at index.html in the assays folder of the luminexciorp.com www server that are covalently bound to microbeads, each of which is labeled with 2 dyes having different fluorescence intensities. A streptavidin-bound reporter molecule (e.g., streptavidin-phycoerythrin, also known as "SAPE") is attached to the captured target RNA and the unique signal of each bead is read using flow cytometry. In some embodiments, the RNA sample is first polyadenylated, and is subsequently labeled with a biotinylated 3DNA™ dendrimer (i.e., a multiple-arm DNA with numerous biotin molecules bound thereto), using a bridging polynucleotide that is complementary to the 3'-end of the poly-dA tail of the sample RNA and to the 5'-end of the polynucleotide attached to the biotinylated dendrimer. The streptavidin-bound reporter molecule is then attached to the biotinylated dendrimer before analysis by flow cytometry. In some embodiments, biotin-labeled RNA is first exposed to SAPE, and the RNA/SAP complex is subsequently exposed to an anti-phycoerythrin antibody attached to a DNA dendrimer, which can be bound to as many as 900 biotin molecules. This allows multiple SAPE molecules to bind to the biotinylated dendrimer through the biotin-streptavidin interaction, thus increasing the signal from the assay.

In some embodiments, the analytical method used for detecting and quantifying the levels of the at least one target RNA in the methods described herein is by gel electrophoresis and detection with labeled probes (e.g., probes labeled with a radioactive or chemiluminescent label), such as by Northern blotting. In some embodiments, total RNA is isolated from the sample, and then is size-separated by SDS polyacrylamide gel electrophoresis. The separated RNA is then blotted onto a membrane and hybridized to radiolabeled complementary probes. In some embodiments, exemplary probes contain one or more affinity-enhancing nucleotide analogs as discussed below, such as locked nucleic acid ("LNA") analogs, which contain a bicyclic sugar moiety instead of deoxyribose or ribose sugars. See, e.g., Várallyay, E. et al. (2008) Nature Protocols 3(2):190-196, which is incorporated herein by reference in its entirety.

In some embodiments, detection and quantification of one or more target RNAs is accomplished using microfluidic devices and single-molecule detection. In some embodiments, target RNAs in a sample of isolated total RNA are hybridized to two probes, one which is complementary to nucleic acids at the 5'-end of the target RNA and the second which is complementary to the 3'-end of the target RNA. Each probe comprises, in some embodiments, one or more affinity-enhancing nucleotide analogs, such as LNA nucleotide analogs and each is labeled with a different fluorescent dye having different fluorescence emission spectra (i.e., detectably different dyes). The sample is then flowed through a microfluidic capillary in which multiple lasers excite the fluorescent probes, such that a unique coincident burst of photons identifies a particular target RNA, and the number of particular unique coincident bursts of photons can be counted to quantify the amount of the target RNA in the sample. In some alternative embodiments, a target RNA-specific probe can be labeled with 3 or more distinct labels selected from, e.g., fluorophores, electron spin labels, etc., and then hybridized to an RNA sample.

Optionally, the sample RNA is modified before hybridization. The target RNA/probe duplex is then passed through channels in a microfluidic device and that comprise detectors that record the unique signal of the 3 labels. In this way, individual molecules are detected by their unique signal and counted. See U.S. Pat. Nos. 7,402,422 and 7,351,538 to Fuchs et al., U.S. Genomics, Inc., each of which is incorporated herein by reference in its entirety.

4.2.5. Exemplary Automation and Systems

In some embodiments, gene expression is detected using an automated sample handling and/or analysis platform. In some embodiments, commercially available automated analysis platforms are utilized. For example, in some embodiments, the GeneXpert® system (Cepheid, Sunnyvale, Calif.) is utilized.

The present invention is illustrated for use with the GeneXpert system. Exemplary sample preparation and analysis methods are described below. However, the present invention is not limited to a particular detection method or analysis platform. One of skill in the art recognizes that any number of platforms and methods may be utilized.

The GeneXpert® utilizes a self-contained, single use cartridge. Sample extraction, amplification, and detection may all carried out within this self-contained "laboratory in a cartridge." (See e.g., U.S. Pat. Nos. 5,958,349, 6,403,037, 6,440,725, 6,783,736, 6,818,185; each of which is herein incorporated by reference in its entirety.)

Components of the cartridge include, but are not limited to, processing chambers containing reagents, filters, and capture technologies useful to extract, purify, and amplify target nucleic acids. A valve enables fluid transfer from chamber to chamber and contain nucleic acids lysis and filtration components. An optical window enables real-time optical detection. A reaction tube enables very rapid thermal cycling.

In some embodiments, the GenXpert® system includes a plurality of modules for scalability. Each module includes a plurality of cartridges, along with sample handling and analysis components.

In some embodiments, the GeneXpert® sample preparation method utilizes filtration in order to capture and concentrate cells from urine. In some embodiments, a filter pore size of 0.8 μm is utilized. This size facilitates capture of all cells in urine. In other embodiments, pore sizes of 0.5 to 10 μm, 0.5 to 5 μm, 0.8 to 10 μm, 0.8 to 5 μm, 0.8 to 2 μm, 2 to 5 μm, 2 to 10 μm, 2 to 8 μm, 5 to 8 μm, or 5 to 10 μm are utilized. Certain filters (such as 5 μm, 8 μm, and 10 μm) allow the removal of most red and white blood cells from the sample while capturing the larger urothelial cells, which are the assay target cells. In some embodiments, this sample preparation method improves assay specificity by removing white blood cells that may be present due to infection or inflammation. In some instances, sample preparation methods such as centrifugation of whole urine followed by RNA isolation from the urine pellet do not allow for removal of white blood cells. In some embodiments, the efficiency of cell capture by filtration is higher compared to centrifugation, and may provide more consistent results.

After the cells from the urine are captured on the filter, in some embodiments, they are washed and then lysed using sonication (2-15 seconds, 8-16 μm at 36 kHz). The cell lysate is then collected and used to reconstitute the RT-PCR reagents, which are present in the cartridge as lyophilized particles.

In some embodiments, RT-PCR is used to amplify and analyze the presence or expression levels of the bladder cancer markers. In some embodiments, the reverse transcription uses MMLV RT enzyme and an incubation of 5 to 20 minutes at 40° C. to 50° C. In some embodiments, the PCR uses Taq polymerase with hot start function, such as AptaTaq (Roche). In some embodiments, the initial denaturation is at 90° C. to 100° C. for 2 to 5 minutes; the cycling denaturation temperature is 90° C. to 100° C. for 1 to 10 seconds; the cycling anneal temperature is 60° C. to 70° C. for 10 to 30 seconds; and the cycling extend temperature is 60° C. to 75° C. for 10 to 40 seconds; and up to 50 cycles are performed.

The present invention is not limited to particular primer and/or probe sequences. Exemplary amplification primers and detection probes are described in the Examples.

In some embodiments, an off-line centrifugation is used to improve assay results with samples with low cellular content. The sample, with or without the preservative added, is centrifuged and the supernatant removed. The pellet is then resuspended in a smaller volume of either supernatant or the preservative. The resuspended pellet is then added to a GeneXpert® cartridge as previously described.

4.2.6. Exemplary Data Analysis

In some embodiments, a computer-based analysis program is used to translate the raw data generated by the detection assay (e.g., the expression level of the bladder cancer markers described herein) into data of predictive value for a clinician. The clinician can access the predictive data using any suitable means. Thus, in some embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., expression level of the bladder cancer markers described herein or diagnosis of bladder cancer) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

4.2.7. Exemplary Polynucleotides

In some embodiments, polynucleotides are provided. In some embodiments, synthetic polynucleotides are provided. Synthetic polynucleotides, as used herein, refer to polynucleotides that have been synthesized in vitro either chemically or enzymatically. Chemical synthesis of polynucleotides includes, but is not limited to, synthesis using polynucleotide synthesizers, such as OligoPilot (GE Healthcare), ABI 3900 DNA Synthesizer (Applied Biosystems), and the like. Enzymatic synthesis includes, but is not limited, to producing polynucleotides by enzymatic amplification, e.g., PCR. A polynucleotide may comprise one or more nucleotide analogs (i.e., modified nucleotides) discussed herein.

In some embodiments, a polynucleotide is provided that comprises a region that is identical to, or complementary to, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of a sequence selected from AR, UPK1B, CRH, IGF2, KRT20, and ANXA10 mRNA. In some embodiments, a polynucleotide is provided that comprises a region that is identical to, or complementary to, a span of 6 to 100, 8 to 100, 8 to 75, 8 to 50, 8 to 40, or 8 to 30 contiguous nucleotides of a sequence selected from AR, UPK1B, CRH, IGF2, KRT20, and ANXA10 mRNA. Nonlimiting exemplary polynucleotides are shown in Tables 1 and 6.

In various embodiments, a polynucleotide comprises fewer than 500, fewer than 300, fewer than 200, fewer than 150, fewer than 100, fewer than 75, fewer than 50, fewer than 40, or fewer than 30 nucleotides. In various embodiments, a polynucleotide is between 6 and 200, between 8 and 200, between 8 and 150, between 8 and 100, between 8 and 75, between 8 and 50, between 8 and 40, or between 8 and 30 nucleotides long.

In some embodiments, the polynucleotide is a primer. In some embodiments, the primer is labeled with a detectable moiety. In some embodiments, a primer is not labeled. A primer, as used herein, is a polynucleotide that is capable of specifically hybridizing to a target RNA or to a cDNA reverse transcribed from the target RNA or to an amplicon that has been amplified from a target RNA or a cDNA (collectively referred to as "template"), and, in the presence of the template, a polymerase and suitable buffers and reagents, can be extended to form a primer extension product.

In some embodiments, the polynucleotide is a probe. In some embodiments, the probe is labeled with a detectable moiety. A detectable moiety, as used herein, includes both directly detectable moieties, such as fluorescent dyes, and indirectly detectable moieties, such as members of binding pairs. When the detectable moiety is a member of a binding pair, in some embodiments, the probe can be detectable by incubating the probe with a detectable label bound to the second member of the binding pair. In some embodiments, a probe is not labeled, such as when a probe is a capture probe, e.g., on a microarray or bead. In some embodiments, a probe is not extendable, e.g., by a polymerase. In other embodiments, a probe is extendable.

In some embodiments, the polynucleotide is a FRET probe that in some embodiments is labeled at the 5'-end with a fluorescent dye (donor) and at the 3'-end with a quencher (acceptor), a chemical group that absorbs (i.e., suppresses) fluorescence emission from the dye when the groups are in close proximity (i.e., attached to the same probe). In other embodiments, the dye and quencher are not at the ends of the FRET probe. Thus, in some embodiments, the emission spectrum of the dye should overlap considerably with the absorption spectrum of the quencher.

4.2.7.1. Exemplary Polynucleotide Modifications

In some embodiments, the methods of detecting at least one target RNA described herein employ one or more polynucleotides that have been modified, such as polynucleotides comprising one or more affinity-enhancing nucleotide analogs. Modified polynucleotides useful in the methods described herein include primers for reverse transcription, PCR amplification primers, and probes. In some embodiments, the incorporation of affinity-enhancing nucleotides increases the binding affinity and specificity of a polynucleotide for its target nucleic acid as compared to polynucleotides that contain only deoxyribonucleotides, and allows for the use of shorter polynucleotides or for shorter regions of complementarity between the polynucleotide and the target nucleic acid.

In some embodiments, affinity-enhancing nucleotide analogs include nucleotides comprising one or more base modifications, sugar modifications and/or backbone modifications.

In some embodiments, modified bases for use in affinity-enhancing nucleotide analogs include 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine.

In some embodiments, affinity-enhancing nucleotide analogs include nucleotides having modified sugars such as 2'-substituted sugars, such as 2'-O-alkyl-ribose sugars, 2'-amino-deoxyribose sugars, 2'-fluoro-deoxyribose sugars, 2'-fluoro-arabinose sugars, and 2'-O-methoxyethyl-ribose (2'MOE) sugars. In some embodiments, modified sugars are arabinose sugars, or d-arabino-hexitol sugars.

In some embodiments, affinity-enhancing nucleotide analogs include backbone modifications such as the use of peptide nucleic acids (PNA; e.g., an oligomer including nucleobases linked together by an amino acid backbone). Other backbone modifications include phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof.

In some embodiments, a polynucleotide includes at least one affinity-enhancing nucleotide analog that has a modified base, at least nucleotide (which may be the same nucleotide) that has a modified sugar, and/or at least one internucleotide linkage that is non-naturally occurring.

In some embodiments, an affinity-enhancing nucleotide analog contains a locked nucleic acid ("LNA") sugar, which is a bicyclic sugar. In some embodiments, a polynucleotide for use in the methods described herein comprises one or more nucleotides having an LNA sugar. In some embodiments, a polynucleotide contains one or more regions consisting of nucleotides with LNA sugars. In other embodiments, a polynucleotide contains nucleotides with LNA sugars interspersed with deoxyribonucleotides. See, e.g., Frieden, M. et al. (2008) Curr. Pharm. Des. 14(11):1138-1142.

4.2.7.2. Exemplary Primers

In some embodiments, a primer is provided. In some embodiments, a primer is identical to, or complementary to, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of a sequence selected from AR, UPK1B, CRH, IGF2, KRT20, and ANXA10 mRNA. In some embodiments, a primer is provided that comprises a region that is identical to, or complementary to, a span of 6 to 100, 8 to 100, 8 to 75, 8 to 50, 8 to 40, or 8 to 30 contiguous nucleotides of a sequence selected from AR, UPK1B, CRH, IGF2, KRT20, and ANXA10 mRNA. Nonlimiting exemplary primers are shown in Tables 1 and 6. In some embodiments, a primer may also comprise portions or regions that are not identical or complementary to the target RNA. In some embodiments, a region of a primer that is identical or complementary to a target RNA is contiguous, such that any region of a primer that is not identical or complementary to the target RNA does not disrupt the identical or complementary region.

In some embodiments, a primer comprises a portion that is identically present in a target RNA. In some such embodiments, a primer that comprises a region that is identically present in the target RNA is capable of selectively hybridizing to a cDNA that has been reverse transcribed from the RNA, or to an amplicon that has been produced by amplification of the target RNA or cDNA. In some embodiments, the primer is complementary to a sufficient portion of the cDNA or amplicon such that it selectively hybridizes to the cDNA or amplicon under the conditions of the particular assay being used.

As used herein, "selectively hybridize" means that a polynucleotide, such as a primer or probe, will hybridize to a particular nucleic acid in a sample with at least 5-fold greater affinity than it will hybridize to another nucleic acid present in the same sample that has a different nucleotide sequence in the hybridizing region. Exemplary hybridization conditions are discussed herein, for example, in the context of a reverse transcription reaction or a PCR amplification reaction. In some embodiments, a polynucleotide will hybridize to a particular nucleic acid in a sample with at least 10-fold greater affinity than it will hybridize to another nucleic acid present in the same sample that has a different nucleotide sequence in the hybridizing region.

In some embodiments, a primer is used to reverse transcribe a target RNA, for example, as discussed herein. In some embodiments, a primer is used to amplify a target RNA or a cDNA reverse transcribed therefrom. Such amplification, in some embodiments, is quantitative PCR, for example, as discussed herein. In some embodiments, a primer comprises a detectable moiety.

In some embodiments, primer pairs are provided. Such primer pairs are designed to amplify a portion of a target mRNA, such as AR, UPK1B, CRH, IGF2, KRT20, or ANXA10 mRNA, or an endogenous control RNA, or an exogenous control RNA. In some embodiments, a primer pair is designed to produce an amplicon that is 50 to 1500 nucleotides long, 50 to 1000 nucleotides long, 50 to 750 nucleotides long, 50 to 500 nucleotides long, 50 to 400 nucleotides long, 50 to 300 nucleotides long, 50 to 200 nucleotides long, 50 to 150 nucleotides long, or 50 to 100 nucleotides long. Nonlimiting exemplary primer pairs are shown in Tables 1 and 6. In some embodiments, a primer pair is designed that spans an intron in the genomic sequence so that the mRNA, without the intron, is more preferably amplified than the genomic sequence. By "spans an intron" is meant that one primer of the primer pair is complementary to a sequence in the mRNA or a cDNA reverse transcribed from the mRNA that is at least partially located 5' to an intron in the genomic sequence and one primer of the primer pair is complementary to a sequence in the mRNA or a cDNA reverse transcribed from the mRNA that is at least partially located 3' to the same intron in the genomic sequence. In some embodiments, one primer of the primer pair is complementary to a sequence in the mRNA or a cDNA reverse transcribed from the mRNA that is located 5' to an intron in the genomic sequence and one primer of the primer pair is complementary to a sequence in the mRNA or a cDNA reverse transcribed from the mRNA that is located 3' to the same intron in the genomic sequence. In some embodiments, one of the primers in the primer pair may be complementary to a sequence in the mRNA or a cDNA reverse transcribed from the mRNA that is spliced together when the intron is removed such that the contiguous complementary sequence is not found in the genomic sequence. A primer pair comprising such a primer is still considered to span an intron.

4.2.7.3. Exemplary Probes

In various embodiments, methods of detecting the presence of bladder cancer comprise hybridizing nucleic acids of a sample with a probe. In some embodiments, the probe comprises a portion that is complementary to a target RNA, such as AR, UPK1B, CRH, IGF2, KRT20 or ANXA10 mRNA. In some embodiments, the probe comprises a portion that is identically present in the target RNA. In some such embodiments, a probe that is complementary to a target RNA is complementary to a sufficient portion of the target RNA such that it selectively hybridizes to the target RNA under the conditions of the particular assay being used. In some embodiments, a probe that is complementary to a target RNA comprises a region that is complementary to at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of the target RNA, such as CRH, IGF2, KRT20 or ANXA10 mRNA. Nonlimiting exemplary probes are shown in Tables 1 and 6. A probe that is complementary to a target RNA may also comprise portions or regions that are not complementary to the target RNA. In some embodiments, a region of a probe that is complementary to a target RNA is contiguous, such that any region of a probe that is not complementary to the target RNA does not disrupt the complementary region.

In some embodiments, the probe comprises a portion that is identically present in the target RNA, such as AR, UPK1B, CRH, IGF2, KRT20 or ANXA10 mRNA. In some such embodiments, a probe that comprises a region that is identically present in the target RNA is capable of selectively hybridizing to a cDNA that has been reverse transcribed from the RNA, or to an amplicon that has been produced by amplification of the target RNA or cDNA. In some embodiments, the probe is complementary to a sufficient portion of the cDNA or amplicon such that it selectively hybridizes to the cDNA or amplicon under the conditions of the particular assay being used. In some embodiments, a probe that is complementary to a cDNA or amplicon comprises a region that is complementary to at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of the cDNA or amplicon. A probe that is complementary to a cDNA or amplicon may also comprise portions or regions that are not complementary to the cDNA or amplicon. In some embodiments, a region of a probe that is complementary to a cDNA or amplicon is contiguous, such that any region of a probe that is not complementary to the cDNA or amplicon does not disrupt the complementary region.

In some embodiments, the method of detectably quantifying one or more target RNAs comprises: (a) reverse transcribing a target RNA to produce a cDNA that is complementary to the target RNA; (b) amplifying the cDNA from (a); and (c) detecting the amount of a target RNA using real time RT-PCR and a detection probe (which may be simultaneous with the amplification step (b)).

As described above, in some embodiments, real time RT-PCR detection may be performed using a FRET probe, which includes, but is not limited to, a TaqMan® probe, a Molecular beacon probe and a Scorpion probe. In some embodiments, the real time RT-PCR detection and quantification is performed with a TaqMan® probe, i.e., a linear probe that typically has a fluorescent dye covalently bound at one end of the DNA and a quencher molecule covalently bound at the other end of the DNA. The FRET probe comprises a sequence that is complementary to a region of the cDNA such that, when the FRET probe is hybridized to the cDNA, the dye fluorescence is quenched, and when the probe is digested during amplification of the cDNA, the dye is released from the probe and produces a fluorescence signal. In such embodiments, the amount of target RNA in the sample is proportional to the amount of fluorescence measured during cDNA amplification.

The TaqMan® probe typically comprises a region of contiguous nucleotides having a sequence that is complementary to a region of a target RNA or its complementary cDNA that is reverse transcribed from the target RNA template (i.e., the sequence of the probe region is complementary to or identically present in the target RNA to be detected) such that the probe is specifically hybridizable to the resulting PCR amplicon. In some embodiments, the probe comprises a region of at least 6 contiguous nucleotides having a sequence that is fully complementary to or identically present in a region of a cDNA that has been reverse transcribed from a target RNA template, such as comprising a region of at least 8 contiguous nucleotides, at least 10 contiguous nucleotides, at least 12 contiguous nucleotides, at least 14 contiguous nucleotides, or at least 16 contiguous nucleotides having a sequence that is complementary to or identically present in a region of a cDNA reverse transcribed from a target RNA to be detected.

In some embodiments, the region of the cDNA that has a sequence that is complementary to the TaqMan® probe sequence is at or near the center of the cDNA molecule. In some embodiments, there are independently at least 2 nucleotides, such as at least 3 nucleotides, such as at least 4 nucleotides, such as at least 5 nucleotides of the cDNA at the 5'-end and at the 3'-end of the region of complementarity.

In some embodiments, Molecular Beacons can be used to detect and quantitate PCR products. Like TaqMan® probes, Molecular Beacons use FRET to detect and quantitate a PCR product via a probe having a fluorescent dye and a quencher attached at the ends of the probe. Unlike TaqMan® probes, Molecular Beacons remain intact during the PCR cycles. Molecular Beacon probes form a stem-loop structure when free in solution, thereby allowing the dye and quencher to be in close enough proximity to cause fluorescence quenching. When the Molecular Beacon hybridizes to a target, the stem-loop structure is abolished so that the dye and the quencher become separated in space and the dye fluoresces. Molecular Beacons are available, e.g., from Gene Link™ (see mbintro.asp in the newsite/products folder of the genelink.com www server).

In some embodiments, Scorpion probes can be used as both sequence-specific primers and for PCR product detection and quantitation. Like Molecular Beacons, Scorpion probes form a stem-loop structure when not hybridized to a target nucleic acid. However, unlike Molecular Beacons, a Scorpion probe achieves both sequence-specific priming and PCR product detection. A fluorescent dye molecule is attached to the 5'-end of the Scorpion probe, and a quencher is attached to the 3'-end. The 3' portion of the probe is complementary to the extension product of the PCR primer, and this complementary portion is linked to the 5'-end of the probe by a non-amplifiable moiety. After the Scorpion primer is extended, the target-specific sequence of the probe binds to its complement within the extended amplicon, thus opening up the stem-loop structure and allowing the dye on the 5'-end to fluoresce and generate a signal. Scorpion probes are available from, e.g., Premier Biosoft International (see Scorpion.html in the tech notes folder of the premiebiosoft.com www server).

In some embodiments, labels that can be used on the FRET probes include colorimetric and fluorescent dyes such as Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB.

Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Examples of dye/quencher pairs (i.e., donor/acceptor pairs) include, but are not limited to, fluorescein/tetramethylrhodamine; IAEDANS/fluorescein; EDANS/dabcyl; fluorescein/fluorescein; BODIPY FL/BODIPY FL; fluorescein/QSY 7 or QSY 9 dyes. When the donor and acceptor are the same, FRET may be detected, in some embodiments, by fluorescence depolarization. Certain specific examples of dye/quencher pairs (i.e., donor/acceptor pairs) include, but are not limited to, Alexa Fluor 350/Alexa Fluor488; Alexa Fluor 488/Alexa Fluor 546; Alexa Fluor 488/Alexa Fluor 555; Alexa Fluor 488/Alexa Fluor 568; Alexa Fluor 488/Alexa Fluor 594; Alexa Fluor 488/Alexa Fluor 647; Alexa Fluor 546/Alexa Fluor 568; Alexa Fluor 546/Alexa Fluor 594; Alexa Fluor 546/Alexa Fluor 647; Alexa Fluor 555/Alexa Fluor 594; Alexa Fluor 555/Alexa Fluor 647; Alexa Fluor 568/Alexa Fluor 647; Alexa Fluor 594/Alexa Fluor 647; Alexa Fluor 350/QSY35; Alexa Fluor 350/dabcyl; Alexa Fluor 488/QSY 35; Alexa Fluor 488/dabcyl; Alexa Fluor 488/QSY 7 or QSY 9; Alexa Fluor 555/QSY 7 or QSY9; Alexa Fluor 568/QSY 7 or QSY 9; Alexa Fluor 568/QSY 21; Alexa Fluor 594/QSY 21; and Alexa Fluor 647/QSY 21. In some instances, the same quencher may be used for multiple dyes, for example, a broad spectrum quencher, such as an Iowa Black® quencher (Integrated DNA Technologies, Coralville, Iowa) or a Black Hole Quencher™ (BHQ™; Sigma-Aldrich, St. Louis, Mo.).

In some embodiments, for example, in a multiplex reaction in which two or more moieties (such as amplicons) are detected simultaneously, each probe comprises a detectably different dye such that the dyes may be distinguished when detected simultaneously in the same reaction. One skilled in the art can select a set of detectably different dyes for use in a multiplex reaction.

Specific examples of fluorescently labeled ribonucleotides useful in the preparation of RT-PCR probes for use in some embodiments of the methods described herein are available from Molecular Probes (Invitrogen), and these include, Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences (GE Healthcare), such as Cy3-UTP and Cy5-UTP.

Examples of fluorescently labeled deoxyribonucleotides useful in the preparation of RT-PCR probes for use in the methods described herein include Dinitrophenyl (DNP)-1'-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP. Fluorescently labeled nucleotides are commercially available and can be purchased from, e.g., Invitrogen.

In some embodiments, dyes and other moieties, such as quenchers, are introduced into polynucleotide used in the methods described herein, such as FRET probes, via modified nucleotides. A "modified nucleotide" refers to a nucleotide that has been chemically modified, but still functions as a nucleotide. In some embodiments, the modified nucleotide has a chemical moiety, such as a dye or quencher, covalently attached, and can be introduced into a polynucleotide, for example, by way of solid phase synthesis of the polynucleotide. In other embodiments, the modified nucleotide includes one or more reactive groups that can react with a dye or quencher before, during, or after incorporation of the modified nucleotide into the nucleic acid. In specific embodiments, the modified nucleotide is an amine-modified nucleotide, i.e., a nucleotide that has been modified to have a reactive amine group. In some embodiments, the modified nucleotide comprises a modified base moiety, such as uridine, adenosine, guanosine, and/or cytosine. In specific embodiments, the amine-modified nucleotide is selected from 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP. In some embodiments, nucleotides with different nucleobase moieties are similarly modified, for example, 5-(3-aminoallyl)-GTP instead of 5-(3-aminoallyl)-UTP. Many amine modified nucleotides are commercially available from, e.g., Applied Biosystems, Sigma, Jena Bioscience and TriLink.

Exemplary detectable moieties also include, but are not limited to, members of binding pairs. In some such embodiments, a first member of a binding pair is linked to a polynucleotide. The second member of the binding pair is linked to a detectable label, such as a fluorescent label. When the polynucleotide linked to the first member of the binding pair is incubated with the second member of the binding pair linked to the detectable label, the first and second members of the binding pair associate and the polynucleotide can be detected. Exemplary binding pairs include, but are not limited to, biotin and streptavidin, antibodies and antigens, etc.

In some embodiments, multiple target RNAs are detected in a single multiplex reaction. In some such embodiments, each probe that is targeted to a unique cDNA is spectrally distinguishable when released from the probe. Thus, each target RNA is detected by a unique fluorescence signal.

One skilled in the art can select a suitable detection method for a selected assay, e.g., a real-time RT-PCR assay. The selected detection method need not be a method described above, and may be any method.

4.3. Exemplary Compositions and Kits

In another aspect, compositions are provided. In some embodiments, compositions are provided for use in the methods described herein.

In some embodiments, compositions are provided that comprise at least one target RNA-specific primer. The term "target RNA-specific primer" encompasses primers that have a region of contiguous nucleotides having a sequence that is (i) identically present in a target RNA, such as AR, UPK1B, CRH, IGF2, KRT20, or ANXA10 mRNA, or (ii) complementary to the sequence of a region of contiguous nucleotides found in a target RNA, such as AR, UPK1B, CRH, IGF2, KRT20, or ANXA10 mRNA. In some embodiments, a composition is provided that comprises at least one pair of target RNA-specific primers. The term "pair of target RNA-specific primers" encompasses pairs of primers that are suitable for amplifying a defined region of a target RNA, such as AR, UPK1B, CRH, IGF2, KRT20, or ANXA10 mRNA. A pair of target RNA-specific primers typically comprises a first primer that comprises a sequence that is identical to the sequence of a region of a target RNA (although the primer will typically comprise DNA or modified nucleosides rather than RNA) and a second primer that comprises a sequence that is complementary to a region of a target RNA. A pair of primers is typically suitable for amplifying a region of a target mRNA that is 50 to 1500 nucleotides long, 50 to 1000 nucleotides long, 50 to 750 nucleotides long, 50 to 500 nucleotides long, 50 to 400 nucleotides long, 50 to 300 nucleotides long, 50 to 200 nucleotides long, 50 to 150 nucleotides long, or 50 to 100 nucleotides long. Nonlimiting exemplary primers, and pairs of primers, are shown in Tables 1 and 6.

In some embodiments, a composition comprises at least one, at least two, at least three, at least four, at least five, or six pairs of target RNA-specific primers, one pair for amplifying each of AR and/or UPK1B mRNA, and at least one mRNA selected from CRH, IGF2, KRT20, and ANXA10. In some embodiments, a composition additionally comprises a pair of target RNA-specific primers for amplifying an endogenous control RNA and/or one pair of target RNA-specific primers for amplifying an exogenous control RNA.

In some embodiments, a composition comprises at least one target RNA-specific probe. The term "target RNA-specific probe" encompasses probes that have a region of contiguous nucleotides having a sequence that is (i) identically present in a target RNA, such as such as AR, UPK1B, CRH, IGF2, KRT20, or ANXA10 mRNA, or (ii) complementary to the sequence of a region of contiguous nucleotides found in a target RNA, such as such as AR, UPK1B, CRH, IGF2, KRT20, or ANXA10 mRNA. Nonlimiting exemplary target-specific probes are shown in Tables 1 and 6.

In some embodiments, a composition (including a composition described above that comprises one or more pairs of target RNA-specific primers) comprises at least one, at least two, at least three, at least four, at least five, or six probes, one probe for detecting each of AR and/or UPK1B, and at least one mRNA selected from CRH, IGF2, KRT20, and ANXA10. In some embodiments, a composition additionally comprises a probe for detecting an endogenous control RNA and/or a probe for detecting an exogenous control RNA.

In some embodiments, a composition is an aqueous composition. In some embodiments, the aqueous composition comprises a buffering component, such as phosphate, tris, HEPES, etc., and/or additional components, as discussed below. In some embodiments, a composition is dry, for example, lyophilized, and suitable for reconstitution by addition of fluid. A dry composition may include one or more buffering components and/or additional components.

In some embodiments, a composition further comprises one or more additional components. Additional components include, but are not limited to, salts, such as NaCl, KCl, and $MgCl_2$; polymerases, including thermostable polymerases such as Taq; dNTPs; reverse transcriptases, such as MMLV reverse transcriptase; Rnase inhibitors; bovine serum albumin (BSA) and the like; reducing agents, such as β-mercaptoethanol; EDTA and the like; etc. One skilled in the art can select suitable composition components depending on the intended use of the composition.

In some embodiments, compositions are provided that comprise at least one polynucleotide for detecting at least one target RNA. In some embodiments, the polynucleotide is used as a primer for a reverse transcriptase reaction. In some embodiments, the polynucleotide is used as a primer for amplification. In some embodiments, the polynucleotide is used as a primer for RT-PCR. In some embodiments, the polynucleotide is used as a probe for detecting at least one target RNA. In some embodiments, the polynucleotide is detectably labeled. In some embodiments, the polynucleotide is a FRET probe. In some embodiments, the polynucleotide is a TaqMan® probe, a Molecular Beacon, or a Scorpion probe.

In some embodiments, a composition comprises at least one FRET probe having a sequence that is identically present in, or complementary to a region of, CRH, IGF2, KRT20, or ANXA10 mRNA. In some embodiments, a FRET probe is labeled with a donor/acceptor pair such that when the probe is digested during the PCR reaction, it produces a unique fluorescence emission that is associated with a specific target RNA. In some embodiments, when a composition comprises multiple FRET probes, each probe is labeled with a different donor/acceptor pair such that when the probe is digested during the PCR reaction, each one produces a unique fluorescence emission that is associated with a specific probe sequence and/or target RNA. In some embodiments, the sequence of the FRET probe is complementary to a target region of a target RNA. In other embodiments, the FRET probe has a sequence that comprises one or more base mismatches when compared to the sequence of the best-aligned target region of a target RNA.

In some embodiments, a composition comprises a FRET probe consisting of at least 8, at least 9, at least 10, at least 11, at least 13, at least 14, at least 15, at least 16, at least 17, at least 18, at least 19, at least 20, at least 21, at least 22, at least 23, at least 24, or at least 25 nucleotides, wherein at least a portion of the sequence is identically present in, or complementary to a region of, AR, UPK1B, CRH, IGF2, KRT20, or ANXA10 mRNA. In some embodiments, at least 8, at least 9, at least 10, at least 11, at least 13, at least 14, at least 15, at least 16, at least 17, at least 18, at least 19, at least 20, at least 21, at least 22, at least 23, at least 24, or at least 25 nucleotides of the FRET probe are identically present in, or complementary to a region of, AR, UPK1B, CRH, IGF2, KRT20, or ANXA10 mRNA. In some embodiments, the FRET probe has a sequence with one, two or three base mismatches when compared to the sequence or complement of AR, UPK1B, CRH, IGF2, KRT20, or ANXA10 mRNA.

In some embodiments, a kit comprises a polynucleotide discussed above. In some embodiments, a kit comprises at least one primer and/or probe discussed above. In some embodiments, a kit comprises at least one polymerase, such as a thermostable polymerase. In some embodiments, a kit comprises dNTPs. In some embodiments, kits for use in the real time RT-PCR methods described herein comprise one or more target RNA-specific FRET probes and/or one or more primers for reverse transcription of target RNAs and/or one or more primers for amplification of target RNAs or cDNAs reverse transcribed therefrom.

In some embodiments, one or more of the primers and/or probes is "linear". A "linear" primer refers to a polynucleotide that is a single stranded molecule, and typically does not comprise a short region of, for example, at least 3, 4 or 5 contiguous nucleotides, which are complementary to another region within the same polynucleotide such that the primer forms an internal duplex. In some embodiments, the primers for use in reverse transcription comprise a region of at least 4, such as at least 5, such as at least 6, such as at least 7 or more contiguous nucleotides at the 3'-end that has a sequence that is complementary to region of at least 4, such as at least 5, such as at least 6, such as at least 7 or more contiguous nucleotides at the 5'-end of a target RNA.

In some embodiments, a kit comprises one or more pairs of linear primers (a "forward primer" and a "reverse primer") for amplification of a cDNA reverse transcribed from a target RNA, such as AR, UPK1B, CRH, IGF2, KRT20, or ANXA10 mRNA. Accordingly, in some embodiments, a first primer comprises a region of at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 contiguous nucleotides having a sequence that is identical to the sequence of a region of at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 contiguous nucleotides at a first location in the mRNA. Furthermore, in some embodiments, a second primer comprises a region of at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 contiguous nucleotides having a sequence that is complementary to the sequence of a region of at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 contiguous nucleotides at a second location in the mRNA, such that a PCR reaction using the two primers results in an amplicon extending from the first location of the mRNA to the second location of the mRNA.

In some embodiments, the kit comprises at least two, at least three, or at least four sets of primers, each of which is for amplification of a cDNA that is reverse transcribed from a different target RNA, including AR, UPK1B, CRH, IGF2, KRT20, and ANXA10 mRNA. In some embodiments, the kit further comprises at least one set of primers for amplifying a control RNA, such as an endogenous control and/or an exogenous control.

In some embodiments, probes and/or primers for use in the compositions described herein comprise deoxyribonucleotides. In some embodiments, probes and/or primers for use in the compositions described herein comprise deoxyribonucleotides and one or more nucleotide analogs, such as LNA analogs or other duplex-stabilizing nucleotide analogs described above. In some embodiments, probes and/or primers for use in the compositions described herein comprise all nucleotide analogs. In some embodiments, the probes and/or primers comprise one or more duplex-stabilizing nucleotide analogs, such as LNA analogs, in the region of complementarity.

In some embodiments, the kits for use in real time RT-PCR methods described herein further comprise reagents for use in the reverse transcription and amplification reactions. In some embodiments, the kits comprise enzymes such as reverse transcriptase, and a heat stable DNA polymerase, such as Taq polymerase. In some embodiments, the kits further comprise deoxyribonucleotide triphosphates (dNTP) for use in reverse transcription and amplification. In further embodiments, the kits comprise buffers optimized for specific hybridization of the probes and primers.

The following examples are for illustration purposes only, and are not meant to be limiting in any way.

5. EXAMPLES

5.1. Example 1

Detection of High Grade and Low Grade Bladder Cancer

More than 30 mRNA markers and 20 microRNA markers were evaluated in both bladder tissue and urine samples to determine the most accurate panel for detection of bladder cancer. Based on results from over 200 urine samples using eight markers and the GeneXpert system (Cepheid, Sunnyvale, Calif.), a panel consisting of CRH, IGF2, KRT20, and ANXA10 mRNA markers (with or without at least one endogenous and/or at least one exogenous control) was selected.

Various reaction compositions were designed for use in the GeneXpert® system, for detecting various combinations of CRH, IGF2, KRT20, and ANXA10 mRNA. Table 1 shows the sequences of the primers and probes used to detect each of the target RNAs by quantitative RT-PCR in the various reaction compositions.

TABLE 1

Primer and probe sequences

| oligo name | target | sequence | SEQ ID NO | Reagent Formul. ("TSR") |
|---|---|---|---|---|
| ABLa3a4 PrmrFwd4 | ABL | GATCAACACTGCTTCTGATGGCAA | 8 | CL3, CL4, CL1 |
| ABLa3a4 PrmrRev1 | ABL | CCACCGTTGAATGATGATGAACCAA | 9 | CL3, CL4, CL1 |
| ABLa3a4 Probe1 | ABL | F4-CCTCCGAGAGCCGCTTCAAC-Q4 | 10 | CL3 |
| ABL probe F6 | ABL | F6-CCTCCGAGAGCCGCTTCAAC-Q6 | 11 | CL4 |
| ABL probe F1 | ABL | F1-CCTCCGAGAGCCGC (T-dabsyl) TCAAC-Q1 | 12 | CL1 |
| KRT20 For | KRT20 | TTGAAGAGCTGCGAAGTCAGAT | 13 | CL3, CL4 |
| KRT20 Rev | KRT20 | TGAAGTCCTCAGCAGCCAGTT | 14 | CL3, CL4 |
| KRT20 Probe (F3) | KRT20 | F3-TCAACTGCAAAATGCTCGGTGTGTCC-Q3 | 15 | CL3, CL4 |
| IGF2 For_4 | IGF2 | CGCGGCTTCTACTTCAGCAG | 16 | CL3, CL4 |
| IGF2 Rev_4 | IGF2 | GCGGAAACAGCACTCCTCAA | 17 | CL3, CL4 |
| IGF2 Probe_2 | IGF2 | F5-TGTGAGCCGTCGCAGCCGTG-Q5 | 18 | CL3, CL4 |
| CRH_For | CRH | ACCCGGCTCACCTGCGAA | 19 | CL3, CL4, CL1 |
| CRH_Rev | CRH | GGACTCCCGCGGACACAA | 20 | CL3, CL4, CL1 |
| CRH_probe 3 | CRH | F2-TCCTGGGAAGCGAGTGCCCCTAA-Q2 | 21 | CL3, CL1 |
| CRH_probe_F1 | CRH | F1-CCTGGGAAGCGAG (T-Dabsyl) GCCCCTAA-Q1 | 22 | CL4 |
| Armored RNA® Fwd | exogenous control | GGCTATTCTCCTCTTGGCAGAT | 23 | CL1 |
| Armored RNA® Rev | exogenous control | TGCTTGAGCTCCAGTCCCTAAG | 24 | CL1 |

TABLE 1-continued

Primer and probe sequences

| oligo name | target | sequence | SEQ ID NO | Reagent Formul. ("TSR") |
|---|---|---|---|---|
| Armored RNA ®_Probe | exogenous control | F6-AGCCGAGAAGGCGGAGTCTGGC-Q6 | 25 | CL1 |
| ANXA10-FW | ANXA10 | GTGAAACAAGTTTATGCAATCGATCAA | 26 | CL1 |
| ANXA10-RV3 | ANXA10 | GATTGAAATTGGGAGCTGGGAA | 27 | CL1 |
| ANXA10-F3 | ANXA10 | F3-TCATCCCTGAGGTTAACAATTACCATCAA-Q3 | 28 | CL1 |

F1 through F6 are detectably different dyes that can be detected and distinguished simultaneously in a multiplex reaction, and Q1 to Q6 are quenchers (in the present example, Q2, Q4, Q5, and Q6 are the same quencher).

The final primer and probe compositions of three different reaction compositions are shown in Table 2.

TABLE 2

Primers and probes in TSR CL3, CL4, and CL1

| Target | Label | Purpose | Final conc. Forw. Primer | Final conc. Rev primer | Final conc. Probe |
|---|---|---|---|---|---|
| TSR CL3 | | | | | |
| ABL | F4 | Normalization (endogenous control) | 400 nM | 400 nM | 150 nM |
| KRT20 | F3 | Bladder cancer marker | 400 nM | 400 nM | 75 nM |
| IGF2 | F5 | Bladder cancer marker | 400 nM | 400 nM | 200 nM |
| CRH | F2 | Bladder cancer marker | 400 nM | 400 nM | 200 nM |
| TSR CL4 | | | | | |
| ABL | F6 | Normalization (endogenous control) | 400 nM | 400 nM | 400 nM |
| KRT20 | F3 | Bladder cancer marker | 400 nM | 400 nM | 75 nM |
| IGF2 | F5 | Bladder cancer marker | 400 nM | 400 nM | 300 nM |
| CRH | F1 | Bladder cancer marker | 400 nM | 400 nM | 600 nM |
| TSR CL1 | | | | | |
| ABL | F1 | Normalization (endogenous control) | 400 nM | 400 nM | 600 nM |
| Armored RNA ® | F6 | Exogenous control | 400 nM | 400 nM | 400 nM |
| ANXA10 | F3 | Bladder cancer marker | 400 nM | 400 nM | 75 nM |
| CRH | F2 | Bladder cancer marker | 400 nM | 400 nM | 300 nM |

Each reaction contained 50-90 mM KCl, 3-5 mM $MgCl_2$, 400-825 µM dNTPs, 20 mM Tris, pH 8.5, 0.01% sodium azide, and 0.9 units/µl of Rnase inhibitor. MMLV reverse transcriptase (0.375 units/µl) and AptaTaq (0.25 units/µl; Roche) were used for reverse transcription and amplification, respectively. TSR CL1 included an Armored RNA® exogenous control (SEQ ID NO: 47; Asuragen, Austin, Tex.).

For each sample to be tested, 5 mL of voided urine was added to 5 mL preservative (3.5M guanidine HCl, 1% N-acetyl-L-cysteine, 25 mM sodium citrate, and 2.5% Tween-20, pH 3.2), preferably within 1 hour of sample collection. The preserved samples were transported on ice and stored at 4° C. Clinical information for each sample was provided by the collection sites. The number of red blood cells per millilitre was determined by microscopic evaluation.

Prior to use, the preserved urine was inverted three times to mix. 1.2 mL of preserved urine was loaded into a GeneXpert cartridge for analysis. The cartridge contained a 0.8 µm filter to capture urothelial cells. The captured cells were washed and lysed using sonication (2-15 seconds, 8-16 µm at 36 kHz) within the cartridge. The lysate was then used to reconstitute the reagents used for real-time RT-PCR (described above). The reaction cycle used was: 10 minutes at 45° C., followed by 2 minutes at 95° C., and then 45 cycles of (a) 5 seconds at 95° C., 20 seconds at 60° C., and 20 seconds at 72° C., using a GeneXpert® cartridge in a GeneXpert® system. Delta Ct (ΔCt) was calculated as Ct (ABL)−Ct (marker). The ΔCt cutoff was set as the ΔCt that gave at least 95% specificity with samples from patients not expected to have bladder cancer (data not shown). A ΔCt above the ΔCt cutoff for any one of the markers was considered a positive result, indicative of the presence of bladder cancer.

Some samples were also tested using UroVysion® (Abbott Laboratories, Abbott Park, Ill.). The results of that experiment are shown in Table 3 (high grade bladder cancer) and Table 4 (low grade bladder cancer). ΔCts above the threshold, indicating a positive result, are highlighted. Each of the three TSR lots, CL3, CL4, and CL1, detected 100% of high grade bladder cancer samples, as did UroVysion®.

For low grade bladder cancer, the detection rate was 37% (7/19), compared to only 16% (3/19) for UroVysion®.

TABLE 3

Detection of high grade bladder cancer

| | | | | | history | TSR lot CL3 | | | TSR lot CL4 | | | CIC TSR lot CL1 | | |
|---|---|---|---|---|---|---|---|---|---|---|---|---|---|---|
| Sample ID | stage | grade | UroVysion ® Result | cytology | of bladder cancer | CRH -10 | KRT20 2.2 | IGF2 -1 | KRT20 4 | IGF2 0.5 | CRH -5 | ANXA10 -0.5 | CRH -3 | GX result |
| 67001 | pTa | high | positive | suspicious | yes | -20 | 4.9 | -20 | 4.8 | 1.1 | -20 | -1.6 | -3.6 | positive |
| 67006 | pT1 | high | positive | positive | no | -0.7 | 4.4 | -6.2 | 5.7 | -2.8 | -0.6 | -20 | 2.2 | positive |
| 67009 | pT2 | high | positive | positive | no | -20 | 4.9 | -0.4 | 4.9 | 1.5 | -20 | 1.1 | -20 | positive |
| 75211 | pT2 | high | positive | negative | no | -0.8 | 1.4 | -4.1 | | | | | | positive |
| 75216 | pTa, CIC | high | positive | suspicious | yes | -3.5 | 2 | -0.8 | 0.9 | -0.6 | -3.4 | | | positive |
| 75218 | pTa | high | positive | negative | no | 0.9 | 3.8 | -0.9 | 3.8 | -1.6 | 0.5 | | | positive |
| 75245 | pTa | high | positive | NA | no | 20 | 1.6 | 6.7 | 0.4 | 6.2 | 20 | 1.9 | 8.2 | positive |
| 75247 | CIS | high | positive | atypical | no | -1.4 | 3.4 | 2.7 | 3.6 | 3.7 | -3.8 | -0.2 | 0.4 | positive |
| 75248 | pT1/CIS | high | positive | atypical | no | -20 | 4.3 | 0 | 4.8 | 1 | -20 | 0.4 | -5.1 | positive |
| 75249 | pT1 | high | positive | negative | no | -20 | 3.3 | 2.1 | 3.4 | 2.5 | -20 | 3.7 | -20 | positive |
| 75258 | CIS, pTa | high | positive | atypical | no | | | | 4.2 | -3.7 | 0.6 | -2 | 1.9 | positive |
| 75246 | | | positive | positive | no | -20 | 4.3 | 5.3 | 4.4 | 5.9 | 9.1 | -1 | 3.4 | positive |

TABLE 4

Detection of low grade bladder cancer

| | | | | | history of | TSR lot CL3 | | | TSR lot CL4 | | | CIC TSR lot CL1 | | |
|---|---|---|---|---|---|---|---|---|---|---|---|---|---|---|
| Sample ID | stage | grade | UroVysion ® Result | cytology | bladder cancer | CRH -10 | KRT20 2.2 | IGF2 -1 | KRT20 4 | IGF2 0.5 | CRH -5 | ANXA10 -0.5 | CRH -3 | GX result |
| 67002 | pTa | low | negative | atypical | yes | -20 | 3.9 | -3.8 | 3.3 | -1.5 | -20 | -1.7 | -20 | positive |
| 67003 | pTa | low | negative | negative | no | -20 | -20 | -3.2 | -20 | -20 | -20 | -20 | -20 | negative |
| 67004 | pTa | low | negative | negative | no | -2 | 4.7 | -2.3 | 5.2 | 0.1 | -1.7 | 2.4 | 2.2 | positive |
| 67010 | pTa | low | positive | atypical | no | -20 | -5.3 | -8.8 | -3.8 | -6.7 | -20 | -5 | -20 | negative |
| 67011 | pTa | low | positive | atypical | no | -1.3 | 4.6 | 1.9 | 4 | 2.4 | -2 | -1.3 | 1 | positive |
| 67018 | pTa | low | negative | atypical | yes | -20 | -20 | -4.4 | -20 | -20 | -20 | -20 | -20 | negative |
| 67050 | pTa | low | negative | atypical | yes | -20 | -0.4 | 3.4 | 1.9 | 3.3 | -20 | -0.5 | -20 | positive |
| 67100 | pTa | low | borderline | atypical | yes | | | | -2.9 | -2.7 | -20 | -20 | -20 | negative |
| 75161 | pTa | low | negative | atypical | yes | -20 | -3 | -4.7 | -3.6 | -1.3 | -20 | -5.7 | -20 | negative |
| 75183 | pTa | low | positive | negative | yes | -1.5 | 3.1 | -2 | 3.4 | -0.5 | 0.7 | -4.1 | 2.3 | positive |
| 75184 | pTa | low | inconclusive | negative | yes | -20 | -0.6 | 1.3 | -1.5 | 1.8 | -20 | -20 | -20 | positive |
| 75185 | pTa | low | negative | negative | no | -20 | 3 | 5 | 1.3 | 4.7 | -20 | 1.2 | -4.2 | positive |
| 75191 | pTa | low | negative | negative | yes | -20 | -0.4 | -3.4 | 1.1 | -0.5 | -20 | -4.1 | -20 | negative |
| 75202 | pTa | low | negative | negative | yes | -20 | 0.3 | -2.3 | -0.4 | -1.5 | -20 | -2.4 | -20 | negative |
| 75236 | pTa | low | negative | negative | no | -20 | -5.7 | -7.9 | -20 | -8.9 | -20 | -3.2 | -20 | negative |
| 75251 | pTa | low | negative | negative | yes | -20 | -3.6 | -5.1 | -1 | -4.4 | -20 | -20 | -20 | negative |
| 75257 | pTa | low | negative | negative | no | | | | -2.1 | -0.9 | -20 | -20 | -20 | negative |
| 75265 | pTa | low | negative | negative | yes | | | | 1.4 | -20 | -20 | -20 | -20 | negative |

A summary of the sensitivity for high grade bladder cancer and low grade bladder cancer, and the specificity in patients with a low risk of bladder cancer, is shown in Table 5 for each of the individual markers tested in Tables 3 and 4.

TABLE 5

Summary of sensitivity and specificity of individual markers

| Marker | Sensitivity, high grade bladder cancer | Sensitivity, low grade bladder cancer | Specificity, low risk of bladder cancer |
|---|---|---|---|
| CRH | 15/30 (50%) | 9/53 (17%) | 220/221 (99%) |
| KRT20 | 11/21 (52%) | 6/34 (18%) | 144/145 (99%) |
| IGF2 | 13/21 (62%) | 8/34 (24%) | 144/145 (99%) |
| ANXA10 | 5/9 (56%) | 2/19 (11%) | 74/76 (97%) |
| 4 marker combo | 12/12 (100%) | 7/19 (37%) | 83/88 (94%) |

Exemplary alternative primers and probes for detecting the four markers, KRT20, IGF2, CRH, and ANXA10, are shown in Table 6. Table 6 also shows an exemplary set of primers and probes for detecting an exogenous control and an endogenous control, ABL. The dyes and quenchers shown in Table 6 are generic, and two or more of quenchers Q1 to Q6 may be the same. One skilled in the art could select a suitable set, for example, a set of detectably different dyes for use in a multiplex assay. The predicted amplicon length for each set of primers is also shown, as well as the length of any intervening intron(s) between the primer sites on the genomic copy of the target.

TABLE 6

Primer and probe sequences

| name | 5' mod | sequence | 3' mod | SEQ ID NO | amplicon length (bp) | intron length (bp) |
|---|---|---|---|---|---|---|
| KRT20 For_3 | | CGACTACAGTGCATATTACAGACAA | | 29 | 113 | 2142 |
| KRT20 Rev_2 | | CAGCAGCCAGTTTAGCATTATCAA | | 30 | | |
| KRT20 Probe | F1 | TCAACTGCAAAA (T-dabsyl) GCTCGGTGTGTCC | Q1 | 31 | | |
| IGF2 For_5 | | GGACCGCGGCTTCTACTTCA | | 32 | 95 | 1701 |
| IGF2 Rev_5 | | CCAGGTCACAGCTGCGGAA | | 33 | | |
| IGF2 Probe_2_F4 | F4 | TGTGAGCCGTCGCAGCCGTG | Q4 | 34 | | |
| CRH_For 4 | | TGCGAAGCGCCTGGGAAGC | | 35 | 66 | 801 |
| CRH_Rev | | GGACTCCCGCGGACACAA | | 36 | | |
| CRH_probe_F2 | F2 | TGCCCCTAACATGCGGCTGCC | Q2 | 37 | | |
| ANXA10_For_3 | | TCAGCGCTGCAATGCACAA | | 38 | 122 | 22,947 |
| ANXA10_For_4 | | CTGCAATGCACAAAGGATGA | | 48 | 117 | 22,947 |
| ANXA10_Rev_5 | | GGCCAGCCATCACATCTTTGAA | | 39 | | |
| ANXA10_Probe_3 | F3 | TAGAGCATGTATGGCCGGGACCT | Q3 | 40 | | |
| ABLa3a4 PrmrFwd4 | | GATCAACACTGCTTCTGATGGCAA | | 41 | 92 | 7666 |
| ABLa3a4 PrmrRev1 | | CCACCGTTGAATGATGATGAACCAA | | 42 | | |
| ABL Probe F5 | F5 | CCTCCGAGAGCCGCTTCAAC | Q5 | 43 | | |
| Armored RNA® Fwd | | GGCTATTCTCCTCTTGGCAGAT | | 44 | 101 | NA |
| Armored RNA® Rev | | TGCTTGAGCTCCAGTCCCTAAG | | 45 | | |
| Armored RNA® Probe | F6 | AGCCGAGAAGGCGGAGTCTGGC | Q6 | 46 | | |

5.2. Example 2

Assay Sensitivity for Detecting Bladder Cancer Using Marker Panel KRT20, IGF2, CRH, and ANXA10 in a Larger Cohort Urine samples were collected from subjects at seven different sites. Eligibility criteria for inclusion in the study included:
18 years or older;
Documented informed consent as required by the reviewing IRB or HREC, and a signed Experimental Subjects Bill of Rights for patients in California;
At least one of the following criteria:
A history or recurrence of bladder cancer;
A referral for cystoscopy evaluation due to micro- or gross-hematuria in urine;
A referral for urology evaluation, but no previous history of bladder cancer or clinical evidence of bladder cancer;
Consent to provide at least 15 ml voided urine in addition to that required for standard of care;
Consent to allow pathology results for any biopsy specimens taken during cystoscopy procedure and other medical records to be reported.
Exclusion criteria included only under 18 years of age and first voided urine. Patients currently or previously treated with Bacillus Calmette-Guerin (BCG) and patients currently or previously treated with intravesical therapy or transurethral resection of bladder or radiation therapy for bladder cancer were eligible for the study. In addition, repeat enrollment during the course of the study was also permitted.

Two of the collection sites provided the results of UroVysion® analysis on the urine samples. For each sample to be tested 15 mL of voided urine was added to 15 mL of preservative (3.5M guanidine HCl, 1% N-acetyl-L-cysteine, 25 mM sodium citrate, and 2.5% Tween-20, pH 3.2), preferably within 1 hour of sample collection. The preserved samples were transported on ice and stored at 4° C. Clinical information for each sample was provided by the collection sites.

Prior to use, the preserved urine was inverted three times to mix. 4 mL of preserved urine was loaded into a GeneXpert cartridge for analysis. The cartridge contained a 0.8 µm filter to capture urothelial cells. The captured cells were washed and lysed using sonication (2-15 seconds, 8-16 µm at 36 kHz) within the cartridge. The lysate was then used to reconstitute the reagents used for real-time RT-PCR (described above). The reaction cycle used was: 10 minutes at 45° C., followed by 2 minutes at 95° C., and then 45 cycles of (a) 5 seconds at 95° C., 20 seconds at 60° C., and 20 seconds at 72° C., using a GeneXpert® cartridge in a GeneXpert® system. For ANXA10, KRT20 and IGF2, delta Ct ($\Delta$Ct) was calculated as Ct (ABL)–Ct (marker). The $\Delta$Ct cutoff was set as the $\Delta$Ct that gave high (>90%) specificity with samples from patients not expected to have bladder cancer (data not shown). A $\Delta$Ct above the $\Delta$Ct cutoff for any one of the markers was considered a positive result, indicative of the presence of bladder cancer. For CRH, Ct values were used instead of $\Delta$Ct to determine positivity for the CRH marker. A CRH Ct value <45 was considered a positive result, indicative of the presence of bladder cancer. In addition to the four bladder cancer markers (KRT20, IGF2, CRH, and ANXA10), the GeneXpert® bladder cancer assay included two controls: primers and probe for detecting ABL mRNA in the samples, and primers and probe for detecting an Armored RNA® exogenous control RNA.

In the first analysis, 132 samples collected from patients who had positive cystoscopy results for bladder cancer were tested with the GeneXpert® bladder cancer assay. Sixty of those samples had also been tested using UroVysion®. Table 7 shows the results for those 132 samples.

TABLE 7

Assay sensitivity by bladder cancer stage and grade

|  | Xpert Bladder | | | | UroVysion | | | |
|---|---|---|---|---|---|---|---|---|
|  | POS | NEG | Invalid/Error** | Sensitivity | POS | NEG | inconclusive | Sensitivity |
| Stage: | | | | | | | | |
| All | 94 | 35 | 3 | 72.9% | 29 | 26 | 5 | 52.7% |
| Ta, Grade Low | 29 | 23 | 2 | 55.8% | 5 | 18 | 4 | 21.7% |
| Ta, Grade High | 20 | 2 |  | 90.9% | 4 | 6 | 1 | 40.0% |
| T1 | 13 | 2 |  | 86.7% | 6 | 1 |  | 85.7% |
| T2 | 11 | 2 |  | 84.6% | 4 | 0 |  | 100.0% |
| T3 | 3 | 0 |  | 100.0% | 1 | 0 |  | 100.0% |
| T4 | 2 | 0 |  | 100.0% |  |  |  |  |
| CIS | 11 | 1 |  | 91.7% | 7 | 0 |  | 100.0% |
| UNK | 5 | 5 | 1 | 50.0% | 2 | 1 |  | 66.7% |
| Grade: | | | | | | | | |
| All | 94 | 35 | 3 | 72.9% | 29 | 26 | 5 | 52.7% |
| Low Grade | 33 | 28 | 2 | 54.1% | 6 | 19 | 4 | 24.0% |
| High Grade | 61 | 7 | 1 | 89.7% | 23 | 7 | 1 | 76.7% |

**Two invalid results were due to low ABL Ct, suggesting a low number of cells in the sample, and one of the invalid results was due to poor sample quality.

As shown in Table 7, for these samples, the GeneXpert bladder cancer assay had a sensitivity of 54.1% for low grade bladder cancer and a sensitivity of 89.7% for high grade bladder cancer. In contrast, UroVysion® had a sensitivity of just 24% for low grade bladder cancer and a sensitivity of 76.6% for high grade bladder cancer. Further, the GeneXpert® bladder cancer assay was able to detect all grades and stages of bladder cancer.

The same data set was then divided according to three patient groups: (A) patients with a history of bladder cancer who were currently being monitored for recurrence of bladder cancer, (B) patients who had been treated with Bacillus Calmette-Guerin (BCG) within the three months prior to sample collection, and (C) patients who were symptomatic for bladder cancer and had no prior history of bladder cancer. The results for those patient groups are shown in Table 8.

As shown in Table 8, the GeneXpert® bladder cancer assay had a similar sensitivity for low grade and high grade bladder cancer in patients being monitored for bladder cancer and in patients who were symptomatic of bladder cancer as in the patient group as a whole (see Table 7). In patients who had been treated with BCG within the last three months, the GeneXpert® bladder cancer assay had a sensitivity of 66.7%, although the sample size was too small (6 samples) to draw any conclusions from that result.

In order to have a direct comparison of the GeneXpert® bladder cancer assay and UroVysion®, a dataset was selected that included only samples that had been tested with both assays. Table 9 shows the results for that dataset, with the patients separated into two groups: (A&B) patients with a history of bladder cancer who were currently being moni-

TABLE 8

Assay sensitivity by patient population

|  | Xpert Bladder* | | | | UroVysion | | | |
|---|---|---|---|---|---|---|---|---|
| Grade: | POS | NEG | Invalid/Error** | Sensitivity | POS | NEG | inconclusive | Sensitivity |
| | Monitoring (Population A) | | | | | | | |
| All | 50 | 20 | 1 | 71.4% | 11 | 12 |  | 47.8% |
| Low Grade | 21 | 18 |  | 53.8% | 2 | 11 | 1 | 15.4% |
| High Grade | 29 | 2 | 1 | 93.5% | 9 | 1 |  | 90.0% |
| | Treated with BCG in last 3 months (Population B) | | | | | | | |
| All | 4 | 2 |  | 66.7% | 1 |  |  | 100.0% |
| Low Grade | | | | | | | | |
| High Grade | 4 | 2 |  | 66.7% | 1 |  |  | 100.0% |
| | Symptomatic (Population C) | | | | | | | |
| All | 40 | 13 | 2 | 75.5% | 17 | 14 | 4 | 54.8% |
| Low Grade | 12 | 10 | 2 | 54.5% | 4 | 8 | 3 | 33.3% |
| High Grade | 28 | 3 |  | 90.3% | 13 | 6 | 1 | 68.4% |

**Two invalid results were due to low ABL Ct, suggesting a low number of cells in the sample, and one of the invalid results was due to poor sample quality.

tored for recurrence of bladder cancer, combined with patients who had been treated with Bacillus Calmette-Guerin (BCG) within the three months prior to sample collection (these groups were combined because only one sample from a BCG-treated patient had been tested with both assays), and © patients who were symptomatic for bladder cancer and had no prior history of bladder cancer.

TABLE 9

Assay sensitivity for samples tested with both GeneXpert ® and UroVysion ®

| Grade: | Xpert Bladder | | | | UroVysion | | | |
|---|---|---|---|---|---|---|---|---|
| | POS | NEG | Invalid/Error** | Sensitivity | POS | NEG | inconclusive | Sensitivity |
| Monitoring and BCG treated (Populations A&B) | | | | | | | | |
| All | 18 | 7 | 1 | 72.0% | 12 | 13 | 1 | 48.0% |
| Low Grade | 6 | 7 | 1 | 46.2% | 2 | 12 | | 14.3% |
| High Grade | 12 | 0 | | 100.0% | 10 | 1 | 1 | 90.9% |
| Symptomatic (Population C) | | | | | | | | |
| All | 26 | 8 | 1 | 76.5% | 17 | 14 | 4 | 54.8% |
| Low Grade | 7 | 7 | 1 | 50.0% | 4 | 8 | 3 | 33.3% |
| High Grade | 19 | 1 | | 95.0% | 13 | 6 | 1 | 68.4% |

As shown in T 9, for those samples that have been tested with both GeneXpert® bladder cancer assay and UroVysion®, the GeneXpert® bladder cancer assay showed greater sensitivity than UroVysion® for detecting low grade and high grade cancer in both patient groups.

Next, the data set was divided into samples that had been archived, meaning they were tested more than one week after collection (the samples ranged from 8 days old up to nine months old), and samples that were fresh, meaning they were tested within one week of collection. The results of that analysis are shown in Table 10.

TABLE 10

Assay sensitivity in archived and fresh samples

| | Xpert Bladder | | | | |
|---|---|---|---|---|---|
| Grade: | n | POS | NEG | Invalid/Error** | Sensitivity |
| Archived Samples | | | | | |
| All | 89 | 61 | 25 | 3 | 70.9% |
| Low Grade | 46 | 23 | 21 | 2 | 52.3% |
| High Grade | 43 | 38 | 4 | 1 | 90.5% |
| Fresh Samples | | | | | |
| All | 43 | 33 | 10 | | 76.7% |
| Low Grade | 17 | 10 | 7 | | 58.8% |
| High Grade | 26 | 23 | 3 | | 88.5% |

**Two invalid results were due to low ABL Ct, suggesting a low number of cells in the sample, and one of the invalid results was due to poor sample quality.

As shown in Table 10, the GeneXpert® bladder cancer assay had a similar sensitivity for detecting low grade and high grade bladder cancer in fresh and archived samples.

5.3. Example 3

Assay Specificity for Detecting Bladder Cancer Using Marker Panel KRT20, IGF2, CRH, and ANXA10 in a Larger Cohort In addition to the samples from patients with positive cystoscopy results for bladder cancer, urine samples were collected at the seven sites from patients with negative cystoscopy results for bladder cancer, but who were being monitored for recurrence of bladder cancer, had received BCG within the three months prior to sample collection, and who appeared to be symptomatic for bladder cancer but had no prior history of bladder cancer. In addition, urine samples were collected from patients with urology referrals for other suspected conditions, such as kidney stones. Finally, urine samples were collected from healthy individuals. Urine samples were preserved and analyzed using the GeneXpert® bladder cancer assay as described in Example 2.

For the samples from patients with negative cystoscopy results for bladder cancer, the assay results were divided according to the three patient groups: (A) patients with a history of bladder cancer who were currently being monitored for recurrence of bladder cancer, (B) patients who had been treated with Bacillus Calmette-Guerin (BCG) within the three months prior to sample collection, and (C) patients who were symptomatic for bladder cancer and had no prior history of bladder cancer. The results for those patient groups are shown in Table 11.

TABLE 11

Assay specificity in cystoscopy negative patients by population
Xpert Bladder

| POS | NEG | Invalid/Error | Specificity |
|---|---|---|---|
| Monitoring (Population A) | | | |
| 55 | 156 | 17 | 73.9% |
| BCG Treated (Population B) | | | |
| 1 | 6 | 0 | 85.7% |
| Symptomatic (Population C) | | | |
| 16 | 86 | 10 | 84.3% |

As shown in Table 11, the GeneXpert® bladder cancer assay had a specificity of 73.9%, 85.7%, and 84.3% for patient groups (A), (B), and (C), respectively.

Next, the specificity of the GeneXpert® bladder cancer assay in patients who were suspected of having other urological conditions, but not bladder cancer, was determined. Seventy patient samples were collected in this category. The results with the GeneXpert® bladder cancer assay were 14 positives, 50 negatives, and 6 invalid results. The specificity of the GeneXpert® bladder cancer assay for this patient population was therefore 78.1%.

Finally, the specificity of the GeneXpert® bladder cancer assay in healthy individuals was determined Fifty-five samples were collected in this category. The results were 4 positives and 51 negatives, indicating a specificity of 92.7% for this subject category.

5.4. Example 4

Detection of Bladder Cancer in Samples that were Weakly Positive or False Negative Using Marker Panel KRT20, IGF2, CRH, and ANXA10

A collection of samples, including many samples that were weakly positive or false negative from the cohorts above, were analyzed using two additional markers, androgen receptor (AR) and uroplakin 1B (UPK1B).

Two milliliters of preserved urine was loaded onto a GeneXpert® cartridge and the urine was run through the filter. Cells caught on the filter were removed using a 3M guanidinium thiocyanate and 0.1% sarkosyl. RNA from the cells was purified using RNeasy mini kit (Qiagen). RNA samples were then analyzed on a SmartCycler® (Cepheid, Sunnyvale, Calif.). Each reaction contained 5 µl of purified RNA, 400 nM forward primer for ABL, 400 nM forward primer for each target RNA (AR and/or UPK1B), 400 nM reverse primer for ABL, 400 nM reverse primer for each target RNA, 200 nM ABL probe, and 300 nM probe for each target RNA, 50-90 mM KCl, 3-5 mM $MgCl_2$, 400-825 µM dNTPs, 20 mM Tris, pH 8.5, 0.01% sodium azide, and 0.125 units/µl of Rnase inhibitor. MMLV reverse transcriptase (0.375 units/µl) and AptaTaq (0.25 units/µl; Roche) were used for reverse transcription and amplification, respectively. The cycle used was 45° C. for 600 seconds, 95° C. for 120 seconds, and 45 cycles of: 95° C. for five seconds, 60° C. for 20 seconds, and 72° C. for 20 seconds. Primer and probe sequences for detecting AR and UPK1B are shown in Table 12.

TABLE 12

Primers and probes

| Name | Sequence | SEQ ID NO | Amplicon length | Intron length |
|---|---|---|---|---|
| UPK1B_For | CGGACTGAGAATAATGATGCTGA | 51 | 141 | 4658 |
| UPK1B_Rev | GATCAGTTCATAGCAGCCCTG | 52 | | |
| UPK1B_probe | TCTCAACCTGGAGGCTTGTAAACTAGG | 53 | | |
| AR_For | GGACTCCGTGCAGCCTATT | 54 | 136 | 701 |
| AR_Rev | AGAAAGGATCTTGGGCACTTG | 55 | | |
| AR_Probe | TCAGTTCACTTTTGACCTGCTAATCAAGTC | 56 | | |

If the ABL Ct was greater than 39, the sample was removed from the analysis. Delta Ct (ΔCt) was calculated as Ct (ABL)−Ct (marker). The ΔCt cutoff for AR was set as −4.5 and the ΔCt cutoff for UPK1B was set at 1.5. A ΔCt above the ΔCt cutoff for any one of the markers was considered a positive result, indicative of the presence of bladder cancer. If no target was detected in the sample, the Ct was set at 0, and the ΔCt was set at −20. The results of the experiment are shown in Table 13.

TABLE 13

Detection of bladder cancer using AR and UPK1B

| Sample ID | ABL Ct | AR Ct | AR ΔCt | UPK1B Ct | UPK1B ΔCt | Status | AR Result | UPK1B Result | Prior result |
|---|---|---|---|---|---|---|---|---|---|
| 14230 | 34.9 | 0 | −20 | 35.4 | −0.5 | healthy | Neg | Neg | |
| 14231 | 37.1 | 0 | −20 | 0 | −20 | healthy | Neg | Neg | |
| 14234 | 37.9 | 0 | −20 | 0 | −20 | healthy | Neg | Neg | |
| 14235 | 37.1 | 0 | −20 | 0 | −20 | healthy | Neg | Neg | |
| 14236 | 35.6 | 0 | −20 | 0 | −20 | healthy | Neg | Neg | |
| 14237 | 37.3 | 0 | −20 | 0 | −20 | healthy | Neg | Neg | |
| 14238 | 35.9 | 0 | −20 | 0 | −20 | healthy | Neg | Neg | |
| 165010 | 36.6 | 0 | −20 | 0 | −20 | healthy | Neg | Neg | Neg |
| 165017 | 38.1 | 0 | −20 | 0 | −20 | healthy | Neg | Neg | Neg |
| 165026 | 38.8 | | | 0 | −20 | healthy | | Neg | Neg |
| 165044 | 38.2 | | | 0 | −20 | healthy | | Neg | Neg |
| 165046 | 37.4 | 38.1 | −0.7 | 0 | −20 | healthy | Pos | Neg | Neg |
| CPHD-021 | 36.6 | 0 | −20 | 0 | −20 | healthy | Neg | Neg | Neg |
| CPHD-031 | 38.5 | 0 | −20 | 0 | −20 | healthy | Neg | Neg | Neg |
| 75171 | 34.4 | 36.3 | −1.9 | 0 | −20 | SCI | Pos | Neg | |
| 75178 | 35.8 | 40.5 | −4.7 | 34.3 | 1.5 | SCI | Neg | Neg | |
| 75179 | 35.3 | 0 | −20 | 34.3 | 1 | SCI | Neg | Neg | |
| 75194 | 36.7 | 0 | −20 | 0 | −20 | SCI | Neg | Neg | |
| 75210 | 37 | 37.2 | −0.2 | 35.3 | 1.7 | SCI | Pos | Pos | |
| 75217 | 33.5 | 44.7 | −11 | 27.7 | 5.8 | SCI | Neg | Pos | |
| 75225 | 34 | 0 | −20 | 0 | −20 | SCI | Neg | Neg | |
| 75230 | 34.1 | 0 | −20 | 33.8 | 0.3 | SCI, UTI | Neg | Neg | |
| 67054 | 37.2 | 40.3 | −3.1 | 35 | 2.2 | HG | Pos | Pos | Pos |
| 67111 | 34.1 | 0 | −20 | 30.6 | 3.5 | HG | Neg | Pos | Pos |
| 75144 | 34.7 | 38.8 | −4.1 | | | HG | Pos | | |
| 75144 | 35.2 | | | 34.4 | 0.8 | HG | | Neg | |
| 75151 | 31.6 | 33.6 | −2 | | | HG | Pos | | |
| 75151 | 31.8 | | | 26.4 | 5.4 | HG | | Pos | |

TABLE 13-continued

Detection of bladder cancer using AR and UPK1B

| Sample ID | ABL Ct | AR Ct | AR ΔCt | UPK1B Ct | UPK1B ΔCt | Status | AR Result | UPK1B Result | Prior result |
|---|---|---|---|---|---|---|---|---|---|
| 75170 | 29.4 | 30.4 | −1 | | | HG | Pos | | |
| 75170 | 29.6 | | | 25 | 4.6 | HG | | Pos | |
| 75203 | 32.1 | 35.9 | −3.8 | | | HG | Pos | | |
| 75203 | 32.4 | | | 27.1 | 5.3 | HG | | Pos | |
| 75417 | 32.6 | 32.9 | −0.3 | | | HG | Pos | | False Neg |
| 75417 | 33.8 | | | 31.7 | 2.1 | HG | | Pos | False Neg |
| 75462 | 36.9 | 0 | −20 | | | HG | Neg | | Weak pos |
| 75462 | 35.7 | | | 34 | 1.7 | HG | | Pos | Weak pos |
| 75470 | 33.2 | 33.5 | −0.3 | | | HG | Pos | | Weak pos |
| 75470 | 34.5 | | | 30.5 | 4 | HG | | Pos | Weak pos |
| 75540 | 32.5 | 32.7 | −0.2 | 25.9 | 6.6 | HG | Pos | Pos | Pos |
| 165013 | 37.1 | 38.9 | −1.8 | | | HG | Pos | | Weak pos |
| 165013 | 38.7 | | | 36.5 | 2.2 | HG | | Pos | Weak pos |
| 165099 | 37.5 | 0 | −20 | | | HG | Neg | | False Neg |
| 67010 | 34.1 | 0 | −20 | | | LG | Neg | | False Neg |
| 67010 | 34.5 | | | 0 | −20 | LG | | Neg | False Neg |
| 67011 | 35 | 39.8 | −4.8 | | | LG | Neg | | Pos |
| 67011 | 35.3 | | | 30.2 | 5.1 | LG | | Pos | |
| 75089 | 37.1 | 0 | −20 | | | LG | Neg | | |
| 75089 | 36.2 | | | 30.5 | 5.7 | LG | | Pos | |
| 75101 | 37.7 | 41.6 | −3.9 | | | LG | Pos | | |
| 75101 | 37.2 | | | 33 | 4.2 | LG | | Pos | |
| 75245 | 32.6 | | | 29 | 3.6 | LG | | Pos | |
| 75444 | 35.9 | 37 | −1.1 | | | LG | Pos | | Weak pos |
| 75444 | 37.3 | | | 33.6 | 3.7 | LG | | Pos | Weak pos |
| 75475 | 33.9 | 34.4 | −0.5 | 30.4 | 3.5 | LG | Pos | Pos | False Neg |
| 75483 | 34.6 | 34.5 | 0.1 | 31.5 | 3.1 | LG | Pos | Pos | False Neg |
| 75485 | 34.3 | 34.6 | −0.3 | 30.5 | 3.8 | LG | Pos | Pos | False Neg |
| 75519 | 35.1 | 35.1 | 0 | 31.8 | 3.3 | LG | Pos | Pos | False Neg |
| 75539 | 37.6 | 36.8 | 0.8 | 31.2 | 6.4 | LG | Pos | Pos | False Neg |
| 165049 | 37.9 | 0 | −20 | 0 | −20 | LG | Neg | Neg | False Neg |
| 165062 | 38.7 | | | 0 | −20 | LG | | Neg | False Neg |
| 165098 | 37.8 | 0 | −20 | 0 | −20 | LG | Neg | Neg | False Neg |

SCI = spinal cord injury
UTI = urinary tract infection
HG = high-grade bladder cancer
LG = low grade bladder cancer Using either AR or UPK1B as a bladder cancer marker, at least six samples were identified as positive for bladder cancer that had been previously been identified as false negatives using the four marker panel described above.

The sensitivity and specificity for detecting bladder cancer using AR or UPK1B is shown in Table 14.

TABLE 14

Sensitivity and specificity

| AR | | UPK1B | |
|---|---|---|---|
| Sensitivity n = 24 bladder cancer | Specificity n = 20 healthy | Sensitivity n = 25 bladder cancer | Specificity n = 22 healthy |
| 67% | 85% | 80% | 90.9% |

Twenty-three high grade and low grade bladder cancer samples were tested with both AR and UPK1B. The sensitivity of the combination of AR and UPK1B (considering both single positives and double positives as positive results) for the tested samples is 87%.

Some of the samples had lower ABL levels, indicating that there may be a low number of cells in the sample. In samples with an ABL Ct of less than 36, the sensitivity of both markers increases, as shown in Table 15.

TABLE 15

Sensitivity and specificity in samples with ABL Ct < 36

| AR | | UPK1B | |
|---|---|---|---|
| Sensitivity n = 15 bladder cancer | Specificity n = 9 healthy | Sensitivity n = 16 bladder cancer | Specificity n = 9 healthy |
| 80% | 88.9% | 87.5% | 88.9% |

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that changes can be made without departing from the spirit and scope of the invention(s).

TABLE OF CERTAIN SEQUENCES

| SEQ ID NO | Description | Sequence |
|---|---|---|
| 1 | Human CRH mRNA | TCGTTCCTTG GCAGGGCCCT ATGATTTATG CAGGAGCAGA GGCAGCACGC AATCGAGCTG<br>TCAAGAGAGC GTCAGCTTAT TAGGCAAATG CTGCGTGGTT TTTGAAGAGG GTCGACACTA<br>TAAAATCCCA CTCCAGGCTC TGGAGTGGAG AAACTCAGAG ACCAAGTCCA TTGAGAGACT<br>GAGGGGAAAG AGAGGAGAGA AAGAAAAAGA GAGTGGGAAC AGTAAAGAGA AAGGAAGACA<br>ACCTCCAGAG AAAGCCCCCG GAGACGTCTC TCTGCAGAGA GGCGGCAGCA CCCGGCTCAC<br>CTGCGAAGCG CCTGGGAAGC GAGTGCCCCT AACATGCGGC TGCCGCTGCT TGTGTCCGCG<br>GGAGTCCTGC TGGTGGCTCT CCTGCCCTGC CCGCCATGCA GGGCGCTCCT GAGCCGCGGG<br>CCGGTCCCGG GAGCTCGGCA GGCGCCGCAG CACCCTCAGC CCTTGGATTT CTTCCAGCCG<br>CCGCCGCAGT CCGAGCAGCC CCAGCAGCCG CAGGCTCGGC CGGTCCTGCT CCGCATGGGA<br>GAGGAGTACT TCCTCCGCCT GGGGAACCTC AACAAGAGCC CGGCCGCTCC CCTTTCGCCC<br>GCCTCCTCGC TCCTCGCCGG AGGCAGCGGC AGCCGCCCTT CGCCGGAACA GGCGACCGCC<br>AACTTTTTCC GCGTGTTGCT GCAGCAGCTG CTGCTGCCTC GGCGCTCGCT CGACAGCCCC<br>GCGGCTCTCG CGGAGCGCGG CGCTAGGAAT GCCCTCGGCG GCCACCAGGA GGCACCGGAG<br>AGAAAAGGC GGTCCGAGGA GCCTCCCATC TCCCTGGATC TCACCTTCCA CCTCCTCCGG<br>GAAGTCTTGG AAATGGCCAG GGCCGAGCAG TTAGCACAGC AAGCTCACAG CAACAGGAAA<br>CTCATGGAGA TTATTGGGAA ATAAACGGT GCGTTTGGCC AAAAAGAATC TGCATTTAGC<br>ACAAAAAAAA TTTAAAAAAA TACAGTATTC TGTACCATAG CGCTGCTCTT ATGCCATTTG<br>TTTATTTTTA TATAGCTTGA AACATAGAGG GAGAGAGGGA GAGAGCCTAT ACCCCTTACT<br>TAGCATGCAC AAAGTGTATT CACGTCAGC AGCAACACAA TGTTATTCGT TTTGTCTACG<br>TTTAGTTTCC GTTTCCAGGT GTTTATAGTG GTGTTTTAAA GAGAATGTAG ACCTGTGAGA<br>AAACGTTTTG TTTGAAAAAG CAGACAGAAG TCACTCAATT GTTTTTGTTG TGGTCTGAGC<br>CAAAGAGAAT GCCATTCTCT TGGGTGGGTA AGACTAAATC TGTAAGCTCT TTGAAACAAC<br>TTTCTCTTGT AAACGTTTCA GTAATAAAAC ATCTTTCCAG TCCTTGGTCA GTTTGGTTGT<br>GTAAGAGAAT GTTGAATACT TATATTTTTA ATAAAAGTTG CAAAGGTAAT CATG |
| 2 | Human IGF2 mRNA, transcript variant 2 | CCGCTAATGT ACCATGCCCT GGTGCTGGAA AGTGCCTGAG CCAGCTGCCC CAGCGGCCTC<br>AGCACTACCA AGTTGGCACA AAGCTCCCCA AATTCGGAGG GGCTCAGGGA AACGAGTGGA<br>GGGGATGAGG AGGTGAGGGG TAAACCCATC ATTTCAGTTG GCATTTGAGC AGGTGCCATG<br>CTCAGCGGAG ATGAGGCTCT CCCATCTGTA GGGGCCGTAT TAACATGCAC ACTCTAAAAG<br>TGCCCTTCGT TTCTCCAGCC TCAGCTTTGT CCCTCTCCTC CTCCACGTCA ACCTGGCCAG<br>AGGGTCTGGA CGCCACAGCC AGGGCACCCC CTGCTTTGGT GGTGACTGCT<br>AATATTGGCC AGGCCGGCGG ATCATCGTCC AGGCAGTTTC GGCAGAGAGC CTTGGGCACC<br>AGTGACTCCC CGGTCCTCTT TATCCACTGT CCAGGAGCTG CGGGGACTGC GCAGGGACTA<br>GAGTACAGGG GCCGAAGAGT CACCACCGAG CTTGTGTGGG AGGAGGTGGA TTCCAGCCCC<br>CAGCCCCAGG GCTCTGAATC GCTGCCAGCT CAGCCCCCTG CCCAGCCTGC CCCACAGCCT<br>GAGCCCCAGC AGGCCAGAGA GCCCAGTCCT GAGGTGAGCT GCTGTGGCCT GTGGCCCAGG<br>CGACCCCAGC GCTCCCAGAA CTGAGGCTGG CAGCCAGCCC CAGCCTCAGC CCAACTGCGG<br>AGGCAGAGAG ACACCAATGG GAATCCCAAT GGGGAAGTCG ATGCTGGTGC TTCTCACCTT<br>CTTGGCCTTC GCCTCGTGCT GCATTGCTGC TTACCGCCCC AGTGAGACCC TGTGCGGCGG<br>GGAGCTGGTG GACACCCTCC AGTTCGTCTG TGGGGACCGC GGCTTCTACT TCAGCAGGCC<br>CGCAAGCCGT GTGAGCCGTC GCAGCCGTGG CATCGTTGAG GAGTGCTGTT TCCGCAGCTG<br>TGACCTGGCC CTCCTGGAGA CGTACTGTGC TACCCCCGCC AAGTCCGAGA GGGACGTGTC<br>GACCCCTCCG ACCGTGCTTC CGGACAACTT CCCCAGATAC CCCGTGGGCA<br>AGTTCTTCCA ATATGACACC TGGAAGCAGT CCACCCAGCG CCTGCGCAGG GGCCTGCCTG<br>CCCTCCTGCG TGCCCGCCGG GGTCACGTGC TCGCCAAGGA GCTCGAGGCG TTCAGGGAGG<br>CCAAACGTCA CCGTCCCCTG ATTGCTCTAC CCACCCAAGA CCCCGCCCAC GGGGGCGCCC<br>CCCCAGAGAT GGCCAGCAAT CGGAAGTGAG CAAAACTGCC GCAAGTCTGC AGCCCGGCGC<br>CACCATCCTG CAGCCTCCTC CTGACCACGG ACGTTTCCAT CAGGTTCCAT CCCGAAAATC<br>TCTCGGTTCC ACGTCCCCCT GGGGCTTCTC CTGACCCAGT CCCCGTGCCC CGCCTCCCCG<br>AAACAGGCTA CTCTCCTCGG CCCCCTCCAT CGGGCTGAGG AAGCACAGCA GCATCTTCAA<br>ACATGTACAA AATCGATTGC CTTTAAACAC CCTTCACATA CCCTCCCCCC AAATTATCCC<br>CAATTATCCC CACACATAAA AAATCAAAAC ATTAAACTAA CCCCCTTCCC CCCCCCCCAC<br>AACAACCCTC TTAAAACTAA TTGGCTTTTT AGAACACCC CACAAAAGCT CAGAAATTGG<br>CTTTAAAAAA AACAACCACC AAAAAAAATC AATTGGCTAA AAAAAAAAAG TATTAAAAAC<br>GAATTGGCTG AGAAACAATT GGCAAAATAA AGGAATTTGG CACTCCCCAC CCCCCTCTTT<br>CTCTTCTCCC TTGGACTTTG AGTCAAATTG GCTGGACTT GAGTCCCTGA ACCAGCAAAG<br>AGAAAAGAAG GACCCCAGAA ATCACAGGTG GCACGTCGC TGCTACCGCC ATCTCCCTTC<br>TCACGGGAAT TTTCAGGGTA AACTGGCCAT CCGAAAATAG CAACAACCCA GACTGGCTCC<br>TCACTCCCTT TTCCATCACT AAAAATCACA GAGCAGTCAG AGGGACCCAG TAAGACCAAA<br>GGAGGGGAGG ACAGAGCATG AAAACCAAAA TCCATGCAAA TGAAATGTAA TTGGCACGAC<br>CCTCACCCCC AAATCTTACA TCTCAATTCC CATCCTAAAA AGCACTCATA CTTTATGCAT<br>CCCCGCAGCT ACACACACAC AACACACAGC ACACGCATGA ACACAGCACA CACACGAGCA<br>CAGCACACAC ACAAACGCAC AGCACACACA CACACACAGT GAGCACACAG CACACACACA<br>AACGCACAGC ACACACACGC ACACACATGC ACACACAGCA CACAAACGCA CGGCACACAC<br>ACGCACACAC ATGCACACAC AGCACACACA CAAACGCACA GCACACACAA ACGCACAGCA<br>CACACGCACA CACAGCACAC ACACGAGCAC ACAGCACACA AACGCACAGC ACACGCACAC<br>ACATGCACAC ACAGCACACA CACTAGCACA CAGCACACAC ACAAAGACAC AGCACACACA<br>TGCACACACA GCACACACAC GCGAACACAG CACACACGAA CACAGCACAC ACAGCACACA<br>CACAAACACA GCACACACAT GCACACAGCA CACGCACACA CAGCACACAC ATGAACACAG<br>CACACAGCAC ACACATGCAC ACAGCACACA CACGCATGCA CAGCACACAT GAACACAGCA<br>CACACACAAA CACAGCACAC ACACATGCAC ACACAGCACA CACACTCATG CGCAGCACAT<br>ACATGAACAC AGCTCACAGC ACACAAACAC GCAGCACACA CGTTGCACAC GCAAGCACCC<br>ACCTGCACAC ACACATGCGC ACACACACGC ACACCCCCAC AAAATTGGAT GAAAACAATA<br>AGCATATCTA AGCAACTACG ATATCTGTAT GGATCAGGCC AAAGTCCCGC TAAGATTCTC<br>CAATGTTTTC ATGGTCTGAG CCCCGCTCCT GTTCCCATCT CCACTGCCCC TCGGCCCTGT<br>CTGTGCCCTG CCTCTCAGAG GAGGGGGCTC AGATGGTGCG GCCTGAGTGT GCGGCCGGCG |

TABLE OF CERTAIN SEQUENCES

| SEQ ID NO | Description | Sequence |
|---|---|---|
| | | GCATTTGGGA TACACCCGTA GGGTGGGCGG GGTGTGTCCC AGGCCTAATT CCATCTTTCC<br>ACCATGACAG AGATGCCCTT GTGAGGCTGG CCTCCTTGGC GCCTGTCCCC ACGGCCCCCG<br>CAGCGTGAGC CACGATGCTC CCCATACCCC ACCCATTCCC GATACACCTT ACTTACTGTG<br>TGTTGGCCCA GCCAGAGTGA GGAAGGAGTT TGGCCACATT GGAGATGGCG GTAGCTGAGC<br>AGACATGCCC CCACGAGTAG CCTGACTCCC TGGTGTGCTC CTGGAAGGAA GATCTTGGGG<br>ACCCCCCCAC CGGAGCACAC CTAGGGATCA TCTTTGCCCG TCTCCTGGGG ACCCCCCAAG<br>AAATGTGGAG TCCTCGGGGG CCGTGCACTG ATGCGGGGAG TGTGGGAAGT CTGGCGGTTG<br>GAGGGGTGGG TGGGGGGCAG TGGGGGCTGG GCGGGGGGAG TTCTGGGGTA GGAAGTGGTC<br>CCGGGAGATT TTGGATGGAA AAGTCAGGAG GATTGACAGC AGACTTGCAG AATTACATAG<br>AGAAATTAGG AACCCCCAAA TTTCATGTCA ATTGATCTAT TCCCCCTCTT TGTTTCTTGG<br>GGCATTTTTC CTTTTTTTTT TTTTTTTGTT TTTTTTTTAC CCCTCCTTAG CTTTATGCGC<br>TCAGAAACCA AATTAAACCC CCCCCCCATG TAACAGGGGG GCAGTGACAA AAGCAAGAAC<br>GCACGAAGCC AGCCTGGAGA CCACCACGTC CTGCCCCCCG CCATTTATCG CCCTGATTGG<br>ATTTTGTTTT TCATCTGTCC CTGTTGCTTG GGTTGAGTTG AGGGTGGAGC CTCCTGGGGG<br>GCACTGGCCA CTGAGCCCCC TTGGAGAAGT CAGAGGGGAG TGGAGAAGGC CACTGTCCGG<br>CCTGGCTTCT GGGGACAGTG GCTGGTCCCC AGAAGTCCTG AGGGCGGAGG GGGGGGTTGG<br>GCAGGGTCTC CTCAGGTGTC AGGAGGGTGC TCGGAGGCCA CAGGAGGGGG CTCCTGGCTG<br>GCCTGAGGCT GGCCGGAGGG GAAGGGGCTA GCAGGTGTGT AAACAGAGGG TTCCATCAGG<br>CTGGGGCAGG GTGGCCGCCT TCCGCACACT TGAGGAACCC TCCCCTCTCC CTCGGTGACA<br>TCTTGCCCGC CCCTCAGCAC CCTGCCTTGT CTCCAGGAGG TCCGAAGCTC TGTGGGACCT<br>CTTGGGGCA AGGTGGGGTG AGGCCGGGGA GTAGGGAGGT CAGGCGGGTC TGAGCCCACA<br>GAGCAGGAGA GCTGCCAGGT CTGCCCATCG ACCAGGTTGC TTGGGCCCCG GAGCCCACGG<br>GTCTGGTGAT GCCATAGCAG CCACCACCGC GGCGCCTAGG GCTGCGGCAG GGACTCGGCC<br>TCTGGGAGGT TTACCTCGCC CCCACTTGTG CCCCCAGCTC AGCCCCCCTG CACGCAGCCC<br>GACTAGCAGT CTAGAGGCCT GAGGCTTCTG GGTCCTGGTG ACGGGGCTGG CATGACCCCG<br>GGGGTCGTCC ATGCCAGTCC GCCTCAGTCG CAGAGGGTCC CTCGGCAAGC GCCCTGTGAG<br>TGGGCCATTC GGAACATTGG ACAGAAGCCC AAAGAGCCAA ATTGTCACAA TTGTGGAACC<br>CACATTGGCC TGAGATCCAA AACGCTTCGA GGCACCCCAA ATTACCTGCC CATTCGTCAG<br>GACACCCACC CACCCAGTGT TATATTCTGC CTCGCCGGAG TGGGTGTTCC CGGGGGCACT<br>TGCCGACCAG CCCCTTGCGT CCCCAGGTTT GCAGCTCTCC CCTGGGCCAC TAACCATCCT<br>GGCCCGGGCT GCCTGTCTGA CCTCCGTGCC TAGTCGTGGC TCTCCATCTT GTCTCCTCCC<br>CGTGTCCCCA ATGTCTTCAG TGGGGGGCCC CCTCTTGGGT CCCCTCCTCT GCCATCACCT<br>GAAGACCCCC ACGCCAAACA CTGAATGTCA CCTGTGCCTG CCGCCTCGGT CCACCTTGCG<br>GCCCGTGTTT GACTCAACTC AACTCCTTTA ACGCTAATAT TTCCGGCAAA ATCCCATGCT<br>TGGGTTTTGT CTTTAACCTT GTAACGCTTG CAATCCCAAT AAAGCATTAA AAGTCATGAA<br>AAAAAAAAAA AAAAAA |
| 3 | Human IGF2 mRNA, transcript variant 1 | CGCCTGTCCC CCTCCCGAGG CCCGGGCTCG CGACGGCAGA GGGCTCCGTC GGCCCAAACC<br>GAGCTGGGCG CCCGCGGTCC GGGTGCAGCC TCCACTCCGC CCCCCAGTCA CCGCCTCCCC<br>CGGCCCCTCG ACGTGGCGCC CTTCCCTCCG CTTCTCTGTG CTCCCCGCGC CCCTCTTGGC<br>GTCTGGCCCC GGCCCCCGCT CTTTCTCCCG CAACCTTCCC TTCGCTCCCT CCCGTCCCCC<br>CCAGCTCCTA GCCTCCGACT CCCTCCCCCC CTCACGCCCG CCCTCTCGCC TTCGCCGAAC<br>CAAAGTGGAT TAATTACACG CTTTCTGTTT CTCTCCGTGC TGTTCTCTCC CGCTGTGCGC<br>CTGCCCGCCT CTCGCTGTCC TCTCTCCCCC TCGCCCTCTC TTCGGCCCCC CCCTTTCACG<br>TTCACTCTGT CTCTCCCACT ATCTCTGCCC CCCTCTATCC TTGATACAAC AGCTGACCTC<br>ATTTCCCGAT ACCTTTTCCC CCCCGAAAAG TACAACATCT GGCCCGCCCC AGCCCGAAGA<br>CAGCCCGTCC TCCCTGGACA ATCAGACGAA TTCTCCCCCC CCCCCCAAAA AAAAGCCATC<br>CCCCCGCTCT GCCCCGTCGC ACATTCGGCC CCCGCGACTC GGCCAGAGCG GCGCTGGCAG<br>AGGAGTGTCC GGCAGGAGGG CCAACGCCCG CTGTTCGGTT TGCGACACGC AGCAGGGAGG<br>TGGGCGGCAG CGTCGCCGGC TTCCAGACAC CAATGGGAAT CCCAATGGGG AAGTCGATGC<br>TGGTGCTTCT CACCTTCTTG GCCTTCGCCT CGTGCTGCAT TGCTGCTTAC CGCCCCAGTG<br>AGACCCTGTG CGGCGGGGAG CTGGTGGACA CCCTCCAGTT CGTCTGTGGG GACCGCGGCT<br>TCTACTTCAG CAGGCCCGCA AGCCGTGTGA GCCGTCGCAG CCGTGGCATC GTTGAGGAGT<br>GCTGTTTCCG CAGCTGTGAC CTGGCCCTCC TGGAGACGTA CTGTGCTACC CCCGCCAAGT<br>CCGAGAGGGA CGTGTCGACC CCTCCGACCG TGCTTCCGGA CAACTTCCCC AGATACCCCG<br>TGGGCAAGTT CTTCCAATAT GACACCTGGA AGCAGTCCAC CCAGCGCCTG CGCAGGGGCC<br>TGCCTGCCCT CCTGCGTGCC CGCCGGGGTC ACGTGCTCGC CAAGGAGCTC GAGGCGTTCA<br>GGGAGGCCAA ACGTCACCGT CCCTGATTG CTCTACCCAC CCAAGACCCC GCCCACGGGG<br>GCGCCCCCCC AGAGATGGCC AGCAATCGGA AGTGAGCAAA ACTGCCGCAA GTCTGCAGCC<br>CGGCGCCACC ATCCTGCAGC CTCCTCCTGA CCACGGACGT TTCCATCAGG TTCCATCCCG<br>AAAATCTCTC GGTTCCACGT CCCCCTGGGG CTTCTCCTGA CCCAGTCCCC GTGCCCCGCC<br>TCCCCGAAAC AGGCTACTCT CCTCGGCCCC CTCCATCGGG CTGAGGAAGC ACAGCAGCAT<br>CTTCAAACAT GTACAAAATC GATTGGCTTT AAACACCCTT CACATACCCT CCCCCCAAAT<br>TATCCCCAAT TATCCCCACA CATAAAAAAT CAAAACATTA AACTAACCCC CTTCCCCCCC<br>CCCACAACA ACCCTCTTAA AACTAATTGG CTTTTTAGAA ACACCCCACA AAAGCTCAGA<br>AATTGGCTTT AAAAAAAACA ACCACCAAAA AAAATCAATT GGCTAAAAAA AAAAAGTATT<br>AAAAACGAAT TGGCTGAGAA ACAATTGGCA AAATAAAGGA ATTTGGCACT CCCCACCCCC<br>CTCTTTCTCT TCTCCCTTGG ACTTTGAGTC AAATTGGCCT GGACTTGAGT CCCTGAACCA<br>GCAAAGAGAA AAGAAGGACC CCAGAAATCA CAGGTGGGCA CGTCGCTGCT ACCGCCATCT<br>CCCTTCTCAC GGGAATTTTC AGGGTAAACT GGCCATCCGA AAATAGCAAC AACCCAGACT<br>GGCTCCTCAC TCCCTTTTCC ATCACTAAAA ATCACAGAGC AGTCAGAGGG ACCCAGTAAG<br>ACCAAAGGAG GGGAGGACAG AGCATGAAAA CCAAAATCCA TGCAAATGAA ATGTAATTGG<br>CACGACCCTC ACCCCCAAAT CTTACATCTC AATTCCCATC CTAAAAAGCA CTCATACTTT<br>ATGCATCCCC GCAGCTACAC ACACACAACA CACAGCACAC GCATGAACAC AGCACACACA |

TABLE OF CERTAIN SEQUENCES

| SEQ ID NO | Description | Sequence |
|---|---|---|
| | | CGAGCACAGC ACACACACAA ACGCACAGCA CACACAGCAC ACAGATGAGC ACACAGCACA<br>CACACAAACG CACAGCACAC ACACGCACAC ACATGCACAC ACAGCACACA AACGCACGGC<br>ACACACACGC ACACACATGC ACACACAGCA CACACACAAA CGCACAGCAC ACACAAACGC<br>ACAGCACACA CGCACACACA GCACACACAC GAGCACACAG CACACAAACG CACAGCACAC<br>GCACACACAT GCACACACAG CACACACACT AGCACACAGC ACACACACAA AGACACAGCA<br>CACACATGCA CACACAGCAC ACACACGCGA ACACAGCACA CACGAACACA GCACACACAG<br>CACACACACA AACACAGCAC ACACATGCAC ACAGCACACG CACACACAGC ACACACATGA<br>ACACAGCACA CAGCACACAC ATGCACACAC AGCACACACG CATGCACAGC ACACATGAAC<br>ACAGCACACA CACAAACACA CAGCACACAC ATGCACACAC AGCACACACA CTCATGCGCA<br>GCACATACAT GAACACAGCT CACAGCACAC AAACACGCAG CACACACGTT GCACACGCAA<br>GCACCCACCT GCACACACAC ATGCGCACAC ACACGCACAC CCCCACAAAA TTGGATGAAA<br>ACAATAAGCA TATCTAAGCA ACTACGATAT CTGTATGGAT CAGGCCAAAG TCCCGCTAAG<br>ATTCTCCAAT GTTTTCATGG TCTGAGCCCC GCTCCTGTTC CCATCTCCAC TGCCCCTCGG<br>CCCTGTCTGT GCCCTGCCTC TCAGAGGAGG GGGCTCAGAT GGTGCGGCCT GAGTGTGCGG<br>CCGGCGGCAT TTGGGATACA CCCGTAGGGT GGGCGGGGTG TGTCCCAGGC CTAATTCCAT<br>CTTTCCACCA TGACAGAGAT GCCCTTGTGA GGCTGGCCTC CTTGGCGCCT GTCCCCACGG<br>CCCCCGCAGC GTGAGCCACG ATGCTCCCCA TACCCCACCC ATTCCCGATA CACCTTACTT<br>ACTGTGTGTT GGCCCAGCCA GAGTGAGGAA GGAGTTTGGC CACATTGGAG ATGGCGGTAG<br>CTGAGCAGAC ATGCCCCCAC GAGTAGCCTG ACTCCCTGGT GTGCTCCTGG AAGGAAGATC<br>TTGGGGACCC CCCCACCGGA GCACACCTAG GGATCATCTT TGCCCGTCTC CTGGGGACCC<br>CCCAAGAAAT GTGGAGTCCT CGGGGGCCGT GCACTGATGC GGGGAGTGTG GGAAGTCTGG<br>CGGTTGGAGG GGTGGGTGGG GGGCAGTGGG GGCTGGGCGG GGGGAGTTCT GGGGTAGGAA<br>GTGGTCCCGG GAGATTTTGG ATGGAAAAGT CAGGAGGATT GACAGCAGAC TTGCAGAATT<br>ACATAGAGAA ATTAGGAACC CCCAAATTTC ATGTCAATTG ATCTATTCCC CCTCTTTGTT<br>TCTTGGGGCA TTTTTCCTTT TTTTTTTTTT TTTGTTTTTT TTTTACCCCT CCTTAGCTTT<br>ATGCGCTCAG AAACCAAATT AAACCCCCCC CCCATGTAAC AGGGGGGCAG TGACAAAAGC<br>AAGAACGCAC GAAGCCAGCC TGGAGACCAC CACGTCCTGC CCCCCGCCAT TTATCGCCCT<br>GATTGGATTT TGTTTTTCAT CTGTCCCTGT TGCTTGGGTT GAGTTGAGGG TGGAGCCTCC<br>TGGGGGGCAC TGGCCACTGA GCCCCCTTGG AGAAGTCAGA GGGGAGTGGA GAAGGCCACT<br>GTCCGGCCTG GCTTCTGGGG ACAGTGGCTG GTCCCCAGAA GTCCTGAGGG CGGAGGGGGG<br>GGTTGGGCAG GGTCTCCTCA GGTGTCAGGA GGGTGCTCGG AGGCCACAGG AGGGGGCTCC<br>TGGCTGGCCT GAGGCTGGCC GGAGGGGAAG GGGCTAGCAG GTGTGTAAAC AGAGGGTTCC<br>ATCAGGCTGG GGCAGGGTGG CCGCCTTCCG CACACTTGAG GAACCCTCCC CTCTCCCTCG<br>GTGACATCTT GCCCGCCCCT CAGCACCCTG CCTTGTCTCC AGGAGGTCCG AAGCTCTGTG<br>GGACCTCTTG GGGGCAAGGT GGGGTGAGGC CGGGGAGTAG GGAGGTCAGG CGGGTCTGAG<br>CCCACAGAGC AGGAGAGCTG CCAGGTCTGC CCATCGACCA GGTTGCTTGG GCCCCGGAGC<br>CCACGGGTCT GGTGATGCCA TAGCAGCCAC CACCGCGGCG CCTAGGGCTG CGGCAGGGAC<br>TCGGCCTCTG GGAGGTTTAC CTCGCCCCCA CTTGTGCCCC CAGCTCAGCC CCCCTGCACG<br>CAGCCCGACT AGCAGTCTAG AGGCCTGAGG CTTCTGGGTC CTGGTGACGG GGCTGGCATG<br>ACCCCGGGGG TCGTCCATGC CAGTCCGCCT CAGTCGCAGA GGGTCCCTCG GCAAGCGCCC<br>TGTGAGTGGG CCATTCGGAA CATTGGACAG AAGCCCAAAG AGCCAAATTG TCACAATTGT<br>GGAACCCACA TTGGCCTGAG ATCCAAAACG CTTCGAGGCA CCCCAAATTA CCTGCCCATT<br>CGTCAGGACA CCCACCCACC CAGTGTTATA TTCTGCCTCG CCGGAGTGGG TGTTCCCGGG<br>GGCACTTGCC GACCAGCCCC TTGCGTCCCC AGGTTTGCAG CTCTCCCCTG GGCCACTAAC<br>CATCCTGGCC CGGGCTGCCT GTCTGACCTC CGTGCCTAGT CGTGGCTCTC CATCTTGTCT<br>CCTCCCCGTG TCCCCAATGT CTTCAGTGGG GGGCCCCCTC TTGGGTCCCC TCCTCTGCCA<br>TCACCTGAAG ACCCCCACGC CAAACACTGA ATGTCACCTG TGCCTGCCGC CTCGGTCCAC<br>CTTGCGGCCC GTGTTTGACT CAACTCAACT CCTTTAACGC TAATATTTCC GGCAAAATCC<br>CATGCTTGGG TTTTGTCTTT AACCTTGTAA CGCTTGCAAT CCCAATAAAG CATTAAAAGT<br>CATGAAAAAA AAAAAAAAAA AA |
| 4 | Human IGF2 mRNA, transcript variant 3 | GGCCGCGCGC CCTCAGGACG TGGACAGGGA GGGCTTCCCC GTGTCCAGGA AAGCGACCGG<br>GCATTGCCCC CAGTCTCCCC CAAATTTGGG CATTGTCCCC GGGTCTTCCA ACGGACTGGG<br>CGTTGCTCCC GGACACTGAG GACTGGCCCC GGGGTCTCGC TCACCTTCAG CAGCGTCCAC<br>CGCCTGCCAC AGAGCGTTCG ATCGCTCGCT GCCTGAGCTC CTGGTGCGCC CGCGGACGCA<br>GCCTCCAGCT TCGCGGAGAT GGTTTCCCCA GACCCCCAAA TTATCGTGGT GGCCCCCGAG<br>ACCGAACTCG CGTCTATGCA AGTCCAACGC ACTGAGGACG GGTAACCAT TATCCAGATA<br>TTTTGGGTGG GCCGCAAAGG CGAGCTACTT AGACGCACCG CGGTGAGCTC GGCCATGCAG<br>ACACCAATGG GAATCCCAAT GGGGAAGTCG ATGCTGGTGC TTCTCACCTT CTTGGCCTTC<br>GCCTCGTGCT GCATTGCTGC TTACCGCCCC AGTGAGACCC TGTGCGGCGG GGAGCTGGTG<br>GACACCCTCC AGTTCGTCTG TGGGGACCGC GGCTTCTACT TCAGCAGGCC CGCAAGCCGT<br>GTGAGCCGTC GCAGCCGTGG CATCGTTGAG GAGTGCTGTT TCCGCAGCTG TGACCTGGCC<br>CTCCTGGAGA CGTACTGTGC TACCCCCGCC AAGTCCGAGA GGGACGTGTC GACCCCTCCG<br>ACCGTGCTTC CGGACAACTT CCCCAGATAC CCCGTGGGCA AGTTCTTCCA ATATGACACC<br>TGGAAGCAGT CCACCCAGCC CCTGCGCAGG GGCCTGCCTG CCCTCCTGCG TGCCCGCCGG<br>GGTCACGTGC TCGCCAAGGA GCTCGAGGCG TTCAGGGAGG CCAAACGTCA CCGTCCCCTG<br>ATTGCTCTAC CCACCCAAGA CCCCGCCCAC GGGGGCGCCC CCCAGAGAT GGCCAGCAAT<br>CGGAAGTGAG CAAAACTGCC GCAAGTCTGC AGCCCGGCGC CACCATCCTG CAGCCTCCTC<br>CTGACCACGG ACGTTTCCAT CAGGTTCCAT CCCGAAAATC TCTCGGTTCC ACGTCCCCCT<br>GGGGCTTCTC CTGACCCAGT CCCCGTGCCC CGCCTCCCCG AAACAGGCTA CTCTCCTCGG<br>CCCCCTCCAT CGGGCTGAGG AAGCACAGCA GCATCTTCAA ACATGTACAA AATCGATTGG<br>CTTTAAACAC CCTTCACATA CCCTCCCCCC AAATTATCCC CAATTATCCC CACACATAAA<br>AAATCAAAAC ATTAAACTAA CCCCCTTCCC CCCCCCCCAC AACAACCCTC TTAAAACTAA<br>TTGGCTTTTT AGAAACACCC CACAAAAGCT CAGAAATTGG CTTTAAAAAA AACAACCACC |

TABLE OF CERTAIN SEQUENCES

| SEQ ID NO | Description | Sequence |
|---|---|---|
| | | AAAAAAAATC AATTGGCTAA AAAAAAAAAG TATTAAAAAC GAATTGGCTG AGAAACAATT
GGCAAAATAA AGGAATTTGG CACTCCCCAC CCCCCTCTTT CTCTTCTCCC TTGGACTTTG
AGTCAAATTG GCCTGGACTT GAGTCCCTGA ACCAGCAAAG AGAAAAGAAG GACCCCAGAA
ATCACAGGTG GGCACGTCGC TGCTACCGCC ATCTCCCTTC TCACGGGAAT TTTCAGGGTA
AACTGGCCAT CCGAAAATAG CAACAACCCA GACTGGCTCC TCACTCCCTT TTCCATCACT
AAAAATCACA GAGCAGTCAG AGGGACCCAG TAAGACCAAA GGAGGGGAGG ACAGAGCATG
AAAACCAAAA TCCATGCAAA TGAAATGTAA TTGGCACGAC CCTCACCCCC AAATCTTACA
TCTCAATTCC CATCCTAAAA AGCACACACA CTTTATGCAT CCCCGCAGCT ACACACACAC
AACACACAGC ACACGCATGA ACACAGCACA CACACGAGCA CAGCACACAC ACAAACGCAC
AGCACACACA GCACACAGAT GAGCACACAG CACACACACA AACGCACAGC ACACACACGC
ACACACATGC ACACACAGCA CACAAACGCA CGGCACACAC ACGCACACAC ATGCACACAC
AGCACACACA CAAACGCACA GCACACACAA ACGCACAGCA CACGCACA CACAGCACAC
ACACGAGCAC ACAGCACACA AACGCACAGC ACACGCACAC ACATGCACAC ACAGCACACA
CACTAGCACA CAGCACACAC ACAAAGACAC AGCACACACA TGCACACACA GCACACACAC
GCGAACACAG CACACACGAA CACAGCACAC ACAGCACACA CACAAACACA GCACACACAT
GCACACAGCA CACGCACACA CAGCACACAC ATGAACACAG CACACAGCAC ACACATGCAC
ACACAGCACA CACGCATGCA CACACACAT GAACACAGCA CACACACAAA CACACAGCAC
ACACATGCAC ACACAGCACA CACACTCATG CGCAGCACAT ACATGAACAC AGCTCACAGC
ACACAAACAC GCAGCACACA CGTTGCACAC GCAAGCACCC ACCTGCACAC ACACATGCGC
ACACACACGC ACACCCCCAC AAAATTGGAT GAAAACAATA AGCATATCTA AGCAACTACG
ATATCTGTAT GGATCAGGCC AAAGTCCCGC TAAGATTCTC CAATGTTTTC ATGGTCTGAG
CCCCGCTCCT GTTCCCATCT CCACTGCCCC TCGGCCCTGT CTGTGCCCTG CCTCTCAGAG
GAGGGGGCTC AGATGGTGCG GCCTGAGTGT GCGGCCGGCG GCATTTGGGA TACACCCGTA
GGGTGGGCGG GGTGTGTCCC AGGCCTAATT CCATCTTTCC ACCATGCAG AGATGCCCTT
GTGAGGCTGG CCTCCTTGGC GCCTGTCCCC ACGGCCCCCG CAGCGTGAGC CACGATGCTC
CCCATACCCC ACCCATTCCC GATACACCTT ACTTACTGTG TGTTGGCCCA GCCAGAGTGA
GGAAGGAGTT TGGCCACATT GGAGATGGCG GTAGCTGAGC AGACATGCCC CCACGAGTAG
CCTGACTCCC TGGTGTGCTC CTGGAAGGAA GATCTTGGGG ACCCCCCCAC CGGAGCACAC
CTAGGGATCA TCTTTGCCCG TCTCCTGGGG ACCCCCCAAG AAATGTGGAG TCCTCGGGGG
CCGTGCACTG ATGCGGGGAG TGTGGGAAGT CTGGCGGTTG GAGGGGTGGG TGGGGGGCAG
TGGGGGCTGG GCGGGGGAG TTCTGGGGTA GGAAGTGGTC CCGGGAGATT TTGGATGGAA
AAGTCAGGAG GATTGACAGC AGACTTGCAG AATTACATAG AGAAATTAGG AACCCCCAAA
TTTCATGTCA ATTGATCTAT TCCCCCTCTT TGTTTCTTGG GGCATTTTTC CTTTTTTTTT
TTTTTTTGTT TTTTTTTAC CCCTCCTTAG CTTTATGCGC TCAGAAACCA AATTAAACCC
CCCCCCCATG TAACAGGGGG GCAGTGACAA AAGCAAGAAC GCACGAAGCC AGCCTGGAGA
CCACCACGTC CTGCCCCCG CCATTTATCG CCCTGATTGG ATTTTGTTTT TCATCTGTCC
CTGTTGCTTG GGTTGAGTTG AGGGTGGAGC CTCCTGGGGG GCACTGGCCA CTGAGCCCCC
TTGGAGAAGT CAGAGGGGAG TGGAGAAGGC CACTGTCCGG CCTGGCTTCT GGGGACAGTG
GCTGGTCCCC AGAAGTCCTG AGGGCGGAGG GGGGGGTTGG GCAGGGTCTC CTCAGGTGTC
AGGAGGGTGC TCGGAGGCCA CAGGAGGGGG CTCCTGGCTG GCCTGAGGCT GGCCGGAGGG
GAAGGGGCTA GCAGGTGTGT AAACAGAGGG TTCCATCAGG CTGGGGCAGG GTGGCCGCCT
TCCGCACACT TGAGGAACCC TCCCCTCTCC CTCGGTGACA TCTTGCCCGC CCCTCAGCAC
CCTGCCTTGT CTCCAGGAGG TCCGAAGCTC TGTGGGACCT CTTGGGGGCA AGGTGGGGTG
AGGCCGGGGA GTAGGGAGGT CAGGCGGGTC TGAGCCCACA GAGCAGGAGA GCTGCCAGGT
CTGCCCATCG ACCAGGTTGC TTGGGCCCCG GAGCCCACGG GTCTGGTGAT GCCATAGCAG
CCACCACCGC GGCGCCTAGG GCTGCGGCAG GGACTCGGCC TCTGGGAGGT TTACCTCGCC
CCCACTTGTG CCCCCAGCTC AGCCCCCCTG CACGCAGCCC GACTAGCAGT CTAGAGGCCT
GAGGCTTCTG GGTCCTGGTG ACGGGGCTGG CATGACCCCG GGGTCGTCC ATGCCAGTCC
GCCTCAGTCG CAGAGGGTCC CTCGGCAAGC GCCCTGTGAG TGGGCCATTC GGAACATTGG
ACAGAAGCCC AAAGAGCCAA ATTGTCACAA TTGTGGAACC CACATTGGCC TGAGATCCAA
AACGCTTCGA GGCACCCCAA ATTACCTGCC CATTCGTCAG GACACCCACC CACCCAGTGT
TATATTCTGC CTCGCCGGAG TGGGTGTTCC CGGGGGCACT TGCCGACCAG CCCCTTGCGT
CCCCAGGTTT GCAGCTCTCC CCTGGGCCAC TAACCATCCT GGCCCGGGCT GCCTGTCTGA
CCTCCGTGCC TAGTCGTGGC TCTCCATCTT GTCTCCTCCC CGTGTCCCA ATGTCTTCAG
TGGGGGGCCC CCTCTTGGGT CCCCTCCTCT GCCATCACCT GAAGACCCCC ACGCCAAACA
CTGAATGTCA CCTGTGCCTG CCGCCTCGGT CCACCTTGCG GCCCGTGTTT GACTCAACTC
AACTCCTTTA ACGCTAATAT TTCCGGCAAA ATCCCATGCT TGGGTTTTGT CTTTAACCTT
GTAACGCTTG CAATCCCAAT AAAGCATTAA AAGTCATGAA AAAAAAAAAA AAAAAA |
| 5 | Human KRT20 mRNA | GAGACACACT CTGCCCCAAC CATCCTGAAG CTACAGGTGC TCCCTCCTGG AATCTCCAAT
GGATTTCAGT CGCAGAAGCT TCCACAGAAG CCTGAGCTCC TCCTTGCAGG CCCCTGTAGT
CAGTACAGTG GGCATGCAGC GCCTCGGGAC GACACCCAGC GTTTATGGGG GTGCTGGAGG
CCGGGGCATC CGCATCTCCA ACTCCAGACA CACGGTGAAC TATGGGAGCG ATCTCACAGG
CGGCGGGGAC CTGTTTGTTG GCAATGAGAA AATGGCCATG CAGAACCTAA ATGACCGTCT
AGCGAGCTAC CTAGAAAAGG TGCGGACCCT GGAGCAGTCC AACTCCAAAC TTGAAGTGCA
AATCAAGCAG TGGTACGAAA CCAACGCCCC GAGGGCTGGT CGCGACTACA GTGCATATTA
CAGACAAATT GAAGAGCTGC GAAGTCAGAT TAAGGATGCT CAACTGCAAA ATGCTCGGTG
TGTCCTGCAA ATTGATAATG CTAAACTGGC TGCTGAGGAC TTCAGACTGA AGTATGAGAC
TGAGAGAGGA ATACGTCTAA CAGTGGAAGC TGATCTCCAA GGCCTGAATA AGGTCTTTGA
TGACCTAACC CTACATAAAA CAGATTTGGA GATTCAAATT GAAGAACTGA ATAAAGACCT
AGCTCTCCTC AAAAAGGAGC ATCAGGAGGA AGTCGATGGC CTACACAAGC ATCTGGGCAA
CACTGTCAAT GTGGAGGTTG ATGCTGCTCC AGGCCTGAAC CTTGGCGTCA TCATGAATGA
AATGAGGCAG AAGTATGAAG TCATGGCCCA GAAGAACCTT CAAGAGGCCA AGAACAGTT
TGAGAGACAG ACTGCAGTTC TGCAGCAACA GGTCACAGTG AATACTGAAG AATTAAAAGG |

TABLE OF CERTAIN SEQUENCES

| SEQ ID NO | Description | Sequence |
|---|---|---|
| | | AACTGAGGTT CAACTAACGG AGCTGAGACG CACCTCCCAG AGCCTTGAGA TAGAACTCCA GTCCCATCTC AGCATGAAAG AGTCTTTGGA GCACACTCTA GAGGAGACCA AGGCCCGTTA CAGCAGCCAG TTAGCCAACC TCCAGTCGCT GTTGAGCTCT CTGGAGGCCC AACTGATGCA GATTCGGAGT AACATGGAAC GCCAGAACAA CGAATACCAT ATCCTTCTTG ACATAAAGAC TCGACTTGAA CAGGAAATTG CTACTTACCG CCGCCTTCTG GAAGGAGAAG ACGTAAAAAC TACAGAATAT CAGTTAAGCA CCCTGGAAGA GAGAGATATA AAGAAAACCA GGAAGATTAA GACAGTCGTG CAAGAAGTAG TGGATGGCAA GGTCGTGTCA TCTGAAGTCA AAGAGGTGGA AGAAAATATC TAAATAGCTA CCAGAAGGAG ATGCTGCTGA GGTTTTGAAA GAAATTTGGC TATAATCTTA TCTTTGCTCC CTGCAAGAAA TCAGCCATAA GAAAGCACTA TTAATACTCT GCAGTGATTA GAAGGGGTGG GGTGGCGGGA ATCCTATTTA TCAGACTCTG TAATTGAATA TAAATGTTTT ACTCAGAGGA GCTGCAAATT GCCTGCAAAA ATGAAATCCA GTGAGCACTA GAATATTTAA AACATCATTA CTGCCATCTT TATCATGAAG CACATCAATT ACAAGCTGTA GACCACCTAA TATCAATTTG TAGGTAATGT TCCTGAAAAT TGCAATACAT TTCAATTATA CTAAACCTCA CAAAGTAGAG GAATCCATGT AAATTGCAAA TAAACCACTT TCTAATTTTT TCCTGTTTCT GAATTGTAAA ACCCCCTTTG GGAGTCCCTG GTTTCTTATT GAGCCAATTT CTGGG |
| 6 | Human ANXA10 mRNA | ATCCAGATTT GCTTTTACAT TTTCTTGCCT GAGTCTGAGG TGAACAGTGA ACATATTTAC ATTTGATTTA ACAGTGAACC TTAATTCTTT CTGGCTTCAC AGTGAAACAA GTTTATGCAA TCGATCAAAT ATTTTCATCC CTGAGGTTAA CAATTACCAT CAAAATGTTT TGTGGAGACT ATGTGCAAGG AACCATCTTC CCAGCTCCCA ATTTCAATCC CATAATGGAT GCCCAAATGC TAGGAGGAGC ACTCCAAGGA TTTGACTGTG ACAAAGACAT GCTGATCAAC ATTCTGACTC AGCGCTGCAA TGCACAAAGG ATGATGATTG CAGAGGCATA CCAGAGCATG TATGGCCGGG ACCTGATTGG GGATATGAGG GAGCAGCTTT CGGATCACTT CAAAGATGTG ATGGCTGGCC TCATGTACCC ACCACCACTG TATGATGCTC ATGAGCTCTG GCATGCCATG AAGGGAGTAG GCACTGATGA GAATTGCCTC ATTGAAATAC TAGCTTCAAG AACAAATGGA GAAATTTTCC AGATGCGAGA AGCCTACTGC TTGCAATACA GCAATAACCT CAAGAGGAC ATTTATTCAG AGACCTCAGG ACACTTCAGA GATACTCTCA TGAACTTGGT CCAGGGGACC AGAGAGGAAG GATATACAGA CCCTGCGATG GCTGCTCAGG ATGCAATGGT CCTATGGGAA GCCTGTCAGC AGAAGACGGG GGAGCACAAA ACCATGCTGC AAATGATCCT GTGCAACAAG AGCTACCAGC AGCTGCGGCT GGTTTTCCAG GAATTTCAAA ATATTTCTGG GCAAGATATG GTAGATGCCA TTAATGAATG TTATGATGGA TACTTTCAGG AGCTGCTGGT TGCAATTGTT CTCTGTGTTC GAGACAAACC AGCCTATTTT GCTTATAGAT TATATAGTGC AATTCATGAC TTTGGTTTCC ATAATAAAAC TGTAATCAGG ATTCTCATTG CCAGAAGTGA AATAGACCTG CTGACCATAA GGAAACGATA CAAAGAGCGA TATGGAAAAT CCCTATTTCA TGATATCAGA AATTTTGCTT CAGGGCATTA TAAGAAAGCA CTGCTTGCCA TCTGTGCTGG TGATGCTGAG GACTACTAAA ATGAAGAGGA CTTGGAGTAC TGTGCACTCC TCTTTCTAGA CACTTCCAAA TAGAGATTTT CTCACAAATT TGTACTGTTC ATGGCACTAT TAACAAAACT ATACAATCAT ATTTTCTCTT CTATCTTTGA AATTATTCTA AGCCAAAGAA AACTATGAAT GAAAGTATAT GATACTGAAT TTGCCTACTA TCCTGAATTT GCCTACTATC TAATCAGCAA TTAAATAAAT TGTGCATGAT GGAATAATAG AAAAATTGCA TTGGAATAGA TTTTATTTAA ATGTGAACCA TCAACAACCT ACAACAA |
| 7 | Human ABL mRNA | GGTTGGTGAC TTCCACAGGA AAAGTTCTGG AGGAGTAGCC AAAGACCATC AGCGTTTCCT TTATGTGTGA GAATTGAAAT GACTAGCATT ATTGACCCTT TTCAGCATCC CCTGTGAATA TTTCTGTTTA GGTTTTTCTT CTTGAAAAGA AATTGTTATT CAGCCCGTTT AAAACAAATC AAGAAACTTT TGGGTAACAT TGCAATTACA TGAAATTGAT AACCGCGAAA ATAATTGGAA CTCCTGCTTG CAAGTGTCAA CCTAAAAAAA GTGCTTCCTT TTGTTATGGA AGATGTCTTT CTGTGATTGA CTTCAATTGC TGACTTGTGG AGATGCAGCG AATGTGAAAT CCCACGTATA TGCCATTTCC CTCTACGCTC GCTGACCGTT CTGGAAGATC TTGAACCCTC TTCTGGAAAG GGGTACCTAT TATTACTTTA TGGGGCAGCA GCCTGGAAAA GTACTTGGGG ACCAAAGAAG GCCAAGCTTG CCTGCCCTGC ATTTTATCAA AGGAGCAGGG AAGAAGGAAT CATCGAGGCA TGGGGGTCCA CACTGCAATG TTTTTGTGGA ACATGAAGCC CTTCAGCGGC CAGTAGCATC TGACTTTGAG CCTCAGGGTC TGAGTGAAGC CGCTCGTTGG AACTCCAAGG AAAACCTTCT CGCTGGACCC AGTGAAAATG ACCCCAACCT TTTCGTTGCA CTGTATGATT TTGTGGCCAG TGGAGATAAC ACTCTAAGCA TAACTAAAGG TGAAAAGCTC CGGGTCTTAG GCTATAATCA CAATGGGGAA TGGTGTGAAG CCCAAACCAA AAATGGCCAA GGCTGGGTCC CAAGCAACTA CATCACGCCA GTCAACAGTC TGGAGAAACA CTCCTGGTAC CATGGGCCTG TGTCCCGCAA TGCCGCTGAG TATCTGCTGA GCAGCGGGAT CAATGGCAGC TTCTTGGTGC GTGAGAGTGA GAGCAGTCCT GGCCAGAGGT CCATCTCGCT GAGATACGAA GGGAGGGTGT ACCATTACAG GATCAACACT GCTTCTGATG GCAAGCTCTA CGTCTCCTCC GAGAGCCGCT TCAACACCCT GGCCGAGTTG GTTCATCATC ATTCAACGGT GGCCGACGGG CTCATCACCA CGCTCCATTA TCCAGCCCCA AAGCGCAACA AGCCCACTGT CTATGGTGTG TCCCCCAACT ACGACAAGTG GGAGATGGAA CGCACGGACA TCACCATGAA GCACAAGCTG GGCGGGGGCC AGTACGGGGA GGTGTACGAG GGCGTGTGGA AGAAATACAG CCTGACGGTG GCCGTGAAGA CCTTGAAGGA GGACACCATG GAGGTGGAAG AGTTCTTGAA AGAAGCTGCA GTCATGAAAG AGATCAAACA CCCTAACCTG GTGCAGCTCC TTGGGGTCTG CACCCGGGAG CCCCCGTTCT ATATCATCAC TGAGTTCATG ACCTACGGGA ACCTCCTGGA CTACCTGAGG GAGTGCAACC GGCAGGAGGT GAACGCCGTG GTGCTGCTGT ACATGGCCAC TCAGATCTCG TCAGCCATGG AGTACCTGGA GAAGAAAAAC TTCATCCACA GAGATCTTGC TGCCCGAAAC TGCCTGGTAG GGGAGAACCA CTTGGTGAAG GTAGCTGATT TTGGCCTGAG CAGGTTGATG ACAGGGGACA CCTACACAGC CCATGCTGGA GCCAAGTTCC CCATCAAATG GACTGCACCC GAGAGCCTGG CCTACAACAA GTTCTCCATC AAGTCCGACG TCTGGGCATT TGGAGTATTG CTTTGGGAAA TTGCTACCTA TGGCATGTCC CCTTACCCGG GAATTGACCT GTCCCAGGTG TATGAGCTGC TAGAGAAGGA |

TABLE OF CERTAIN SEQUENCES

| SEQ ID NO | Description | Sequence |
|---|---|---|
| | | CTACCGCATG GAGCGCCCAG AAGGCTGCCC AGAGAAGGTC TATGAACTCA TGCGAGCATG<br>TTGGCAGTGG AATCCCTCTG ACCGGCCCTC CTTTGCTGAA ATCCACCAAG CCTTTGAAAC<br>AATGTTCCAG GAATCCAGTA TCTCAGACGA AGTGGAAAAG GAGCTGGGGA AACAAGGCGT<br>CCGTGGGGCT GTGAGTACCT TGCTGCAGGC CCCAGAGCTG CCCACCAAGA CGAGGACCTC<br>CAGGAGAGCT GCAGAGCACA GAGACACCAC TGACGTGCCT GAGATGCCTC ACTCCAAGGG<br>CCAGGGAGAG AGCGATCCTC TGGACCATGA GCCTGCCGTG TCTCCATTGC TCCCTCGAAA<br>AGAGCGAGGT CCCCCGGAGG GCGGCCTGAA TGAAGATGAG CGCCTTCTCC CCAAAGACAA<br>AAAGACCAAC TTGTTCAGCG CCTTGATCAA GAAGAAGAAG AAGACAGCCC CAACCCCTCC<br>CAAACGCAGC AGCTCCTTCC GGGAGATGGA CGGCCAGCCG GAGCGCAGAG GGGCCGGCGA<br>GGAAGAGGGC CGAGACATCA GCAACGGGGC ACTGGCTTTC ACCCCCTTGG ACACAGCTGA<br>CCCAGCCAAG TCCCCAAAGC CCAGCAATGG GGCTGGGGTC CCCAATGGAG CCCTCCGGGA<br>GTCCGGGGGC TCAGGCTTCC GGTCTCCCCA CCTGTGGAAG AAGTCCAGCA CGCTGACCAG<br>CAGCCGCCTA GCCACCGGCG AGGAGGAGGG CGGTGGCAGC TCCAGCAAGC GCTTCCTGCG<br>CTCTTGCTCC GCCTCCTGCG TTCCCCATGG GGCCAAGGAC ACGGAGTGGA GGTCAGTCAC<br>GCTGCCTCGG GACTTGCAGT CCACGGGAAG ACAGTTTGAC TCGTCCACAT TTGGAGGGCA<br>CAAAAGTGAG AAGCCGGCTC TGCCTCGAA GAGGGCAGGG GAGAACAGGT CTGACCAGGT<br>GACCCGAGGC ACAGTAACGC CTCCCCCCAG GCTGGTGAAA AAGAATGAGG AAGCTGCTGA<br>TGAGGTCTTC AAAGACATCA TGGAGTCCAG CCCGGGCTCC AGCCCGCCCA ACCTGACTCC<br>AAAACCCCTC CGGCGGCAGG TCACCGTGGC CCCTGCCTCG GCCTCCCCC ACAAGGAAGA<br>AGCTGGAAAG GGCAGTGCCT TAGGGACCCC TGCTGCAGCT GAGCCAGTGA CCCCCACCAG<br>CAAAGCAGGC TCAGGTGCAC CAGGGGGCAC CAGCAAGGGC CCCGCCGAGG AGTCCAGAGT<br>GAGGAGGCAC AAGCACTCCT CTGAGTCGCC AGGGAGGGAC AAGGGGAAAT TGTCCAGGCT<br>CAAACCTGCC CCGCCGCCCC CACCAGCAGC CTCTGCAGGG AAGGCTGGAG GAAAGCCCTC<br>GCAGAGCCCG AGCCAGGAGG CGGCCGGGGA GGCAGTCCTG GGCGCAAAGA CAAAAGCCAC<br>GAGTCTGGTT GATGCTGTGA ACAGTGACGC TGCCAAGCCC AGCCAGCCGG GAGAGGGCCT<br>CAAAAAGCCC GTGCTCCCGG CCACTCCAAA GCCACAGTCC GCCAAGCCGT CGGGGACCCC<br>CATCAGCCCA GCCCCCGTTC CTCCACGTT GCCATCAGCA TCCTCGGCCC TGGCAGGGGA<br>CCAGCCGTCT TCCACCGCCT TCATCCCTCT CATATCAACC CGAGTGTCTC TTCGGAAAAC<br>CCGCCAGCCT CCAGAGCGGA TCGCCAGCGG CGCCATCACC AAGGGCGTGG TCCTGGACAG<br>CACCGAGGCG CTGTGCCTCG CCATCTCTAG GAACTCCGAG CAGATGGCCA GCCACAGCGC<br>AGTGCTGGAG GCCGGCAAAA ACCTCTACAC GTTCTGCGTG AGCTATGTGG ATTCCATCCA<br>GCAAATGAGG AACAAGTTTG CCTTCCGAGA GGCCATCAAC AAACTGGAGA ATAATCTCCG<br>GGAGCTTCAG ATCTGCCCGG CGACAGCAGG CAGTGGTCCA GCGGCCACTC AGGACTTCAG<br>CAAGCTCCTC AGTTCGGTGA AGGAAATCAG TGACATAGTG CAGAGGTAGC AGCAGTCAGG<br>GGTCAGGTGT CAGGCCCGTC GGAGCTGCCT GCAGCACATG CGGGCTCGCC CATACCCGTG<br>ACAGTGGCTG ACAAGGGACT AGTGAGTCAG CACCTTGGCC CAGGAGCTCT GCGCCAGGCA<br>GAGCTGAGGG CCCTGTGGAG TCCAGCTCTA CTACCTACGT TTGCACCGCC TGCCCTCCCG<br>CACCTTCCTC CTCCCCGCTC CGTCTCTGTC CTCGAATTTT ATCTGTGGAG TTCCTGCTCC<br>GTGGACTGCA GTCGGCATGC CAGGACCCGC CAGCCCCGCT CCCACCTAGT GCCCCAGACT<br>GAGCTCTCCA GGCCAGGTGG GAACGGCTGA TGTGGACTGT CTTTTTCATT TTTTTCTCTC<br>TGGAGCCCCT CCTCCCCCGG CTGGGCCTCC TTCTTCCACT TCTCCAAGAA TGGAAGCCTG<br>AACTGAGGCC TTGTGTGTCA GGCCCTCTGC CTGCACTCCC TGGCCTTGCC CGTCGTGTGC<br>TGAAGACATG TTTCAAGAAC CGCATTTCGG GAAGGGCATG CACGGGCATG CACACGGCTG<br>GTCACTCTGC CCTCTGCTGC TGCCCGGGGT GGGGTGCACT CGCCATTTCC TCACGTGCAG<br>GACAGCTCTT GATTTGGGTG GAAAACAGGG TGCTAAAGCC AACCAGCCTT TGGGTCCTGG<br>GCAGGTGGGA GCTGAAAAGG ATCGAGGCAT GGGGCATGTC CTTTCCATCT GTCCACATCC<br>CCAGAGCCCA GCTCTTGCTC TCTTGTGACG TGCACTGTGA ATCCTGGCAA GAAAGCTTGA<br>GTCTCAAGGG TGGCAGGTCA CTGTCACTGC CGACATCCCT CCCCCAGCAG AATGGAGGCA<br>GGGGACAAGG GAGGCAGTGG CTAGTGGGGT GAACAGCTGG TGCCAAATAG CCCCAGACTG<br>GGCCCAGGCA GGTCTGCAAG GGCCCAGAGT GAACCGTCCT TTCACACATC TGGGTGCCCT<br>GAAAGGGCCC TTCCCCTCCC CCACTCCTCT AAGACAAAGT AGATTCTTAC AAGGCCCTTT<br>CCTTTGGAAC AAGACAGCCT TCACTTTTCT GAGTTCTTGA AGCATTTCAA AGCCCTGCCT<br>CTGTGTAGCC GCCCTGAGAG AGAATAGAGC TGCCACTGGG CACCTGCGCA CAGGTGGGAG<br>GAAAGGGCCT GGCCAGTCCT GGTCCTGGCT GCACTCTTGA ACTGGGCGAA TGTCTTATTT<br>AATTACCGTG AGTGACATAG CCTCATGTTC TGTGGGGGTC ATCAGGGAGG GTTAGGAAAA<br>CCACAAACGG AGCCCCTGAA AGCCTCACGT ATTTCACAGA GCACGCCTGC CATCTTCTCC<br>CCGAGGCTGC CCCAGGCCGG AGCCCAGATA CGGGGGCTGT GACTCTGGGC AGGGACCCGG<br>GGTCTCCTGG ACCTTGACAG AGCAGCTAAC TCCGAGAGCA GTGGGCAGGT GGCCGCCCCT<br>GAGGCTTCAC GCCGGGAGAA GCCACCTTCC CACCCCTTCA TACCGCCTCG TGCCAGCAGC<br>CTCGCACAGG CCCTAGCTTT ACGCTCATCA CCTAAACTTG TACTTTATTT TTCTGATAGA<br>AATGGTTTCC TCTGGATCGT TTTATGCGGT TCTTACAGCA CATCACCTCT TTGCCCCCGA<br>CGGCTGTGAC GCAGCCGGAG GGAGGCACTA GTCACCGACA GCGGCCTTGA AGACAGAGCA<br>AAGCGCCCAC CCAGGTCCCC CGACTGCCTG TCTCCATGAG GTACTGGTCC CTTCCTTTTG<br>TTAACGTGAT GTGCCACTAT ATTTTACACG TATCTCTTGG TATGCATCTT TTATAGACGC<br>TCTTTTCTAA GTGGCGTGTG CATAGCGTCC TGCCCTGCCC CCTCGGGGGC CTGTGGTGGC<br>TCCCCCTCTG CTTCTCGGGG TCCAGTGCAT TTTGTTTCTG TATATGATTC TCTGTGGTTT<br>TTTTTGAATC CAAATCTGTC CTCTGTAGTA TTTTTTAAAT AAATCAGTGT TTACATTAGA<br>A |
| 47 | Armored RNA ® sequence | GAUGCUCACU UCAUCUAUGG UUACCCUGGG ACUUUACAC CAACAGAACU AGCAUCAUCC<br>UCUGCAUGGU CAGGUCAUGG AUCGGCAUCC UGACAGUUUC GGGAUUAGG CAUCUGCAGU<br>CUUACUGCUC AUCGGCUGAU GAUGCUGCUG UAAUCCCCAU CCAAGCAAGC UUGUGAUCCU<br>CCGCCAUUAU CCCAAAUGGU AUAACAUUUA GGACUAAAAG CUAUGCAAUU AUCACCUUGU<br>UUUUCAACAG CAAGACCUAA UAUUUCUUU UCAUCAUUAA UGCCUUUUGA UGGAUCAGGC |

TABLE OF CERTAIN SEQUENCES

| SEQ ID NO | Description | Sequence |
|---|---|---|
| | | AACCAUUUAU AAAUAUGUUC ACCAGCCGAA GUCAGUAGUG AUUGGGUGGU UCCUGGCUUG GGAUCAUGCC GCUGCAGAGG CUAUUCUCCU CUUGGCAGAU UGUCUGUAGC CGAGAAGGCG GAGUCUGGCA AUGAUGAUGC AUACAGUGUA CGACAGCCUU AGGGACUGGA GCUCAAGCAG UGUUUCCUCA ACCAGUCACA |
| 49 | Human androgen receptor (AR) mRNA, transcript variant 1 (GenBank NM_000044.3) | CGAGATCCCG GGGAGCCAGC TTGCTGGGAG AGCGGGACGG TCCGGAGCAA GCCCAGAGGC AGAGGAGGCG ACAGAGGGAA AAAGGGCCGA GCTAGCCGCT CCAGTGCTGT ACAGGAGCCG AAGGGACGCA CCACGCCAGC CCCAGCCCGG CTCCAGCGAC AGCCAACGCC TCTTGCAGCG CGGCGGCTTC GAAGCCGCCG CCCGGAGCTG CCCTTTCCTC TTCGGTGAAG TTTTTAAAAG CTGCTAAAGA CTCGGAGGAA GCAAGGAAAG TGCCTGGTAG GACTGACGGC TGCCTTTGTC CTCCTCCTCT CCACCCCGCC TCCCCCCACC CTGCCTTCCC CCCTCCCCC GTCTTCTCTC CCGCAGCTGC CTCAGTCGGC TACTCTCAGC CAACCCCCCT CACCACCCTT CTCCCCACCC GCCCCCCCGC CCCCGTCGGC CCAGCGCTGC CAGCCCGAGT TTGCAGAGAG GTAACTCCCT TTGGCTGCGA GCGGGCGAGC TAGCTGCACA TTGCAAAGAA GGCTCTTAGG AGCCAGGCGA CTGGGGAGCG GCTTCAGCAC TGCAGCCACG ACCCGCCTGG TTAGGCTGCA CGCGGAGAGA ACCCTCTGTT TTCCCCCACT CTCTCTCCAC CTCCTCCTGC CTTCCCCACC CCGAGTGCGG AGCCAGAGAT CAAAAGATGA AAAGGCAGTC AGGTCTTCAG TAGCCAAAAA ACAAAACAAA CAAAAACAAA AAAGCCGAAA TAAAAGAAAA AGATAATAAC TCAGTTCTTA TTTGCACCTA CTTCAGTGGA CACTGAATTT GGAAGGTGGA GGATTTTGTT TTTTTCTTTT AAGATCTGGG CATCTTTTGA ATCTACCCTT CAAGTATTAA GAGACAGACT GTGAGCCTAG CAGGGCAGAT CTTGTCCACC GTGTGTCTTC TTCTGCACGA GACTTTGAGG CTGTCAGAGC GCTTTTTGCG TGGTTGCTCC CGCAAGTTTC CTTCTCTGGA GCTTCCCGCA GGTGGGCAGC TAGCTGCAGC GACTACCGCA TCATCACAGC CTGTTGAACT CTTCTGAGCA AGAGAAGGGG AGGCGGGGTA AGGGAAGTAG GTGGAAGATT CAGCCAAGCT CAAGGATGGA AGTGCAGTTA GGGCTGGGAA GGGTCTACCC TCGGCCGCCG TCCAAGACCT ACCGAGGAGC TTTCCAGAAT CTGTTCCAGA GCGTGCGCGA AGTGATCCAG AACCCGGGCC CCAGGCACCC AGAGGCCGCG AGCGCAGCAC CTCCCGGCGC CAGTTTGCTG CTGCTGCAGC AGCAGCAGCA GCAGCAGCAG CAGCAGCAGC AGCAGCAGCA GCAGCAGCAG CAGCAGCAGC AGCAAGAGAC TAGCCCCAGG CAGCAGCAGC AGCAGCAGGG TGAGGATGGT TCTCCCCAAG CCCATCGTAG AGGCCCCACA GGCTACCTGG TCCTGGATGA GGAACAGCAA CCTTCACAGC CGCAGTCGGC CCTGGAGTGC CACCCCGAGA GAGGTTGCGT CCCAGAGCCT GGAGCCGCCG TGGCCGCCAG CAAGGGGCTG CCGCAGCAGC TGCCAGCACC TCCGGACGAG GATGACTCAG CTGCCCCATC CACGTTGTCC CTGCTGGGCC CCACTTTCCC CGGCTTAAGC AGCTGCTCCG CTGACCTTAA AGACATCCTG AGCGAGGCCA GCACCATGCA ACTCCTTCAG CAACAGCAGC AGGAAGCAGT ATCCGAAGGC AGCAGCAGCG GGAGAGCGAG GGAGGCCTCG GGGCTCCCA CTTCCTCCAA GGACAATTAC TTAGGGGGCA CTTCGACCAT TTCTGACAAC GCCAAGGAGT TGTGTAAGGC AGTGTCGGTG TCCATGGGCC TGGGTGTGGA GGCGTTGGAG CATCTGAGTC CAGGGGAACA GCTTCGGGGG GATTGCATGT ACGCCCCACT TTTGGGAGTT CCACCCGCTG TGCGTCCCAC TCCTTGTGCC CCATTGGCCG AATGCAAAGG TTCTCTGCTA GACGACAGCG CAGGCAAGAG CACTGAAGAT ACTGCTGAGT ATTCCCCTTT CAAGGGAGGT TACACCAAAG GCCTAGAAGG CGAGAGCCTA GGCTGCTCTG GCAGCGCTGC AGCAGGGAGC TCCGGGACAC TTGAACTGCC GTCTACCCTG TCTCTCTACA AGTCCGGAGC ACTGGACGAG GCAGCTGCGT ACCAGAGTCG CGACTACTAC AACTTTCCAC TGGCTCTGGC CGGACCGCCG CCCCCTCCGC CGCCTCCCCA TCCCCACGCT CGCATCAAGC TGGAGAACCC GCTGGACTAC GGCAGCGCCT GGGCGGCTGC GGCGGCGCAG TGCCGCTATG GGGACCTGGC GAGCCTGCAT GGCGCGGGTG CAGCGGGACC CGGTTCTGGG TCACCCTCAG CCGCCGCTTC CTCATCCTGG CACACTCTCT TCACAGCCGA AGAAGGCCAG TTGTATGGAC CGTGTGGTGG TGGTGGGGGT GGTGGCGGCG GCGGCGGCGG CGGCGGCGGC GCGGCGGCGG CGGCGAGGCG GGAGCTGTAG CCCCCTACGG CTACACTCGG CCCCCTCAGG GGCTGGCGGG CCAGGAAAGC GACTTCACCG CACCTGATGT GTGGTACCCT GGCGGCATGG TGAGCAGAGT GCCCTATCCC AGTCCCACTT GTGTCAAAAG CGAAATGGGC CCCTGGATGG ATAGCTACTC CGGACCTTAC GGGGACATGC GTTTGGAGAC TGCCAGGGAC CATGTTTTGC CCATTGACTA TTACTTTCCA CCCCAGAAGA CCTGCCTGAT CTGTGGAGAT GAAGCTTCTG GGTGTCACTA TGGAGCTCTC ACATGTGGAA GCTGCAAGGT CTTCTTCAAA AGAGCCGCTG AAGGGAAACA GAAGTACCTG TGCGCCAGCA GAAATGATTG CACTATTGAT AAATTCCGAA GGAAAAATTG TCCATCTTGT CGTCTTCGGA AATGTTATGA AGCAGGGATG ACTCTGGGAG CCCGGAAGCT GAAGAAACTT GGTAATCTGA AACTACAGGA GGAAGGAGAG CTTCCAGCA CCACCAGCCC CACTGAGGAG ACAACCCAGA AGCTGACAGT GTCACACATT GAAGGCTATG AATGTCAGCC CATCTTTCTG AATGTCCTGG AAGCCATTGA GCCAGGTGTA GTGTGTGCTG GACACGACAA CAACCAGCCC GACTCCTTTG CAGCCTTGCT CTCTAGCCTC AATGAACTGG GAGAGAGACA GCTTGTACAC GTGGTCAAGT GGGCCAAGGC CTTGCCTGGC TTCCGCAACT TACACGTGGA CGACCAGATG GCTGTCATTC AGTACTCCTG GATGGGCTC ATGGTGTTTG CCATGGGCTG GCGATCCTTC ACCAATGTCA ACTCCAGGAT GCTCTACTTC GCCCCTGATC TGGTTTTCAA TGAGTACCGC ATGCACAAGT CCCGGATGTA CAGCCAGTGT GTCCGAATGA GGCACCTCTC TCAAGAGTTT GGATGGCTCC AAATCACCCC CCAGGAATTC CTGTGCATGA AAGCACTGCT ACTCTTCAGC ATTATTCCAG TGGATGGGCT GAAAAATCAA AAATTCTTTG ATGAACTTCG AATGAACTAC ATCAAGGAAC TCGATCGTAT CATTGCATGC AAAAGAAAAA ATCCCACATC CTGCTCAAGA CGCTTCTACC AGCTCACCAA GCTCCTGGAC TCCGTGCAGC CTATTGCGAG AGAGCTGCAT CAGTTCACTT TTGACCTGCT AATCAAGTCA CACATGGTGA GCGTGGACTT TCCGGAAATG ATGGCAGAGA TCATCTCTGT GCAAGTGCCC AAGATCCTTT CTGGGAAAGT CAAGCCCATC TATTTCCACA CCCAGTGAAG CATTGGAAAC CCTATTTCCC CACCCCAGCT CATGCCCCCT TCAGATGTC TTCTGCCTGT TATAACTCTG CACTACTCCT CTGCAGTGCC TTGGGGAATT TCCTCTATTG ATGTACAGTC TGTCATGAAC ATGTTCCTGA ATTCTATTTG CTGGGCTTTT TTTTTCTCTT TCTCTCCTTT CTTTTCTTC TTCCCTCCCT ATCTAACCCT CCCATGGCAC CTTCAGACTT GCTTCCCAT TGTGGCTCCT ATCTGTGTTT |

TABLE OF CERTAIN SEQUENCES

| SEQ ID NO | Description | Sequence |
|---|---|---|
| | | TGAATGGTGT TGTATGCCTT TAAATCTGTG ATGATCCTCA TATGGCCCAG TGTCAAGTTG |
| | | TGCTTGTTTA CAGCACTACT CTGTGCCAGC CACACAAACG TTTACTTATC TTATGCCACG |
| | | GGAAGTTTAG AGAGCTAAGA TTATCTGGGG AAATCAAAAC AAAAACAAGC AAACAAAAAA |
| | | AAAAAGCAAA AACAAAACAA AAATAAGCC AAAAAACCTT GCTAGTGTTT TTTCCTCAAA |
| | | AATAAATAAA TAAATAAATA AATACGTACA TACATACACA CATACATACA AACATATAGA |
| | | AATCCCCAAA GAGGCCAATA GTGACGAGAA GGTGAAAATT GCAGGCCCAT GGGGAGTTAC |
| | | TGATTTTTTC ATCTCCTCCC TCCACGGGAG ACTTTATTTT CTGCCAATGG CTATTGCCAT |
| | | TAGAGGGCAG AGTGACCCCA GAGCTGAGTT GGGCAGGGGG GTGGACAGAG AGGAGAGGAC |
| | | AAGGAGGGCA ATGGAGCATC AGTACCTGCC CACAGCCTTG GTCCCTGGGG GCTAGACTGC |
| | | TCAACTGTGG AGCAATTCAT TATACTGAAA ATGTGCTTGT TGTTGAAAAT TTGTCTGCAT |
| | | GTTAATGCCT CACCCCCAAA CCCTTTTCTC TCTCACTCTC TGCCTCCAAC TTCAGATTGA |
| | | CTTTCAATAG TTTTTCTAAG ACCTTTGAAC TGAATGTTCT CTTCAGCCAA AACTTGGCGA |
| | | CTTCCACAGA AAAGTCTGAC CACTGAGAAG AAGGAGAGCA GAGATTTAAC CCTTTGTAAG |
| | | GCCCCATTTG GATCCAGGTC TGCTTTCTCA TGTGTGAGTC AGGGAGGAGC TGGAGCCAGA |
| | | GGAGAAGAAA ATGATAGCTT GGCTGTTCTC CTGCTTAGGA CACTGACTGA ATAGTTAAAC |
| | | TCTCACTGCC ACTACCTTTT CCCCACCTTT AAAAGACCTG AATGAAGTTT CTGCCAAAC |
| | | TCCGTGAAGC CACAAGCACC TTATGTCCTC CCTTCAGTGT TTTGTGGGCC TGAATTTCAT |
| | | CACACTGCAT TTCAGCCATG GTCATCAAGC CTGTTTGCTT CTTTTGGGCA TGTTCACAGA |
| | | TTCTCTGTTA AGAGCCCCCA CCACCAAGAA GGTTAGCAGG CCAACAGCTC TGACATCTAT |
| | | CTGTAGATGC CAGTAGTCAC AAAGATTTCT TACCAACTCT CAGATCGCTG GAGCCCTTAG |
| | | ACAAACTGGA AAGAAGGCAT CAAAGGGATC AGGCAAGCTG GGCGTCTTGC CCTTGTCCCC |
| | | CAGAGATGAT ACCCTCCCAG CAAGTGGAGA AGTTCTCACT TCCTTCTTTA GAGCAGCTAA |
| | | AGGGGCTACC CAGATCAGGG TTGAAGAGAA AACTCAATTA CCAGGGTGGG AAGAATGAAG |
| | | GCACTAGAAC CAGAAACCCT GCAAATGCTC TTCTTGTCAC CCAGCATATC CACCTGCAGA |
| | | AGTCATGAGA AGAGAGAAGG AACAAAGAGG AGACTCTGAC TACTGAATTA AAATCTTCAG |
| | | CGGCAAAGCC TAAAGCCAGA TGGACACCAT CTGGTGAGTT TACTCATCAT CCTCCTCTGC |
| | | TGCTGATTCT GGGCTCTGAC ATTGCCCATA CTCACTCAGA TTCCCCACCT TTGTTGCTGC |
| | | CTCTTAGTCA GAGGGAGGCC AAACCATTGA GACTTTCTAC AGAACCATGG CTTCTTTCGG |
| | | AAAGGTCTGG TTGGTGTGGC TCCAATACTT TGCCACCCAT GAACTCAGGG TGTGCCCTGG |
| | | GACACTGGTT TTATATAGTC TTTTGGCACA CCTGTGTTCT GTTGACTTCG TTCTTCAAGC |
| | | CCAAGTGCAA GGGAAAATGT CCACCTACTT TCTCATCTTG GCCTCTGCCT CCTTACTTAG |
| | | CTCTTAATCT CATCTGTTGA ACTCAAGAAA TCAAGGGCCA GTCATCAAGC TGCCCATTTT |
| | | AATTGATTCA CTCTGTTTGT TGAGAGGATA GTTTCTGAGT GACATGATAT GATCCACAAG |
| | | GGTTTCCTTC CCTGATTTCT GCATTGATAT TAATAGCCAA ACGAACTTCA AAACAGCTTT |
| | | AAATAACAAG GGAGAGGGGA ACCTAAGATG ACTAATATGC CAATCCAAGA CTGCTGGAGA |
| | | AAACTAAAGC TGACAGGTTC CCTTTTTGGG GTGGGATAGA CATGTTCTGG TTTTCTTTAT |
| | | TATTACACAA TCTGGCTCAT GTACAGGATC ACTTTTAGCT GTTTTAAACA GAAAAAAATA |
| | | TCCACCACTC TTTTCAGTTA CACTAGGTTA CATTTTAATA GGTCCTTTAC ATCTGTTTTG |
| | | GAATGATTTT CATCTTTTGT GATACACAGA TTGAATTATA TCATTTTCAT ATCTCTCCTT |
| | | GTAAATACTA GAAGCTCTCC TTTACATTTC TCTATCAAAT TTTTCATCTT TATGGGTTTC |
| | | CCAATTGTGA CTCTTGTCTT CATGAATATA TGTTTTTCAT TTGCAAAAGC CAAAAATCAG |
| | | TGAAACAGCA GTGTAATTAA AAGCAACAAC TGGATTACTC CAAATTTCCA AATGACAAAA |
| | | CTAGGGAAAA ATAGCCTACA CAAGCCTTTA GGCCTACTCT TTCTGTGCTT GGGTTTGAGT |
| | | GAACAAAGGA GATTTTAGCT TGGCTCTGTT CTCCCATGGA TGAAAGGAGG AGGATTTTTT |
| | | TTTTCTTTTG GCCATTGATG TTCTAGCCAA TGTAATTGAC AGAAGTCTCA TTTTGCATGC |
| | | GCTCTGCTCT ACAAACAGGA TTGGTATGGT TGGTATACTG TACTCACCTG TGAGGGACTG |
| | | GCCACTCAGA CCCACTTAGC TGGTGAGCTA GAAGATGAGG ATCACTCACT GGAAAAGTCA |
| | | CAAGGACCAT CTCCAAACAA GTTGGCAGTG CTCGATGTGG ACGAAGAGTG AGGAAGAGAA |
| | | AAAGAAGGAG CACCAGGGAG AAGGCTCCGT CTGTGCTGGG CAGCAGACAG CTGCCAGGAT |
| | | CACGAACTCT GTAGTCAAAG AAAAGAGTCG TGTGGCAGTT TCAGCTCTCG TTCATTGGGC |
| | | AGCTCGCCTA GGCCCAGCCT CTGAGCTGAC ATGGGAGTTG TTGGATTCTT TGTTTCATAG |
| | | CTTTTTCTAT GCCATAGGCA ATATTGTTGT TCTTGGAAAG TTTATTATTT TTTTAACTCC |
| | | CTTACTCTGA GAAAGGGATA TTTTGAAGGA CTGTCATATA TCTTTGAAAA AGAAAATCT |
| | | GTAATACATA TATTTTTATG TATGTTCACT GGCACTAAAA AATATAGAGA GCTTCATTCT |
| | | GTCCTTTGGG TAGTTGCTGA GGTAATTGTC CAGGTTGAAA AATAATGTGC TGATGCTAGA |
| | | GTCCCTCTCT GTCCATACTC TACTTCTAAA TACATATAGG CATACATAGC AAGTTTTATT |
| | | TGACTTGTAC TTTAAGAAA AATATGTCCA CCATCCACAT GATGCACAAA TGAGCTAACA |
| | | TTGAGCTTCA AGTAGCTTCT AAGTGTTTGT TTCATTAGGC ACAGCACAGA TGTGGCCTTT |
| | | CCCCCCTTCT CTCCCTTGAT ATCTCGGCAGG GCATAAAGGC CCAGGCCACT TCCTCTGCCC |
| | | CTTCCCAGCC CTGCACCAAA GCTGCATTTC AGGAGACTCT CTCCAGACAG CCCAGTAACT |
| | | ACCCGAGCAT GGCCCCTGCA TAGCCCTGGA AAAATAAGAG GCTGACTGTC TACGAATTAT |
| | | CTTGTGCCAG TTGCCCAGGT GAGAGGGCAC TGGGCCAAGG GAGTGGTTTT CATGTTTGAC |
| | | CCACTACAAG GGGTCATGGG AATCAGGAAT GCCAAAGCAC CAGATCAAAT CCAAAACTTA |
| | | AAGTCAAAAT AAGCCATTCA GCATGTTCAG TTTCTTGGAA AAGGAAGTTT CTACCCCTGA |
| | | TGCCTTTGTA GGCAGATCTG TTCTCACCAT TAATCTTTTT GAAAATCTTT TAAAGCAGTT |
| | | TTTAAAAGA GAGATGAAAG CATCACATTA TAACCAAA GATTACATTG TACCTGCTAA |
| | | GATACCAAAA TTCATAAGGG CAGGGGGGA GCAAGCATTA GTGCCTCTTT GATAAGCTGT |
| | | CCAAAGACAG ACTAAAGGAC TCTGCTGGTG ACTGACTTAT AAGAGCTTTG TGGGTTTTTT |
| | | TTTCCCTAAT AATATACATG TTTAGAAGAA TTGAAAATAA TTTCGGGAAA ATGGGATTAT |
| | | GGGTCCTTCA CTAAGTGATT TTATAAGCAG AACTGGCTTT CCTTTTCTCT AGTAGTTGCT |
| | | GAGCAAATTG TTGAAGCTCC ATCATTGCAT GGTTGGAAAT GGAGCTGTTC TTAGCCACTG |
| | | TGTTTGCTAG TGCCCATGTT AGCTTATCTG AAGATGTGAA ACCCTTGCTG ATAAGGGAGC |
| | | ATTTAAAGTA CTAGATTTTG CACTAGAGGG ACAGCAGGCA GAAATCCTTA TTTCTGCCCA |
| | | CTTTGGATGG CACAAAAAGT TATCTGCAGT TGAAGGCAGA AAGTTGAAAT ACATTGTAAA |

TABLE OF CERTAIN SEQUENCES

| SEQ ID NO | Description | Sequence |
|---|---|---|
| | | TGAATATTTG TATCCATGTT TCAAAATTGA AATATATATA TATATATATA TATATATATA<br>TATATATATA TAGTGTGTGT GTGTGTTCTG ATAGCTTTAA CTTTCTCTGC ATCTTTATAT<br>TTGGTTCCAG ATCACACCTG ATGCCATGTA CTTGTGAGAG AGGATGCAGT TTTGTTTTGG<br>AAGCTCTCTC AGAACAAACA AGACACCTGG ATTGATCAGT TAACTAAAAG TTTTCTCCCC<br>TATTGGGTTT GACCCACAGG TCCTGTGAAG GAGCAGAGGG ATAAAAAGAG TAGAGGACAT<br>GATACATTGT ACTTTACTAG TTCAAGACAG ATGAATGTGG AAAGCATAAA AACTCAATGG<br>AACTGACTGA GATTTACCAC AGGGAAGGCC CAAACTTGGG GCCAAAAGCC TACCCAAGTG<br>ATTGACCAGT GGCCCCCTAA TGGGACCTGA GCTGTTGGAA GAAGAGAACT GTTCCTTGGT<br>CTTCACCATC CTTGTGAGAG AAGGGCAGTT TCCTGCATTG GAACCTGGAG CAAGCGCTCT<br>ATCTTTCACA CAAATTCCCT CACCTGAGAT TGAGGTGCTC TTGTTACTGG GTGTCTGTGT<br>GCTGTAATTC TGGTTTTGGA TATGTTCTGT AAAGATTTTG ACAAATGAAA ATGTGTTTTT<br>CTCTGTTAAA ACTTGTCAGA GTACTAGAAG TTGTATCTCT GTAGGTGCAG GTCCATTTCT<br>GCCCACAGGT AGGGTGTTTT TCTTTGATTA AGAGATTGAC ACTTCTGTTG CCTAGGACCT<br>CCCAACTCAA CCATTTCTAG GTGAAGGCAG AAAAATCCAC ATTAGTTACT CCTCTTCAGA<br>CATTTCAGCT GAGATAACAA ATCTTTTGGA ATTTTTTCAC CCATAGAAAG AGTGGTAGAT<br>ATTTGAATTT AGCAGGTGGA GTTTCATAGT AAAAACAGCT TTTGACTCAG CTTTGATTTA<br>TCCTCATTTG ATTTGGCCAG AAAGTAGGTA ATATGCATTG ATTGGCTTCT GATTCCAATT<br>CAGTATAGCA AGGTGCTAGG TTTTTTCCTT TCCCCACCTG TCTCTTAGCC TGGGGAATTA<br>AATGAGAAGC CTTAGAATGG GTGGCCCTTG TGACCTGAAA CACTTCCCAC ATAAGCTACT<br>TAACAAGATT GTCATGGAGC TGCAGATTCC ATTGCCCACC AAAGACTAGA ACACACACAT<br>ATCCATACAC CAAAGGAAAG ACAATTCTGA AATGCTGTTT CTCTGGTGGT TCCCTCTCTG<br>GCTGCTGCCT CACAGTATGG GAACCTGTAC TCTGCAGAGG TGACAGGCCA GATTTGCATT<br>ATCTCACAAC CTTAGCCCTT GGTGCTAACT GTCCTACAGT GAAGTGCCTG GGGGGTTGTC<br>CTATCCCATA AGCCACTTGG ATGCTGACAG CAGCCACCAT CAGAATGACC CACGCAAAAA<br>AAAGAAAAAA AAAATTAAAA AGTCCCCTCA CAACCCAGTG ACACCTTTCT GCTTTCCTCT<br>AGACTGGAAC ATTGATTAGG GAGTGCCTCA GACATGACAT TCTTGTGCTG TCCTTGGAAT<br>TAATCTGGCA GCAGGAGGGA GCAGACTATG TAAACAGAGA TAAAAATTAA TTTTCAATAT<br>TGAAGGAAAA AAGAAATAAG AAGAGAGAGA GAAAGAAAGC ATCACACAAA GATTTTCTTA<br>AAAGAAACAA TTTTGCTTGA AATCTCTTTA GATGGGGCTC ATTTCTCACG GTGGCACTTG<br>GCCTCCACTG GGCAGCAGGA CCAGCTCCAA GCGCTAGTGT TCTGTTCTCT TTTTGTAATC<br>TTGGAATCTT TTGTTGCTCT AAATACAATT AAAAATGGCA GAAACTTGTT TGTTGGACTA<br>CATGTGTGAC TTTGGGTCTG TCTCTGCCTC TGCTTTCAGA AATGTCATCC ATTGTGTAAA<br>ATATTGGCTT ACTGGTCTGC CAGCTAAAAC TTGGCCACAT CCCCTGTTAT GGCTGCAGGA<br>TCGAGTTATT GTTAACAAAG AGACCCAAGA AAAGCTGCTA ATGTCCTCTT ATCATTGTTG<br>TTAATTTGTT AAAACATAAA GAAATCTAAA ATTTCAAAAAA |
| 57 | Human androgen receptor (AR) mRNA, transcript variant 2 (GenBank NM_001011645.2) | GCTGCGAGCA GAGAGGGATT CCTCGGAGGT CATCTGTTCC ATCTTCTTGC CTATGCAAAT<br>GCCTGCCTGA AGCTGCTGGA GGCTGGCTTT GTACCGGACT TTGTACAGGG AACCAGGGAA<br>ACGAATGCAG AGTGCTCCTG ACATTGCCTG TCACTTTTTC CCATGATACT CTGGCTTCAC<br>AGTTTGGAGA CTGCCAGGGA CCATGTTTTG CCCATTGACT ATTACTTTCC ACCCCAGAAG<br>ACCTGCCTGA TCTGTGGAGA TGAAGCTTCC GGGTGTCACT ATGGAGCTCT CACATGTGGA<br>AGCTGCAAGG TCTTCTTCAA AAGAGCCGCT GAAGGGAAAC AGAAGTACCT GTGCGCCAGC<br>AGAAATGATT GCACTATTGA TAAATTCCGA AGGAAAAATT GTCCATCTTG TCGTCTTCGG<br>AAATGTTATG AAGCAGGGAT GACTCTGGGA GCCCGGAAGC TGAAGAAACT TGGTAATCTG<br>AAACTACAGG AGGAAGGAGA GGCTTCCAGC ACCACCAGCC CCACTGAGGA GACAACCCAG<br>AAGCTGACAG TGTCACACAT TGAAGGCTAT GAATGTCAGC CCATCTTTCT GAATGTCCTG<br>GAAGCCATTG AGCCAGGTGT AGTGTGTGCT GGACACGACA ACAACCAGCC CGACTCCTTT<br>GCAGCCTTGC TCTCTAGCCT CAATGAACTG GGAGAGAGAC AGCTTGTACA CGTGGTCAAG<br>TGGGCCAAGG CCTTGCCTGG CTTCCGCAAC TTACACGTGG ACGACCAGAT GGCTGTCATT<br>CAGTACTCCT GGATGGGGCT CATGGTGTTT GCCATGGGCT GGCGATCCTT CACCAATGTC<br>AACTCCAGGA TGCTCTACTT CGCCCCTGAT CTGGTTTTCA ATGAGTACCG CATGCACAAG<br>TCCCGGATGT ACAGCCAGTG TGTCCGAATG AGGCACCTCT CTCAAGAGTT TGGATGGCTC<br>CAAATCACCC CCCAGGAATT CCTGTGCATG AAAGCACTGC TACTCTTCAG CATTATTCCA<br>GTGGATGGGC TGAAAAATCA AAAATTCTTT GATGAACTTC GAATGAACTA CATCAAGGAA<br>CTCGATCGTA TCATTGCATG CAAAAGAAAA AATCCCACAT CCTGCTCAAG ACGCTTCTAC<br>CAGCTCACCA AGCTCCTGGA CTCCGTGCAG CCTATTGCGA GAGAGCTGCA TCAGTTCACT<br>TTTGACCTGC TAATCAAGTC ACACATGGTG AGCGTGGACT TTCCGGAAAT GATGGCAGAG<br>ATCATCTCTG TGCAAGTGCC CAAGATCCTT TCTGGGAAAG TCAAGCCCAT CTATTTCCAC<br>ACCCAGTGAA GCATTGGAAA CCCTATTTCC CCACCCCAGC TCATGCCCCC TTTCAGATGT<br>CTTCTGCCTG TTATAACTCT GCACTACTCC TCTGCAGTGC CTTGGGGAAT TTCCTCTATT<br>GATGTACAGT CTGTCATGAA CATGTTCCTG AATTCTATTT GCTGGGCTTT TTTTTTCTCT<br>TTCTCTCCTT TCTTTTTCTT CTTCCCTCCC TATCTAACCC TCCCATGGCA CCTTCAGACT<br>TTGCTTCCCA TTGTGGCTCC TATCTGTGTT TTGAATGGTG TTGTATGCCT TTAAATCTGT<br>GATGATCCTC ATATGGCCCA GTGTCAAGTT GTGCTTGTTT ACAGCACTAC TCTGTGCCAG<br>CCACACAAAC GTTTACTTAT CTTATGCCAC GGGAAGTTTA GAGAGCTAAG ATTATCTGGG<br>GAAATCAAAA CAAAAACAAG CAAACAAAAA AAAAAGCAA AACAAAACA AAAAATAAGC<br>CAAAAAACCT TGCTAGTGTT TTTTCCTCAA AATAAATAA ATAAATAAAT AAATACGTAC<br>ATACATACAC ACATACATAC AAACATATAG AAATCCCAA GAGGCCAAT AGTGACAGA<br>AGGTGAAAAT TGCAGGCCCA TGGGGAGTTA CTGATTTTTT CATCTCCTCC CTCCACGGGA<br>GACTTTATTT TCTGCCAATG GCTATTGCCA TTAGAGGGCA GAGTGACCCC AGAGCTGAGT<br>TGGGCAGGGG GGTGGACAGA GAGGAGAGGA CAAGGAGGGC AATGGAGCAT CAGTACCTGC<br>CCACAGCCTT GGTCCCTGGG GGCTAGACTG CTCAACTGTG GAGCAATTCA TTATACTGAA<br>AATGTGCTTG TTGTTGAAAA TTTGTCTGCA TGTTAATGCC TCACCCCCAA ACCCTTTTCT<br>CTCTCACTCT CTGCCTCCAA CTTCAGATTG ACTTTCAATA GTTTTTCTAA GACCTTTGAA |

TABLE OF CERTAIN SEQUENCES

| SEQ ID NO | Description | Sequence |
|---|---|---|
| | | CTGAATGTTC TCTTCAGCCA AAACTTGGCG ACTTCCACAG AAAAGTCTGA CCACTGAGAA |
| | | GAAGGAGAGC AGAGATTTAA CCCTTTGTAA GGCCCCATTT GGATCCAGGT CTGCTTTCTC |
| | | ATGTGTGAGT CAGGGAGGAG CTGGAGCCAG AGGAGAAGAA AATGATAGCT TGGCTGTTCT |
| | | CCTGCTTAGG ACACTGACTG AATAGTTAAA CTCTCACTGC CACTACCTTT TCCCCACCTT |
| | | TAAAAGACCT GAATGAAGTT TTCTGCCAAA CTCCGTGAAG CCACAAGCAC CTTATGTCCT |
| | | CCCTTCAGTG TTTTGTGGGC CTGAATTTCA TCACACTGCA TTTCAGCCAT GGTCATCAAG |
| | | CCTGTTTGCT TCTTTTGGGC ATGTTCACAG ATTCTCTGTT AAGAGCCCCC ACCACCAAGA |
| | | AGGTTAGCAG GCCAACAGCT CTGACATCTA TCTGTAGATG CCAGTAGTCA CAAAGATTTC |
| | | TTACCAACTC TCAGATCGCT GGAGCCCTTA GACAAACTGG AAAGAAGGCA TCAAAGGGAT |
| | | CAGGCAAGCT GGGCGTCTTG CCCTTGTCCC CCAGAGATGA TACCCTCCCA GCAAGTGGAG |
| | | AAGTTCTCAC TTCCTTCTTT AGAGCAGCTA AAGGGGCTAC CCAGATCAGG GTTGAAGAGA |
| | | AAACTCAATT ACCAGGGTGG GAAGAATGAA GGCACTAGAA CCAGAAACCC TGCAAATGCT |
| | | CTTCTTGTCA CCCAGCATAT CCACCTGCAG AAGTCATGAG AAGAGAGAAG GAACAAAGAG |
| | | GAGACTCTGA CTACTGAATT AAAATCTTCA GCGGCAAAGC CTAAAGCCAG ATGGACACCA |
| | | TCTGGTGAGT TTACTCATCA TCCTCCTCTG CTGCTGATTC TGGGCTCTGA CATTGCCCAT |
| | | ACTCACTCAG ATTCCCCACC TTTGTTGCTG CCTCTTAGTC AGAGGGAGGC CAAACCATTG |
| | | AGACTTTCTA CAGAACCATG GCTTCTTTCG GTTGGTGTGG CTCCAATACT |
| | | TTGCCACCCA TGAACTCAGG GTGTGCCCTG GGACACTGGT TTTATATAGT CTTTTGGCAC |
| | | ACCTGTGTTC TGTTGACTTC GTTCTTCAAG CCCAAGTGCA AGGGAAAATG TCCACCTACT |
| | | TTCTCATCTT GGCCTCTGCC TCCTTACTTA GCTCTTAATC TCATCTGTTG AACTCAAGAA |
| | | ATCAAGGGCC AGTCATCAAG CTGCCCATTT TAATTGATTC ACTCTGTTTG TTGAGAGGAT |
| | | AGTTTCTGAG TGACATGATA TGATCCACAA GGGTTTCCTT CCCTGATTTC TGCATTGATA |
| | | TTAATAGCCA AACGAACTTC AAAACAGCTT TAAATAACAA GGGAGAGGGG AACCTAAGAT |
| | | GAGTAATATG CCAATCCAAG ACTGCTGGAG AAAACTAAAG CTGACAGGTT CCCTTTTTGG |
| | | GGTGGGATAG ACATGTTCTG GTTTTCTTTA TTATTACACA ATCTGGCTCA TGTACAGGAT |
| | | CACTTTTAGC TGTTTTAAAC AGAAAAAAAT ATCCACCACT CTTTTCAGTT ACACTAGGTT |
| | | ACATTTTAAT AGGTCCTTTA CATCTGTTTT GGAATGATTT TCATCTTTTG TGATACACAG |
| | | ATTGAATTAT ATCATTTTCA TATCTCTCCT TGTAAATACT AGAAGCTCTC CTTTACATTT |
| | | CTCTATCAAA TTTTTCATCT TTATGGGTTT CCCAATTGTG ACTCTTGTCT TCATGAATAT |
| | | ATGTTTTTCA TTTGCAAAAG CCAAAAATCA GTGAAACAGC AGTGTAATTA AAAGCAACAA |
| | | CTGGATTACT CCAAATTTCC AAATGACAAA ACTAGGGAAA AATAGCCTAC ACAAGCCTTT |
| | | AGGCCTACTC TTTCTGTGCT TGGGTTTGAG TGAACAAAGG AGATTTTAGC TTGGCTCTGT |
| | | TCTCCCATGG ATGAAAGGAG GAGGATTTTT TTTTTCTTTT GGCCATTGAT GTTCTAGCCA |
| | | ATGTAATTGA CAGAAGTCTC ATTTTGCATG CGCTCTGCTC TACAAACAGA GTTGGTATGG |
| | | TTGGTATACT GTACTCACCT GTGAGGGACT GGCCACTCAG ACCCACTTAG CTGGTGAGCT |
| | | AGAAGATGAG GATCACTCAC TGGAAAAGTC ACAAGGACCA TCTCCAAACA AGTTGGCAGT |
| | | GCTCGATGTG GACGAAGAGT GAGGAAGAGA AAAAGAAGGA GCACCAGGGA GAAGGCTCCG |
| | | TCTGTGCTGG GCAGCAGACA GCTGCCAGGA TCACGAACTC TGTAGTCAAA GAAAAGAGTC |
| | | GTGTGGCAGT TTCAGCTCTC GTTCATTGGG CAGCTCGCCT AGGCCCAGCC TCTGAGCTGA |
| | | CATGGGAGTT GTTGGATTCT TTGTTTCATA GCTTTTTCTA TGCCATAGGC AATATTGTTG |
| | | TTCTTGGAAA GTTTATTATT TTTTTAACTC CCTTACTCTG AGAAAGGGAT ATTTTGAAGG |
| | | ACTGTCATAT ATCTTTGAAA AAAGAAAATC TGTAATACAT ATATTTTTAT GTATGTTCAC |
| | | TGGCACTAAA AAATATAGAG AGCTTCATTC TGTCCTTTGG GTAGTTGCTG AGGTAATTGT |
| | | CCAGGTTGAA AAATAATGTG CTGATGCTAG AGTCCCTCTC TGTCCATACT CTACTTCTAA |
| | | ATACATATAG GCATACATAG CAAGTTTTAT TTGACTTGTA CTTTAAGAGA AAATATGTCC |
| | | ACCATCCACA TGATGCACAA ATGAGCTAAC ATTGAGCTTC AAGTAGCTTC TAAGTGTTTG |
| | | TTTCATTAGG CACAGCACAG ATGTGGCCTT TCCCCCCTTC TCTCCCTTGA TATCTGGCAG |
| | | GGCATAAAGG CCCAGGCCAC TTCCTCTGCC CCTTCCCAGC CCTGCACCAA AGCTGCATTT |
| | | CAGGAGACTC TCTCCAGACA GCCCAGTAAC TACCCGAGCA TGGCCCCTGC ATAGCCCTGG |
| | | AAAAATAAGA GGCTGACTGT CTACGAATTA TCTTGTGCCA GTTGCCCAGG TGAGAGGGCA |
| | | CTGGGCCAAG GGAGTGGTTT TCATGTTTGA CCCACTACAA GGGGTCATGG GAATCAGGAA |
| | | TGCCAAAGCA CCAGATCAAA TCCAAAACTT AAAGTCAAAA TAAGCCATTC AGCATGTTCA |
| | | GTTTCTTGGA AAAGGAAGTT TCTACCCCTG ATGCCTTTGT AGGCAGATCT GTTCTCACCA |
| | | TTAATCTTTT TGAAAATCTT TTAAAGCAGT TTTTAAAAAG AGAGATGAAA GCATCACATT |
| | | ATATAACCAA AGATTACATT GTACCTGCTA AGATACCAAA ATTCATAAGG GCAGGGGGGG |
| | | AGCAAGCATT AGTGCCTCTT TGATAAGCTG TCCAAAGACA GACTAAAGGA CTCTGCTGGT |
| | | GACTGACTTA TAAGAGCTTT GTGGGTTTTT TTTTCCCTAA TAATATACAT GTTTAGAAGA |
| | | ATTGAAAATA ATTTCGGGAA AATGGGATTA TGGGTCCTTC ACTAAGTGAT TTTATAAGCA |
| | | GAACTGGCTT TCCTTTTCTC TAGTAGTTGC TGAGCAAATT GTTGAAGCTC CATCATTGCA |
| | | TGGTTGGAAA TGGAGCTGTT CTTAGCCACT GTGTTTGCTA GTGCCCATGT TAGCTTATCT |
| | | GAAGATGTGA AACCCTTGCT GATAAGGGAG CATTTAAAGT ACTAGATTTT GCACTAGAGG |
| | | GACAGCAGGC AGAAATCCTT ATTTCTGCCC ACTTTGGATG GCACAAAAAG TTATCTGCAG |
| | | TTGAAGGCAG AAAGTTGAAA TACATTGTAA ATGAATATTT GTATCCATGT TTCAAAATTG |
| | | AAATATATAT ATATATATAT ATATATATAT ATATATATAT ATAGTGTGTG TGTGTGTTCT |
| | | GATAGCTTTA ACTTTCTCTG CATCTTTATA TTTGGTTCCA GATCACACCT GATGCCATGT |
| | | ACTTGTGAGA GAGGATGCAG TTTTGTTTTG GAAGCTCTCT CAGAACAAAC AAGACACCTG |
| | | GATTGATCAG TTAACTAAAA GTTTTCTCCC CTATTGGGTT TGACCCACAG GTCCTGTGAA |
| | | GGAGCAGAGG GATAAAAAGA GTAGAGGACA TGATACATTG TACTTTACTA GTTCAAGACA |
| | | GATGAATGTG GAAAGCATAA AAACTCAATG GAACTGACTG AGATTTACCA CAGGGAAGGC |
| | | CCAAACTTGG GGCCAAAAGC CTACCCAAGT GATTGACCAG TGGCCCCCTA ATGGGACCTG |
| | | AGCTGTTGGA AGAAGAGAAC TGTTCCTTGG TCTTCACCAT CCTTGTGAGA GAAGGGCAGT |
| | | TTCCTGCATT GGAACCTGGA GCAAGCGCTC TATCTTTCAC ACAAATTCCC TCACCTGAGA |
| | | TTGAGGTGCT CTTGTTACTG GGTGTCTGTG TGCTGTAATT CTGGTTTTGG ATATGTTCTG |
| | | TAAAGATTTT GACAAATGAA AATGTGTTTT TCTCTGTTAA AACTTGTCAG AGTACTAGAA |

TABLE OF CERTAIN SEQUENCES

| SEQ ID NO | Description | Sequence |
|---|---|---|
| | | GTTGTATCTC TGTAGGTGCA GGTCCATTTC TGCCCACAGG TAGGGTGTTT TTCTTTGATT AAGAGATTGA CACTTCTGTT GCCTAGGACC TCCCAACTCA ACCATTTCTA GGTGAAGGCA GAAAAATCCA CATTAGTTAC TCCTCTTCAG ACATTTCAGC TGAGATAACA AATCTTTTGG AATTTTTTCA CCCATAGAAA GAGTGGTAGA TATTTGAATT TAGCAGGTGG AGTTTCATAG TAAAAACAGC TTTTGACTCA GCTTTGATTT ATCCTCATTT GATTTGGCCA GAAAGTAGGT AATATGCATT GATTGGCTTC TGATTCCAAT TCAGTATAGC AAGGTGCTAG GTTTTTTCCT TTCCCCACCT GTCTCTTAGC CTGGGGAATT AAATGAGAAG CCTTAGAATG GGTGGCCCTT GTGACCTGAA ACACTTCCCA CATAAGCTAC TTAACAAGAT TGTCATGGAG CTGCAGATTC CATTGCCCAC CAAAGACTAG AACACACACA TATCCATACA CCAAAGGAAA GACAATTCTG AAATGCTGTT TCTCTGGTGG TTCCCTCTCT GGCTGCTGCC TCACAGTATG GGAACCTGTA CTCTGCAGAG GTGACAGGCC AGATTTGCAT TATCTCACAA CCTTAGCCCT TGGTGCTAAC TGTCCTACAG TGAAGTGCCT GGGGGGTTGT CCTATCCCAT AAGCCACTTG GATGCTGACA GCAGCCACCA TCAGAATGAC CCACGCAAAA AAAAGAAAAA AAAAATTAAA AAGTCCCCTC ACAACCCAGT GACACCTTTC TGCTTTCCTC TAGACTGGAA CATTGATTAG GGAGTGCCTC AGACATGACA TTCTTGTGCT GTCCTTGGAA TTAATCTGGC AGCAGGAGG AGCAGACTAT GTAAACAGAG ATAAAAATTA ATTTTCAATA TTGAAGGAAA AAAGAAATAA GAAGAGAGAG AGAAAGAAAG CATCACACAA AGATTTTCTT AAAAGAAACA ATTTTGCTTG AAATCTCTTT AGATGGGGCT CATTTCTCAC GGTGGCACTT GGCCTCCACT GGGCAGCAGG ACCAGCTCCA AGCGCTAGTG TTCTGTTCTC TTTTTGTAAT CTTGGAATCT TTTGTTGCTC TAAATACAAT TAAAATGGC AGAAACTTGT TGTTGGACT ACATGTGTGA CTTTGGGTCT GTCTCTGCCT CTGCTTTCAG AAATGTCATC CATTGTGTAA AATATTGGCT TACTGGTCTG CCAGCTAAAA CTTGGCCACA TCCCCTGTTA TGGCTGCAGG ATCGAGTTAT TGTTAACAAA GAGACCCAAG AAAAGCTGCT AATGTCCTCT TATCATTGTT GTTAATTTGT TAAAACATAA AGAAATCTAA AATTTCAAAA AA |
| 50 | Human uroplakin 1B (UPK1B) mRNA | ACCTGGGTCG GGTGCAGACT GCGGAGCGGG CCCTACCGTG TGCGCAGAAA GAGGAGGCGC TTGCCTTCAG CTTGTGGGAA ATCCCGAAGA TGGCCAAAGA CAACTCAACT GTTCGTTGCT TCCAGGGCCT GCTGATTTTT GGAAATGTGA TTATTGGTTG TTGCGGCATT GCCCTGACTG CGGAGTGCAT CTTCTTTGTA TCTGACCAAC ACAGCCTCTA CCCACTGCTT GAAGCCACCG ACAACGATGA CATCTATGGG GCTGCCTGGA TCGGCATATT TGTGGGCATC TGCCTCTTCT GCCTGTCTGT TCTAGGCATT GTAGGCATCA TGAAGTCCAG CAGGAAAATT CTTCTGGCGT ATTTCATTCT GATGTTTATA GTATATGCCT TTGAAGTGGC ATCTTGTATC ACAGCAGCAA CACAACAAGA CTTTTTCACA CCCAACCTCT TCCTGAAGCA GATGCTAGAG AGGTACCAAA ACAACAGCCC TCCAAACAAT GATGACCAGT GGAAAAACAA TGGAGTCACC AAAAACCTGGG ACAGGCTCAT GCTCCAGGAC AATTGCTGTG GCGTAAATGG TCCATCAGAC TGGCAAAAAT ACACATCTGC CTTCCGGACT GAGAATAATG ATGCTGACTA TCCCTGGCCT CGTCAATGCT GTGTTATGAA CAATCTTAAA GAACCTCTCA ACCTGGAGGC TTGTAAACTA GGCGTGCCTG GTTTTTATCA CAATCAGGGC TGCTATGAAC TGATCTCTGG TCCAATGAAC CGACACGCCT GGGGGGTTGC CTGGTTTGGA TTTGCCATTC TCTGCTGGAC TTTTTGGGTT CTCCTGGGTA CCATGTTCTA CTGGAGCAGA ATTGAATATT AAGCATAAAG TGTTGCCACC ATACCTCCTT CCCCGAGTGA CTCTGGATTT GGTGCTGGAA CCAGCTCTCT CCTAATATTC CACGTTTGTG CCCCACACTA ACGTGTGTGT CTTACATTGC CAAGTCAGAT GGTACGGACT TCCTTTAGGA TCTCAGGCTT CTGCAGTTCT CATGACTCCT ATCTTTCATC CTAGTCTAGC ATTCTGCAAC ATTTATATAG ACTGTTGAAA GGAGAATTTG AAAAATGCAT AATAACTACT TCCATCCCTG CTTATTTTTA ATTTGGGAAA ATAAATACAT TCGAAGGAAC CTGTGTTATC ACAGTAACCC AGAGCTGTAT TTGGCTAGCA ATCTGCCTGT ATCTCTCACT ATTATCTAAA AGAAACCTTC CAATGCTTCT GTTGATCTCA GTATTGTCAG GGGAACAGAG AAGTTGGGAA AAGATTACTG AAATATACCT TTTGCATTTC TTTCTAGAGT AGCTCCCATA TATGGAGATG GGTGATTCTC TTGATGCCAC CTTCAGATCC TTTTATTCTC CAGAATAATT CTTAACAGTG GTTCAAATTT CCTTTCATAC CTTGAAGTAT GTGTTTAGTA GCCTCAATTC TCCATTAATT AAAAGTGTGG GCTGGGCGTG GGGGCTCATG CCTGTAATCC CAGCACTTTG GGAGGCCGAG GTGGGCAGAT CACCTGAGGT CAGGAGTTCA AGACCAGCCT GGCCAACATG GTGAAACCCC GTCTCTACAA AAATACAAAA ATTAGCCAGG CGTGATGGCA GGTGCCTGTA ATCCTAGCTA CTTGGCAGGC TAACGCAGGA GAATCACTTG ACCGGGAGAC AGAGGTTGCA GTGAGCTGAG ATCGTACCTA TTGCACTCCA TCCTGGATGA AAGAGCCAGA CTCTGTCTCA AACAAACAA AAAAGCGTGG GGACTTCTGG GGACAGACAA GGTGCCTGTT ATATATTTAC TCAGTCTTTG CCCTGAATGG TCTCAGCTTG AGACCATTTC AAACTGGAGA GAAGCAAGCC AGCCAATAGA ATGGGGTGAT TTACAGGGAT TTCTGTTTAC TGTCAAAATA TTTCTCATCT GCACTATGTT TCCATTTGTG GTCCTGAAGG AAATTCTTAT AACTCAACAT TTGTCTGGTC TTATAAGTAA AGACAGCTTT AAAATCTGTT CACTTTCAAA |

What is claimed is:

1. A method for detecting the presence of uroplakin 1B (UPK1B) and at least one marker selected from androgen receptor (AR), corticotrophin releasing hormone (CRH), insulin-like growth factor 2 (IGF2), keratin 20 (KRT20) and annexin 10 (ANXA10) in a urine sample from a human subject comprising (a) obtaining the urine sample from the human subject; (b) isolating nucleic acid from the sample; and (c) detecting UPK1B and at least one additional marker selected from AR, CRH, IGF2, KRT20, and ANXA10 by performing a polymerase chain reaction (PCR) comprising contacting the nucleic acid from the sample with a set of two to six bladder cancer marker primer pairs.

2. The method of claim 1, wherein the set of bladder cancer markers comprises:
   a) UPK1B, AR, CRH, IGF2, KRT20, and ANXA10;
   b) UPK1B AR, CRH, IGF2, and KRT20;
   c) UPK1B, CRH, IGF2, and ANXA10; or
   d) UPK1B, CRH, IGF2, and KRT20.

3. The method of claim 1, further comprising detecting an endogenous control and measuring the level of UPK1B and the at least one additional marker in the sample relative to the endogenous control range or value.

4. The method of claim 3, wherein the endogenous control is selected from ABL, GUSB, GAPDH, TUBB, and UPK1a.

5. The method of claim 1, further comprising detecting an exogenous control and measuring the level of UPK1B and the at least one additional marker in the sample relative to the exogenous control range or value.

6. The method of claim 5, wherein the exogenous control is an RNA.

7. The method of claim 1, wherein detecting the presence of uroplakin 1B (UPK1B) and the at least one additional marker comprises RT-PCR.

8. The method of claim 7, wherein the method further comprises detecting an endogenous control and comparing a Ct value or a ΔCt value for each of UPK1B and at least one additional marker to a threshold Ct value or ΔCt value, wherein ΔCt is the Ct value for the endogenous control minus the Ct value for the markers from the sample.

9. The method of claim 7, wherein the RT-PCR reaction takes less than 2 hours from an initial denaturation step through a final extension step.

10. The method of claim 1, wherein the method further comprises hybridizing an oligonucleotide probe for detecting UPK1B comprising at least 8 contiguous nucleotides of SEQ ID NO: 53 to nucleic acids amplified from the PCR reaction.

11. The method of claim 1, wherein each bladder cancer marker primer pair produces an amplicon that is 50 to 500 nucleotides long.

12. The method of claim 1, wherein at least one bladder cancer marker primer pair spans an intron in the genomic sequence of a marker detected by the primer pair.

13. The method of claim 1, wherein the primer pair for detecting uroplakin 1B (UPK1B) comprises a first primer comprising at least 8 nucleotides of SEQ ID NO: 51 and a second primer comprising at least 8 nucleotides of SEQ ID NO: 52.

14. The method of claim 1, wherein the method further comprises forming a set of two to six bladder cancer marker amplicons, wherein the set of bladder cancer marker amplicons comprises a UPK1B amplicon, and contacting the bladder cancer marker amplicons with a set of bladder cancer marker probes, wherein the set of bladder cancer marker probes comprises a probe for UPK1B comprising at least 8 contiguous nucleotides of SEQ ID NO: 53.

15. The method of claim 14, wherein the set of bladder cancer marker amplicons comprises an amplicon selected from an AR amplicon, a CRH amplicon, a IGF2amplicon, a KRT20 amplicon, and a ANXA10 amplicon, and wherein the set of bladder cancer marker probes comprises a probe for detecting one or more of the AR, CRH, IGF2, KRT20, and ANXA10 amplicons.

16. The method of claim 15, wherein the set of bladder cancer marker amplicons comprises an AR amplicon, and the set of bladder cancer marker probes comprises a probe for detecting AR comprising the sequence of SEQ ID NO: 56.

17. The method of claim 14, wherein the probe for detecting uroplakin 1B (UPK1B) comprises at least 8 contiguous nucleotides of SEQ ID NO: 53, wherein the probe is less than 30 nucleotides long.

18. The method of claim 14, wherein each bladder cancer marker probe comprises a dye, and wherein each dye is detectably different from the dyes of up to three other probes.

19. The method of claim 18, wherein each probe comprises a quencher molecule.

20. The method of claim 14, wherein the probe for UPK1B comprises the sequence of SEQ ID NO: 53.

21. The method of claim 14, wherein at least one probe comprises a fluorescent dye.

22. The method of claim 1, wherein the set of bladder cancer markers are detected in a single multiplex reaction.

23. The method of claim 1, wherein the urine sample comprises urothelial cells.

24. The method of claim 1, wherein the subject has at least one symptom of bladder cancer.

25. The method of claim 24, wherein the at least one symptom is selected from abdominal pain, blood in the urine, painful urination, frequent urination, urinary urgency, and incontinence.

26. The method of claim 1, wherein the subject has a history of bladder cancer.

27. The method of claim 26, wherein the subject is being monitored for recurrence of bladder cancer.

28. The method of claim 26, wherein the subject has been treated with Bacillus Calmette-Guerin (BCG) in the past three months.

29. The method of claim 1, wherein the subject has low grade bladder cancer.

* * * * *

SEQUENCE LISTING

<160> NUMBER OF SEQ ID NOS: 57

<210> SEQ ID NO 1
<211> LENGTH: 1434
<212> TYPE: DNA
<213> ORGANISM: Homo sapiens

<400> SEQUENCE: 1

```
tcgttccttg gcagggccct atgatttatg caggagcaga ggcagcacgc aatcgagctg      60
tcaagagagc gtcagcttat taggcaaatg ctgcgtggtt tttgaagagg gtcgacacta     120
taaaatccca ctccaggctc tggagtggag aaactcagag accaagtcca ttgagagact     180
gaggggaaag agaggagaga aagaaaaaga gagtgggaac agtaaagaga aggaagaca      240
acctccagag aaagccccg gagacgtctc tctgcagaga ggcggcagca cccggctcac      300
ctgcgaagcg cctgggaagc gagtgcccct aacatgcggc tgccgctgct tgtgtccgcg      360
ggagtcctgc tggtggctct cctgccctgc ccgccatgca gggcgctcct gagccgcggg      420
ccggtcccgg gagctcggca ggcgccgcag caccctcagc ccttggattt cttccagccg      480
ccgccgcagt ccgagcagcc ccagcagccg caggctcggc cggtcctgct ccgcatggga      540
gaggagtact tcctccgcct ggggaacctc aacaagagcc cggccgctcc cctttcgccc      600
gcctcctcgc tcctcgccgg aggcagcggc agccgcccct cgccggaaca ggcgaccgcc      660
aactttttcc gcgtgttgct gcagcagctg ctgctgcctc ggcgctcgct cgacagcccc      720
gcggctctcg cggagcgcgg cgctaggaat gccctcggcg gccaccagga ggcaccggag      780
agagaaaggc ggtccgagga gcctcccatc tccctggatc tcaccttcca cctcctccgg      840
gaagtcttgg aaatggccag ggccgagcag ttagcacagc aagctcacag caacaggaaa      900
ctcatggaga ttattgggaa ataaaacggt gcgtttggcc aaaagaatc tgcatttagc       960
acaaaaaaaa tttaaaaaaa tacagtattc tgtaccatag cgctgctctt atgccatttg     1020
tttattttta tatagcttga aacatagagg gagagaggga gagagcctat accccttact     1080
tagcatgcac aaagtgtatt cacgtgcagc agcaacacaa tgttattcgt tttgtctacg     1140
tttagtttcc gtttccaggt gtttatagtg gtgttttaaa gagaatgtag acctgtgaga     1200
aaacgttttg tttgaaaaag cagacagaag tcactcaatt gttttttgttg tggtctgagc    1260
caaagagaat gccattctct tgggtgggta agactaaatc tgtaagctct ttgaaacaac     1320
tttctcttgt aaacgtttca gtaataaaac atctttccag tccttggtca gtttggttgt    1380
gtaagagaat gttgaatact tatattttta ataaaagttg caaaggtaat catg           1434
```

<210> SEQ ID NO 2
<211> LENGTH: 5156
<212> TYPE: DNA
<213> ORGANISM: Homo sapiens

<400> SEQUENCE: 2

```
ccgctaatgt accatgccct ggtgctggaa agtgcctgag ccagctgccc cagcggcctc      60
agcactacca agttggcaca aagctcccca aattcggagg ggctcaggga aacgagtgga     120
ggggatgagg aggtgagggg taaacccatc atttcagttg gcatttgagc aggtgccatg     180
ctcagcggag atgaggctct cccatctgta ggggccgtat aacatgcac actctaaaag      240
tgcccttcgt ttctccagcc tcagctttgt ccctctcctc ctccacgtca acctggccag     300
agggtctgga cgccacagcc agggcacccc ctgctttggt ggtgactgct aatattggcc     360
aggccggcgg atcatcgtcc aggcagtttc ggcagagagc cttgggcacc agtgactccc     420
cggtcctctt tatccactgt ccaggagctg cggggactgc gcagggacta gagtacaggg     480
gccgaagagt caccaccgag cttgtgtggg aggaggtgga ttccagcccc cagccccagg    540
gctctgaatc gctgccagct cagccccctg cccagcctgc ccacagcct gagccccagc      600
aggccagaga gcccagtcct gaggtgagct gctgtggcct gtggcccagg cgaccccagc    660
```

```
gctcccagaa ctgaggctgg cagccagccc cagcctcagc cccaactgcg aggcagagag      720
acaccaatgg gaatcccaat ggggaagtcg atgctggtgc ttctcacctt cttggccttc      780
gcctcgtgct gcattgctgc ttaccgcccc agtgagaccc tgtgcggcgg ggagctggtg      840
gacaccctcc agttcgtctg tggggaccgc ggcttctact tcagcaggcc cgcaagccgt      900
gtgagccgtc gcagccgtgg catcgttgag gagtgctgtt ccgcagctg tgacctggcc       960 ctcctggaga cgtactgtgc tacccccgcc aagtccgaga gggacgtgtc gacccctccg     1020
accgtgcttc cggacaactt ccccagatac cccgtgggca agttcttcca atatgacacc     1080
tggaagcagt ccacccagcg cctgcgcagg ggcctgcctg ccctcctgcg tgcccgccgg     1140
ggtcacgtgc tcgccaagga gctcgaggcg ttcagggagg ccaaacgtca ccgtcccctg     1200
attgctctac ccacccaaga ccccgcccac ggggggcgccc cccagagat ggccagcaat     1260 cggaagtgag caaaactgcc gcaagtctgc agcccggcgc caccatcctg cagcctcctc     1320
ctgaccacgg acgtttccat caggttccat cccgaaaatc tctcggttcc acgtcccct      1380 ggggcttctc ctgacccagt ccccgtgccc cgcctccccg aaacaggcta ctctcctcgg     1440 cccccctccat cgggctgagg aagcacagca gcatcttcaa acatgtacaa aatcgattgg    1500
ctttaaacac ccttcacata ccctcccccc aaattatccc caattatccc cacacataaa     1560
aaatcaaaac attaaactaa cccccttccc cccccccac aacaaccctc ttaaaactaa     1620
ttggcttttt agaaacaccc cacaaaagct cagaaattgg ctttaaaaaa aacaaccacc     1680
aaaaaaaatc aattggctaa aaaaaaaaag tattaaaaac gaattggctg agaaacaatt     1740
ggcaaaataa aggaatttgg cactccccac ccccctcttt ctcttctccc ttggactttg     1800
agtcaaattg gcctggactt gagtccctga accagcaaag agaaaagaag dacccccagaa    1860 atcacaggtg ggcacgtcgc tgctaccgcc atctcccttc tcacgggaat tttcagggta     1920
aactggccat ccgaaaatag caacaaccca gactggctcc tcactccctt ttccatcact     1980
aaaaatcaca gagcagtcag agggacccag taagaccaaa ggaggggagg acagagcatg     2040
aaaaccaaaa tccatgcaaa tgaaatgtaa ttggcacgac cctcacccccc aaatcttaca    2100 tctcaattcc catcctaaaa agcactcata ctttatgcat ccccgcagct acacacacac    2160
aacacacagc acacgcatga acacagcaca cacgagca cagcacacac acaaacgcac       2220
agcacacaca gcacacagat gagcacacag cacacacaca aacgcacagc acacacacgc    2280
acacacatgc acacacagca cacaaacgca cggcacacac acgcacacac atgcacacac    2340
agcacacaca caaacgcaca gcacacacaa acgcacagca cacgcaca cacagcacac     2400 acacgagcac acagcacaca aacgcacagc acacgcacac acatgcacac acagcacaca    2460
cactagcaca cagcacacac acaaagacac agcacacaca tgcacacaca gcacacac    2520 gcgaacacag cacacacgaa cacagcacac acagcacaca cacaaacaca gcacacacat    2580
gcacacagca cacgcacaca cagcacacac atgaacacag cacacagcac acacatgcac    2640
acacagcaca cacgcatgca cagcacacat gaacacagca cacacaaa cacacagcac     2700 acacatgcac acacagcaca cacactcatg cgcagcacat acatgaacac agctcacagc     2760
acacaaacac gcagcacaca cgttgcacac gcaagcaccc acctgcacac acacatgcgc    2820
acacacacgc acaccccac aaaattggat gaaaacaata agcatatcta agcaactacg     2880
atatctgtat ggatcaggcc aaagtccgc taagattctc caatgttttc atggtctgag      2940
ccccgctcct gttcccatct ccactgcccc tcggccctgt ctgtgccctg cctctcagag    3000
```

```
gaggggggctc agatggtgcg gcctgagtgt gcggccggcg gcatttggga tacacccgta   3060
gggtgggcgg ggtgtgtccc aggcctaatt ccatctttcc accatgacag agatgccctt   3120
gtgaggctgg cctccttggc gcctgtcccc acggcccccg cagcgtgagc cacgatgctc   3180
cccataccccc acccattccc gatacacctt acttactgtg tgttggccca gccagagtga   3240
ggaaggagtt tggccacatt ggagatggcg gtagctgagc agacatgccc ccacgagtag   3300
cctgactccc tggtgtgctc ctggaaggaa gatcttgggg accccccac cggagcacac    3360
ctagggatca tctttgcccg tctcctgggg accccccaag aaatgtggag tcctcggggg   3420
ccgtgcactg atgcggggag tgtgggaagt ctggcggttg gaggggtggg tggggggcag   3480
tggggggctgg gcgggggggag ttctggggta ggaagtggtc ccgggagatt ttggatggaa   3540
aagtcaggag gattgacagc agacttgcag aattacatag agaaattagg aaccccccaaa   3600
tttcatgtca attgatctat tcccctctt tgtttcttgg ggcattttc cttttttttt     3660
ttttttttgtt tttttttac ccctccttag ctttatgcgc tcagaaacca aattaaaccc   3720
ccccccatg taacaggggg gcagtgacaa agcaagaac gcacgaagcc agcctggaga     3780
ccaccacgtc ctgcccccccg ccatttatcg ccctgattgg attttgtttt tcatctgtcc  3840
ctgttgcttg ggttgagttg agggtggagc ctcctggggg gcactggcca ctgagccccc  3900
ttggagaagt cagaggggag tggagaaggc cactgtccgg cctggcttct ggggacagtg   3960
gctggtcccc agaagtcctg agggcggagg ggggggttgg gcagggtctc ctcaggtgtc   4020
aggagggtgc tcggaggcca caggaggggg ctcctggctg gcctgaggct ggccggaggg   4080
gaaggggcta gcaggtgtgt aaacagaggg ttccatcagg ctggggcagg gtggccgcct   4140
tccgcacact tgaggaaccc tcccctctcc ctcggtgaca tcttgcccgc ccctcagcac   4200
cctgccttgt ctccaggagg tccgaagctc tgtgggacct cttgggggca aggtggggtg   4260
aggccggggga gtagggaggt caggcgggtc tgagcccaca gagcaggaga gctgccaggt   4320
ctgcccatcg accaggttgc ttgggccccg gagcccacgg gtctggtgat gccatagcag   4380
ccaccaccgc ggcgcctagg gctgcggcag ggactcggcc tctgggaggt ttacctcgcc   4440
cccacttgtg cccccagctc agcccccctg cacgcagccc gactagcagt ctagaggcct   4500
gaggcttctg ggtcctggtg acggggctgg catgaccccg ggggtcgtcc atgccagtcc   4560
gcctcagtcg cagagggtcc ctcggcaagc gccctgtgag tgggccattc ggaacattgg   4620
acagaagccc aaagagccaa attgtcacaa ttgtggaacc cacattggcc tgagatccaa   4680
aacgcttcga ggcaccccaa attacctgcc cattcgtcag acacccacc cacccagtgt    4740
tatattctgc ctcgccggag tgggtgttcc cgggggcact tgccgaccag ccccttgcgt   4800
ccccaggttt gcagctctcc cctgggccac taaccatcct ggcccgggct gcctgtctga   4860
cctccgtgcc tagtcgtggc tctccatctt gtctcctccc cgtgtcccca atgtcttcag   4920
tgggggggccc cctcttgggt cccctcctct gccatcacct gaagaccccc acgccaaaca   4980
ctgaatgtca cctgtgcctg ccgcctcggt ccaccttgcg gcccgtgttt gactcaactc   5040
aactcctttta acgctaatat ttccggcaaa atcccatgct tgggttttgt ctttaacctt  5100
gtaacgcttg caatcccaat aaagcattaa aagtcatgaa aaaaaaaaaa aaaaaa       5156
```

<210> SEQ ID NO 3
<211> LENGTH: 5182
<212> TYPE: DNA
<213> ORGANISM: Homo sapiens

<400> SEQUENCE: 3

```
cgcctgtccc cctcccgagg cccgggctcg cgacggcaga gggctccgtc ggcccaaacc    60
gagctgggcg cccgcggtcc gggtgcagcc tccactccgc cccccagtca ccgcctcccc   120
cggcccctcg acgtggcgcc cttccctccg cttctctgtg ctcccgcgc ccctcttggc    180 gtctggcccc ggccccgct cttttctccg caaccttccc ttcgctccct cccgtccccc    240
ccagctccta gcctccgact ccctccccc ctcacgcccg ccctctcgcc ttcgccgaac    300
caaagtggat taattacacg cttttctgttt ctctccgtgc tgttctctcc cgctgtgcgc   360
ctgcccgcct ctcgctgtcc tctctcccc tcgcctctc ttcggccccc cccttcacg     420 ttcactctgt ctctcccact atctctgccc ccctctatcc ttgatacaac agctgacctc   480
atttcccgat accttttccc ccccgaaaag tacaacatct ggcccgcccc agcccgaaga   540
cagcccgtcc tccctggaca atcagacgaa ttctcccccc cccccaaaa aaaagccatc    600 cccccgctct gccccgtcgc acattcggcc cccgcgactc ggccagagcg gcgctggcag   660
aggagtgtcc ggcaggaggg ccaacgcccg ctgttcggtt tgcgacacgc agcagggagg   720
tgggcggcag cgtcgccggc ttccagacac caatgggaat cccaatgggg aagtcgatgc    780
tggtgcttct caccttcttg gccttcgcct cgtgctgcat tgctgcttac cgccccagtg    840
agaccctgtg cggcggggag ctggtggaca ccctccagtt cgtctgtggg gaccgcggct   900
tctacttcag caggcccgca agccgtgtga gccgtcgcag ccgtggcatc gttgaggagt   960 gctgttttccg cagctgtgac ctggccctcc tggagacgta ctgtgctacc cccgccaagt  1020
ccgagaggga cgtgtcgacc cctccgaccg tgcttccgga caacttcccc agatacccg    1080 tgggcaagtt cttccaatat gacacctgga agcagtccac ccagcgcctg cgcaggggcc   1140
tgcctgccct cctgcgtgcc cgccggggtc acgtgctcgc caaggagctc gaggcgttca   1200
gggaggccaa acgtcaccgt cccctgattg ctctacccac ccaagacccc gcccacgggg   1260
gcgccccccc agagatggcc agcaatcgga agtgagcaaa actgccgcaa gtctgcagcc   1320
cggcgccacc atcctgcagc ctcctcctga ccacggacgt ttccatcagg ttccatcccg   1380
aaaatctctc ggttccacgt cccctgggg cttctcctga cccagtcccc gtgccccgcc    1440
tccccgaaac aggctactct cctcggcccc ctccatcggg ctgaggaagc acagcagcat   1500
cttcaaacat gtacaaaatc gattggcttt aaacacccctt cacatacccct cccccccaat  1560 tatcccccaat tatccccaca cataaaaaat caaaacatta aactaaccc cttcccccc    1620 ccccacaaca accctcttaa aactaattgg cttttttagaa acaccccaca aaagctcaga   1680
aattggcttt aaaaaaaca accaccaaaa aaatcaatt ggctaaaaaa aaaaagtatt      1740
aaaaacgaat tggctgagaa acaattggca aaataaagga atttggcact ccccaccccc    1800
ctctttctct tctcccttgg actttgagtc aaattggcct ggacttgagt ccctgaacca   1860
gcaaagagaa aagaaggacc ccagaaatca caggtgggca cgtcgctgct accgccatct   1920
cccttctcac gggaattttc agggtaaact ggcatccga aaatagcaac aacccagact    1980
ggctcctcac tccctttcc atcactaaaa atcacagagc agtcagaggg acccagtaag    2040
accaaaggag gggaggacag agcatgaaaa ccaaaatcca tgcaaatgaa atgtaattgg   2100
cacgaccctc accccaaat cttacatctc aattcccatc ctaaaaagca ctcatacttt   2160
atgcatcccc gcagctacac acacacaaca cacagcacac gcatgaacac agcacacaca   2220
cgagcacagc acacacacaa acgcacagca cacagacgac acagatgagc acacagcaca   2280
cacacaaacg cacagcacac acacgcacac acatgcacac acagcacaca aacgcacggc   2340
```

| | | | | | |
|---|---|---|---|---|---|
| acacacacgc | acacacatgc | acacacagca | cacacacaaa | cgcacagcac | acacaaacgc | 2400 |
| acagcacaca | cgcacacaca | gcacacacac | gagcacacag | cacacaaacg | cacagcacac | 2460 |
| gcacacacat | gcacacacag | cacacacact | agcacacagc | acacacacaa | agacacagca | 2520 |
| cacacatgca | cacacagcac | acacgcgca | acacagcaca | cacgaacaca | gcacacacag | 2580 |
| cacacacaca | aacacagcac | acacatgcac | acagcacacg | cacacacagc | acacacatga | 2640 |
| acacagcaca | cagcacacac | atgcacacac | agcacacacg | catgcacagc | acacatgaac | 2700 |
| acagcacaca | cacaaacaca | cagcacacac | atgcacacac | agcacacaca | ctcatgcgca | 2760 |
| gcacatacat | gaacacagct | cacagcacac | aaacacgcag | cacacacgtt | gcacacgcaa | 2820 |
| gcacccacct | gcacacacac | atgcgcacac | acacgcacac | ccccacaaaa | ttggatgaaa | 2880 |
| acaataagca | tatctaagca | actacgatat | ctgtatggat | caggccaaag | tcccgctaag | 2940 |
| attctccaat | gttttcatgg | tctgagcccc | gctcctgttc | ccatctccac | tgcccctcgg | 3000 |
| ccctgtctgt | gccctgcctc | tcagaggagg | gggctcagat | ggtgcggcct | gagtgtgcgg | 3060 |
| ccggcggcat | ttgggataca | cccgtagggt | gggcggggtg | tgtcccaggc | ctaattccat | 3120 |
| cttttccacca | tgacagagat | gcccttgtga | ggctggcctc | cttggcgcct | gtccccacgg | 3180 |
| cccccgcagc | gtgagccacg | atgctcccca | taccccaccc | attcccgata | caccttactt | 3240 |
| actgtgtgtt | ggcccagcca | gagtgaggaa | ggagtttggc | cacattggag | atggcggtag | 3300 |
| ctgagcagac | atgcccccac | gagtagcctg | actcctggt | gtgctcctgg | aaggaagatc | 3360 |
| ttggggaccc | ccccaccgga | gcacacctag | ggatcatctt | tgcccgtctc | ctggggaccc | 3420 |
| cccaagaaat | gtggagtcct | cgggggccgt | gcactgatgc | ggggagtgtg | ggaagtctgg | 3480 |
| cggttggagg | ggtgggtggg | gggcagtggg | ggctgggcgg | ggggagttct | ggggtaggaa | 3540 |
| gtggtcccgg | gagattttgg | atggaaaagt | caggaggatt | gacagcagac | ttgcagaatt | 3600 |
| acatagagaa | attaggaacc | cccaaatttc | atgtcaattg | atctattccc | cctctttgtt | 3660 |
| tcttggggca | ttttttccttt | ttttttttttt | tttgttttttt | ttttaccccct | ccttagcttt | 3720 |
| atgcgctcag | aaaccaaatt | aaaccccccc | cccatgtaac | agggggcag | tgacaaaagc | 3780 |
| aagaacgcac | gaagccagcc | tggagaccac | cacgtcctgc | ccccgccat | ttatcgccct | 3840 |
| gattggattt | tgttttcat | ctgtccctgt | tgcttgggtt | gagttgaggg | tggagcctcc | 3900 |
| tgggggcac | tggccactga | gccccttgg | agaagtcaga | ggggagtgga | gaaggccact | 3960 |
| gtccggcctg | gcttctgggg | acagtggctg | gtccccagaa | gtcctgaggg | cggaggggg | 4020 |
| ggttgggcag | ggtctcctca | ggtgtcagga | gggtgctcgg | aggccacagg | aggggctcc | 4080 |
| tggctggcct | gaggctggcc | ggaggggaag | gggctagcag | gtgtgtaaac | agagggttcc | 4140 |
| atcaggctgg | ggcagggtgg | ccgccttccg | cacacttgag | gaaccctccc | ctctccctcg | 4200 |
| gtgacatctt | gcccgcccct | cagcaccctg | ccttgtctcc | aggaggtccg | aagctctgtg | 4260 |
| ggacctcttg | ggggcaaggt | gggggtgaggc | cggggagtag | ggaggtcagg | cgggtctgag | 4320 |
| cccacagagc | aggagagctg | ccaggtctgc | ccatcgacca | ggttgcttgg | gccccggagc | 4380 |
| ccacgggtct | ggtgatgcca | tagcagccac | caccgcggcg | cctagggctg | cggcagggac | 4440 |
| tcggcctctg | ggaggtttac | ctcgccccca | cttgtgcccc | cagctcagcc | ccctgcacg | 4500 |
| cagcccgact | agcagtctag | aggcctgagg | cttctgggtc | ctggtgacgg | ggctggcatg | 4560 |
| accccgggg | tcgtccatgc | cagtccgcct | cagtcgcaga | gggtccctcg | gcaagcgccc | 4620 |
| tgtgagtggg | ccattcggaa | cattggacag | aagcccaaag | agccaaattg | tcacaattgt | 4680 |
| ggaacccaca | ttggcctgag | atccaaaacg | cttcgaggca | cccccaaatta | cctgcccatt | 4740 |

| | |
|---|---:|
| cgtcaggaca cccacccacc cagtgttata ttctgcctcg ccggagtggg tgttcccggg | 4800 |
| ggcacttgcc gaccagcccc ttgcgtcccc aggtttgcag ctctcccctg ggccactaac | 4860 |
| catcctggcc cgggctgcct gtctgacctc cgtgcctagt cgtggctctc catcttgtct | 4920 |
| cctcccgtg tccccaatgt cttcagtggg gggcccctc ttgggtcccc tcctctgcca | 4980 |
| tcacctgaag accccacgc caaacactga atgtcacctg tgcctgccgc ctcggtccac | 5040 |
| cttgcggccc gtgtttgact caactcaact cctttaacgc taatatttcc ggcaaaatcc | 5100 |
| catgcttggg ttttgtcttt aaccttgtaa cgcttgcaat cccaataaag cattaaaagt | 5160 |
| catgaaaaaa aaaaaaaaaa aa | 5182 |

<210> SEQ ID NO 4
<211> LENGTH: 4856
<212> TYPE: DNA
<213> ORGANISM: Homo sapiens

<400> SEQUENCE: 4

| | |
|---|---:|
| ggccgcgcgc cctcaggacg tggacaggga gggcttcccc gtgtccagga aagcgaccgg | 60 |
| gcattgcccc cagtctcccc caaatttggg cattgtcccc gggtcttcca acggactggg | 120 |
| cgttgctccc ggacactgag gactggcccc ggggtctcgc tcaccttcag cagcgtccac | 180 |
| cgcctgccac agagcgttcg atcgctcgct gcctgagctc ctggtgcgcc cgcggacgca | 240 |
| gcctccagct tcgcggagat ggtttcccca gaccccaaa ttatcgtggt ggccccgag | 300 |
| accgaactcg cgtctatgca agtccaacgc actgaggacg gggtaaccat tatccagata | 360 |
| ttttgggtgg gccgcaaagg cgagctactt agacgcaccc cggtgagctc ggccatgcag | 420 |
| acaccaatgg gaatcccaat ggggaagtcg atgctggtgc ttctcacctt cttggccttc | 480 |
| gcctcgtgct gcattgctgc ttaccgcccc agtgagaccc tgtgcggcgg ggagctggtg | 540 |
| gacacccctcc agttcgtctg tggggaccgc ggcttctact tcagcaggcc cgcaagccgt | 600 |
| gtgagccgtc gcagccgtgg catcgttgag gagtgctgtt ccgcagctg tgacctggcc | 660 |
| ctcctggaga cgtactgtgc taccccgcc aagtccgaga gggacgtgtc gacccctccg | 720 |
| accgtgcttc cggacaactt ccccagatac cccgtgggca agttcttcca atatgacacc | 780 |
| tggaagcagt ccacccagcg cctgcgcagg ggcctgcctg ccctcctgcg tgcccgccgg | 840 |
| ggtcacgtgc tcgccaagga gctcgaggcg ttcagggagg ccaaacgtca ccgtccctg | 900 |
| attgctctac ccacccaaga ccccgcccac gggggcgccc cccagagat ggccagcaat | 960 |
| cggaagtgag caaaactgcc gcaagtctgc agcccggcgc caccatcctg cagcctcctc | 1020 |
| ctgaccacgg acgtttccat caggttccat cccgaaaatc tctcggttcc acgtccccct | 1080 |
| ggggcttctc ctgacccagt ccccgtgccc cgcctcccg aaacaggcta ctctcctcgg | 1140 |
| cccctccat cgggctgagg aagcacagca gcatcttcaa acatgtacaa aatcgattgg | 1200 |
| ctttaaacac ccttcacata ccctccccc aaattatccc caattatccc cacacataaa | 1260 |
| aaatcaaaac attaaactaa ccccttccc cccccccac aacaaccctc ttaaaactaa | 1320 |
| ttggcttttt agaaacaccc cacaaaagct cagaaattgg ctttaaaaaa aacaaccacc | 1380 |
| aaaaaaaatc aattggctaa aaaaaaaaag tattaaaaac gaattggctg agaaacaatt | 1440 |
| ggcaaaataa aggaatttgg cactccccac cccctcttt ctcttctccc ttggactttg | 1500 |
| agtcaaattg gcctggactt gagtccctga accagcaaag agaaagaag gaccccagaa | 1560 |
| atcacaggtg ggcacgtcgc tgctaccgcc atctcccttc tcacgggaat tttcagggta | 1620 |

-continued

```
aactggccat ccgaaaatag caacaaccca gactggctcc tcactcccctt ttccatcact    1680 aaaaatcaca gagcagtcag agggacccag taagaccaaa ggaggggagg acagagcatg    1740
aaaaccaaaa tccatgcaaa tgaaatgtaa ttggcacgac cctcaccccc aaatcttaca    1800
tctcaattcc catcctaaaa agcactcata ctttatgcat ccccgcagct acacacacac    1860
aacacacagc acacgcatga acacagcaca cacacgagca cagcacacac acaaacgcac    1920
agcacacaca gcacacagat gagcacacag cacacacaca aacgcacagc acacacacgc    1980
acacacatgc acacagcaca cacaaacgca cggcacacac acgcacacac atgcacacac    2040
agcacacaca caaacgcaca gcacacacaa acgcacagca cacgcacaca cacagcacac    2100
acacgagcac acagcacaca aacgcacagc acacgcacac acatgcacac acagcacaca    2160
cactagcaca cagcacacac acaaagacac agcacacaca tgcacacaca gcacacacac    2220
gcgaacacag cacacacgaa cacagcacac acagcacaca cacaaacaca gcacacacat    2280
gcacacagca cacgcacaca cagcacacac atgaacacag cacacagcac acacatgcac    2340
acacagcaca cacgcatgca cagcacacat gaacacagca cacacacaaa cacacagcac    2400
acacatgcac acacagcaca cacactcatg cgcagcacat acatgaacac agctcacagc    2460 acacaaaacac gcagcacaca cgttgcacac gcaagcaccc acctgcacac acacatgcgc    2520
acacacacgc acaccccccac aaaattggat gaaaacaata agcatatcta agcaactacg    2580
atatctgtat ggatcaggcc aaagtcccgc taagattctc caatgttttc atggtctgag    2640
ccccgctcct gttcccatct ccactgcccc tcggccctgt ctgtgccctg cctctcagag    2700
gagggggctc agatggtgcg gcctgagtgt gcggccggcg gcatttggga tacaccgta    2760 gggtgggcgg ggtgtgtccc aggcctaatt ccatctttcc accatgacag agatgcccctt   2820 gtgaggctgg cctccttggc gcctgtcccc acggcccccg cagcgtgagc cacgatgctc    2880
cccatacccc acccattccc gatacacctt acttactgtg tgttggccca gccagagtga    2940
ggaaggagtt tggccacatt ggagatggcg gtagctgagc agacatgccc ccacgagtag    3000
cctgactccc tggtgtgctc ctggaaggaa gatcttgggg accccccac cggagcacac    3060 ctagggatca tctttgcccg tctcctgggg acccccaag aaatgtggag tcctcggggg    3120
ccgtgcactg atgcggggag tgtgggaagt ctggcggttg gaggggtggg tggggggcag    3180
tgggggctgg gcgggggggag ttctgggggta ggaagtggtc ccgggagatt ttggatggaa    3240
aagtcaggag gattgacagc agacttgcag aattacatag agaaattagg aaccccccaaa    3300 tttcatgtca attgatctat tcccccctctt tgtttcttgg ggcattttttc cttttttttt    3360 ttttttttgtt ttttttttac ccctccttag ctttatgcgc tcagaaacca aattaaaccc    3420
cccccccatg taacagggggg gcagtgacaa aagcaagaac gcacgaagcc agcctggaga    3480
ccaccacgtc ctgccccccg ccatttatcg ccctgattgg atttttgtttt tcatctgtcc    3540 ctgttgcttg ggttgagttg agggtggagc ctcctgggg gcactggcca ctgagccccc    3600
ttggagaagt cagagggggag tggagaaggc cactgtccgg cctggcttct ggggacagtg    3660
gctggtcccc agaagtcctg agggcggagg ggggggttgg gcagggtctc ctcaggtgtc    3720
aggagggtgc tcggaggcca caggaggggg ctcctggctg gcctgaggct ggccggaggg    3780
gaaggggcta gcaggtgtgt aaacagaggg ttccatcagg ctggggcagg gtggccgcct    3840
tccgcacact tgaggaaccc tccctctcc ctcggtgaca tcttgcccgc ccctcagcac    3900
cctgccttgt ctccaggagg tccgaagctc tgtgggacct cttgggggca aggtggggtg    3960
aggccgggga gtagggaggt caggcgggtc tgagcccaca gagcaggaga gctgccaggt    4020
```

```
ctgcccatcg accaggttgc ttgggccccg agcccacgg gtctggtgat gccatagcag    4080
ccaccaccgc ggcgcctagg gctgcggcag ggactcggcc tctgggaggt ttacctcgcc    4140
cccacttgtg cccccagctc agccccctg cacgcagccc gactagcagt ctagaggcct     4200
gaggcttctg gtcctggtg acggggctgg catgaccccg ggggtcgtcc atgccagtcc     4260
gcctcagtcg cagagggtcc ctcggcaagc gccctgtgag tgggccattc ggaacattgg    4320
acagaagccc aaagagccaa attgtcacaa ttgtggaacc cacattggcc tgagatccaa    4380
aacgcttcga ggcaccccaa attacctgcc cattcgtcag gacacccacc cacccagtgt    4440
tatattctgc ctcgccggag tgggtgttcc cgggggcact tgccgaccag ccccttgcgt    4500
ccccaggttt gcagctctcc cctgggccac taaccatcct ggcccgggct gcctgtctga    4560
cctccgtgcc tagtcgtggc tctccatctt gtctcctccc cgtgtcccca atgtcttcag    4620
tgggggcccc cctcttgggt cccctcctct gccatcacct gaagaccccc acgccaaaca    4680
ctgaatgtca cctgtgcctg ccgcctcggt ccaccttgcg gccgtgtttt gactcaactc    4740 aactcctta acgctaatat ttccggcaaa atcccatgct tgggttttgt ctttaacctt     4800
gtaacgcttg caatcccaat aaagcattaa aagtcatgaa aaaaaaaaaa aaaaaa        4856

<210> SEQ ID NO 5
<211> LENGTH: 1805
<212> TYPE: DNA
<213> ORGANISM: Homo sapiens

<400> SEQUENCE: 5
gagacacact ctgccccaac catcctgaag ctacaggtgc tccctcctgg aatctccaat      60
ggatttcagt cgcagaagct tccacagaag cctgagctcc tccttgcagg cccctgtagt    120
cagtacagtg ggcatgcagc gcctcgggac gacacccagc gtttatgggg gtgctggagg    180
ccggggcatc cgcatctcca actccagaca cacggtgaac tatgggagcg atctcacagg    240
cggcggggac ctgtttgttg gcaatgagaa aatggccatg cagaacctaa atgaccgtct    300
agcgagctac ctagaaaagg tgcggaccct ggagcagtcc aactccaaac ttgaagtgca    360
aatcaagcag tggtacgaaa ccaacgcccc gagggctggt cgcgactaca gtgcatatta    420
cagacaaatt gaagagctgc gaagtcagat taaggatgct caactgcaaa atgctcggtg    480
tgtcctgcaa attgataatg ctaaactggc tgctgaggac ttcagactga agtatgagac    540
tgagagagga atacgtctaa cagtggaagc tgatctccaa ggcctgaata aggtctttga    600
tgacctaacc ctacataaaa cagatttgga gattcaaatt gaagaactga ataaagacct    660
agctctcctc aaaaaggagc atcaggagga agtcgatggc ctacacaagc atctgggcaa    720
cactgtcaat gtggaggttg atgctgctcc aggcctgaac cttggcgtca tcatgaatga    780
aatgaggcag aagtatgaag tcatggccca gaagaacctt caagaggcca agaacagtt     840 tgagagacag actgcagttc tgcagcaaca ggtcacagtg aatactgaag aattaaaagg    900
aactgaggtt caactaacgg agctgagacg cacctcccag agccttgaga tagaactcca    960
gtcccatctc agcatgaaag agtctttgga gcacactcta gaggagacca aggcccgtta   1020
cagcagccaa ttagccaacc tccagtcgct gttgagctct ctggaggccc aactgatgca   1080
gattcggagt aacatggaac gccagaacaa cgaataccat atccttcttg acataaagac   1140
tcgacttgaa caggaaattg ctacttaccg ccgccttctg gaaggagaag acgtaaaaac   1200
tacagaatat cagttaagca ccctggaaga gagagatata aagaaaacca ggaagattaa   1260
```

```
gacagtcgtg caagaagtag tggatggcaa ggtcgtgtca tctgaagtca aagaggtgga    1320
agaaaatatc taaatagcta ccagaaggag atgctgctga ggttttgaaa gaaatttggc    1380
tataatctta tctttgctcc ctgcaagaaa tcagccataa gaaagcacta ttaatactct    1440
gcagtgatta gaagggtgg ggtggcggga atcctattta tcagactctg taattgaata    1500
taaatgtttt actcagagga gctgcaaatt gcctgcaaaa atgaaatcca gtgagcacta    1560
gaatatttaa aacatcatta ctgccatctt tatcatgaag cacatcaatt acaagctgta    1620
gaccacctaa tatcaatttg taggtaatgt tcctgaaaat tgcaatacat ttcaattata    1680
ctaaacctca caaagtagag gaatccatgt aaattgcaaa taaaccactt tctaattttt    1740
tcctgtttct gaattgtaaa accccctttg ggagtccctg gtttcttatt gagccaattt    1800
ctggg                                                                1805
```

<210> SEQ ID NO 6
<211> LENGTH: 1447
<212> TYPE: DNA
<213> ORGANISM: Homo sapiens

<400> SEQUENCE: 6

```
atccagattt gcttttacat tttcttgcct gagtctgagg tgaacagtga acatatttac      60
atttgattta acagtgaacc ttaattcttt ctggcttcac agtgaaacaa gtttatgcaa     120
tcgatcaaat attttcatcc ctgaggttaa caattaccat caaaatgttt tgtgagact      180 atgtgcaagg aaccatcttc ccagctccca atttcaatcc cataatggat gcccaaatgc     240
taggaggagc actccaagga tttgactgtg acaaagacat gctgatcaac attctgactc     300
agcgctgcaa tgcacaaagg atgatgattg cagaggcata ccagagcatg tatggccggg     360
acctgattgg ggatatgagg gagcagcttt cggatcactt caaagatgtg atggctggcc     420
tcatgtaccc accaccactg tatgatgctc atgagctctg gcatgccatg aagggagtag     480
gcactgatga gaattgcctc attgaaatac tagcttcaag aacaaatgga gaaattttcc     540
agatgcgaga agcctactgc ttgcaataca gcaataacct ccaagaggac atttattcag     600
agacctcagg acacttcaga gatactctca tgaacttggt ccaggggacc agagaggaag     660
gatatacaga ccctgcgatg gctgctcagg atgcaatggt cctatgggaa gcctgtcagc     720
agaagacggg ggagcacaaa accatgctgc aaatgatcct gtgcaacaag agctaccagc     780
agctgcggct ggttttccag gaatttcaaa atatttctgg gcaagatatg gtagatgcca     840
ttaatgaatg ttatgatgga tactttcagg agctgctggt tgcaattgtt ctctgtgttc     900
gagacaaacc agcctatttt gcttatagat tatatagtgc aattcatgac tttggtttcc     960
ataataaaac tgtaatcagg attctcattg ccagaagtga aatagacctg ctgaccataa    1020
ggaaacgata caaagagcga tatggaaaat ccctatttca tgatatcaga aattttgctt    1080
cagggcatta taagaaagca ctgcttgcca tctgtgctgg tgatgctgag gactactaaa    1140
atgaagagga cttggagtac tgtgcactcc tctttctaga cacttccaaa tagagatttt    1200
ctcacaaatt tgtactgttc atggcactat taacaaaact atacaatcat attttctctt    1260
ctatctttga aattattcta agccaaagaa aactatgaat gaaagtatat gatactgaat    1320
ttgcctacta tcctgaattt gcctactatc taatcagcaa ttaaataaat tgtgcatgat    1380
ggaataatag aaaaattgca ttggaataga ttttattta atgtgaacca tcaacaacct    1440
acaacaa                                                              1447
```

<210> SEQ ID NO 7
<211> LENGTH: 5881
<212> TYPE: DNA
<213> ORGANISM: Homo sapiens

<400> SEQUENCE: 7

| | | | | | | |
|---|---|---|---|---|---|---|
| ggttggtgac | ttccacagga | aaagttctgg | aggagtagcc | aaagaccatc | agcgtttcct | 60 |
| ttatgtgtga | gaattgaaat | gactagcatt | attgacccct | ttcagcatcc | cctgtgaata | 120 |
| tttctgttta | ggttttctt | cttgaaaaga | aattgttatt | cagcccgttt | aaaacaaatc | 180 |
| aagaaacttt | tgggtaacat | tgcaattaca | tgaaattgat | aaccgcgaaa | ataattggaa | 240 |
| ctcctgcttg | caagtgtcaa | cctaaaaaaa | gtgcttcctt | ttgttatgga | agatgtcttt | 300 |
| ctgtgattga | cttcaattgc | tgacttgtgg | agatgcagcg | aatgtgaaat | cccacgtata | 360 |
| tgccatttcc | ctctacgctc | gctgaccgtt | ctggaagatc | ttgaaccctc | ttctggaaag | 420 |
| gggtacctat | tattacttta | tggggcagca | gcctggaaaa | gtacttgggg | accaaagaag | 480 |
| gccaagcttg | cctgccctgc | attttatcaa | aggagcaggg | aagaaggaat | catcgaggca | 540 |
| tgggggtcca | cactgcaatg | ttttttgtgga | acatgaagcc | cttcagcggc | cagtagcatc | 600 |
| tgactttgag | cctcagggtc | tgagtgaagc | cgctcgttgg | aactccaagg | aaaaccttct | 660 |
| cgctggaccc | agtgaaaatg | accccaacct | tttcgttgca | ctgtatgatt | ttgtggccag | 720 |
| tggagataac | actctaagca | taactaaagg | tgaaaagctc | cgggtcttag | gctataatca | 780 |
| caatggggaa | tggtgtgaag | cccaaaccaa | aaatggccaa | ggctgggtcc | caagcaacta | 840 |
| catcacgcca | gtcaacagtc | tggagaaaca | ctcctggtac | catgggcctg | tgtcccgcaa | 900 |
| tgccgctgag | tatctgctga | gcagcgggat | caatggcagc | ttcttggtgc | gtgagagtga | 960 |
| gagcagtcct | ggccagaggt | ccatctcgct | gagatacgaa | gggagggtgt | accattacag | 1020 |
| gatcaacact | gcttctgatg | gcaagctcta | cgtctcctcc | gagagccgct | tcaacaccct | 1080 |
| ggccgagttg | gttcatcatc | attcaacggt | ggccgacggg | ctcatcacca | cgctccatta | 1140 |
| tccagcccca | aagcgcaaca | agcccactgt | ctatggtgtg | tcccccaact | acgacaagtg | 1200 |
| ggagatggaa | cgcacggaca | tcaccatgaa | gcacaagctg | gcggggggcc | agtacgggga | 1260 |
| ggtgtacgag | ggcgtgtgga | agaaatacag | cctgacggtg | gccgtgaaga | ccttgaagga | 1320 |
| ggacaccatg | gaggtggaag | agttcttgaa | agaagctgca | gtcatgaaag | agatcaaaca | 1380 |
| ccctaacctg | gtgcagctcc | ttgggggtctg | cacccgggag | cccccgttct | atatcatcac | 1440 |
| tgagttcatg | acctacggga | acctcctgga | ctacctgagg | gagtgcaacc | ggcaggaggt | 1500 |
| gaacgccgtg | gtgctgctgt | acatggccac | tcagatctcg | tcagccatgg | agtacctgga | 1560 |
| gaagaaaaac | ttcatccaca | gagatcttgc | tgcccgaaac | tgcctggtag | gggagaacca | 1620 |
| cttggtgaag | gtagctgatt | ttggcctgag | caggttgatg | acaggggaca | cctacacagc | 1680 |
| ccatgctgga | gccaagttcc | ccatcaaatg | gactgcaccc | gagagcctgg | cctacaacaa | 1740 |
| gttctccatc | aagtccgacg | tctgggcatt | tggagtattg | cttgggaaaa | ttgctaccta | 1800 |
| tggcatgtcc | ccttacccgg | gaattgacct | gtcccaggtg | tatgagctgc | tagagaagga | 1860 |
| ctaccgcatg | gagcgcccag | aaggctgccc | agagaaggtc | tatgaactca | tgcgagcatg | 1920 |
| ttggcagtgg | aatccctctg | accggccctc | ctttgctgaa | atccaccaag | cctttgaaac | 1980 |
| aatgttccag | gaatccagta | tctcagacga | agtggaaaag | gagctgggga | acaaggcgt | 2040 |
| ccgtgggggct | gtgagtacct | tgctgcaggc | cccagagctg | cccaccaaga | cgaggacctc | 2100 |
| caggagagct | gcagagcaca | gagacaccac | tgacgtgcct | gagatgcctc | actccaaggg | 2160 |

```
ccagggagag agcgatcctc tggaccatga gcctgccgtg tctccattgc tccctcgaaa    2220
agagcgaggt cccccggagg gcggcctgaa tgaagatgag cgccttctcc ccaaagacaa    2280
aaagaccaac ttgttcagcg ccttgatcaa gaagaagaag aagacagccc caaccectcc    2340 caaacgcagc agctccttcc gggagatgga cggccagccg gagcgcagag gggccggcga    2400
ggaagagggc cgagacatca gcaacggggc actggctttc accccttgg acacagctga    2460 cccagccaag tccccaaagc ccagcaatgg ggctggggtc cccaatggag ccctccggga    2520 gtccggggc tcaggcttcc ggtctcccca cctgtggaag aagtccagca cgctgaccag    2580
cagccgccta gccaccggcg aggaggaggg cggtggcagc tccagcaagc gcttcctgcg    2640
ctcttgctcc gcctcctgcg ttccccatgg ggccaaggac acggagtgga ggtcagtcac    2700
gctgcctcgg gacttgcagt ccacgggaag acagtttgac tcgtccacat ttggagggca    2760
caaaagtgag aagccggctc tgcctcggaa gagggcaggg gagaacaggt ctgaccaggt    2820
gacccgaggc acagtaacgc ctcccccag gctggtgaaa aagaatgagg aagctgctga    2880
tgaggtcttc aaagacatca tggagtccag cccgggctcc agcccgccca acctgactcc    2940
aaaacccctc cggcggcagg tcaccgtggc cctgcctcg gcctccccc acaaggaaga    3000 agctggaaag ggcagtgcct tagggacccc tgctgcagct gagccagtga cccccaccag    3060
caaagcaggc tcaggtgcac caggggcac cagcaagggc ccgccgagg agtccagagt    3120 gaggaggcac aagcactcct ctgagtcgcc agggagggac aaggggaaat tgtccaggct    3180
caaacctgcc ccgccgcccc caccagcagc ctctgcaggg aaggctggag gaaagccctc    3240
gcagagcccg agccaggagg cggccgggga gcagtcctg ggcgcaaaga caaaagccac    3300
gagtctggtt gatgctgtga acagtgacgc tgccaagccc agccagccgg gagagggcct    3360
caaaaagccc gtgctcccgg ccactccaaa gccacagtcc gccaagccgt cggggacccc    3420
catcagccca gccccgttc cctccacgtt gccatcagca tcctcggccc tggcagggga    3480
ccagccgtct tccaccgcct tcatccctct catatcaacc cgagtgtctc ttcggaaaac    3540
ccgccagcct ccagagcgga tcgccagcgg cgccatcacc aagggcgtgg tcctggacag    3600
caccgaggcg ctgtgcctcg ccatctctag gaactccgag cagatggcca gccacagcgc    3660
agtgctggag gccggcaaaa acctctacac gttctgcgtg agctatgtgg attccatcca    3720
gcaaatgagg aacaagtttg ccttccgaga ggccatcaac aaactggaga ataatctccg    3780
ggagcttcag atctgcccgg cgacagcagg cagtggtcca gcggccactc aggacttcag    3840
caagctcctc agttcggtga aggaaatcag tgacatagtg cagaggtagc agcagtcagg    3900
ggtcaggtgt caggcccgtc ggagctgcct gcagcacatg cgggctcgcc catacccgtg    3960
acagtggctg acaagggact agtgagtcag caccttggcc caggagctct gcgccaggca    4020
gagctgaggg ccctgtggag tccagctcta ctacctacgt ttgcaccgcc tgccctcccg    4080
caccttcctc ctccccgctc cgtctctgtc ctcgaatttt atctgtggag ttcctgctcc    4140
gtggactgca gtcggcatgc caggacccgc cagccccgct cccacctagt gccccagact    4200
gagctctcca ggccaggtgg gaacggctga tgtggactgt cttttcatt tttttctctc    4260 tggagcccct cctccccgg ctgggcctcc ttcttccact tctccaagaa tggaagcctg    4320
aactgaggcc ttgtgtgtca ggccctctgc ctgcactccc tggccttgcc cgtcgtgtgc    4380
tgaagacatg tttcaagaac cgcatttcgg gaagggcatg cacgggcatg cacacggctg    4440
gtcactctgc cctctgctgc tgcccggggt ggggtgcact cgccatttcc tcacgtgcag    4500
gacagctctt gatttgggtg gaaaacaggg tgctaaagcc aaccagcctt tgggtcctgg    4560
```

-continued

```
gcaggtggga gctgaaaagg atcgaggcat ggggcatgtc ctttccatct gtccacatcc    4620
ccagagccca gctcttgctc tcttgtgacg tgcactgtga atcctggcaa gaaagcttga    4680
gtctcaaggg tggcaggtca ctgtcactgc cgacatccct cccccagcag aatggaggca    4740
ggggacaagg gaggcagtgg ctagtggggt gaacagctgg tgccaaatag ccccagactg    4800
ggcccaggca ggtctgcaag ggcccagagt gaaccgtcct ttcacacatc tgggtgccct    4860
gaaagggccc ttcccctccc ccactcctct aagacaaagt agattcttac aaggcccttt    4920
cctttggaac aagacagcct tcacttttct gagttcttga agcatttcaa agccctgcct    4980
ctgtgtagcc gccctgagag agaatagagc tgccactggg cacctgcgca caggtgggag    5040
gaaagggcct ggccagtcct ggtcctggct gcactcttga actgggcgaa tgtcttattt    5100
aattaccgtg agtgacatag cctcatgttc tgtggggtc atcagggagg gttaggaaaa     5160
ccacaaacgg agccctgaaa gcctcacgt atttcacaga gcacgcctgc catcttctcc     5220
ccgaggctgc cccaggccgg agcccagata cgggggctgt gactctgggc agggacccgg    5280
ggtctcctgg accttgacag agcagctaac tccgagagca gtgggcaggt ggccgcccct    5340
gaggcttcac gccgggagaa gccaccttcc cacccttca taccgcctcg tgccagcagc     5400
ctcgcacagg ccctagcttt acgctcatca cctaaacttg tactttattt ttctgataga    5460
aatggtttcc tctggatcgt tttatgcggt tcttacagca catcacctct ttgccccga     5520 cggctgtgac gcagccggag ggaggcacta gtcaccgaca gcggccttga agacagagca    5580
aagcgcccac ccaggtcccc cgactgcctg tctccatgag gtactggtcc cttccttttg    5640
ttaacgtgat gtgccactat attttacacg tatctcttgg tatgcatctt ttatagacgc    5700
tcttttctaa gtggcgtgtg catagcgtcc tgccctgccc cctcggggc ctgtggtggc     5760 tccccctctg cttctcgggg tccagtgcat tttgtttctg tatatgattc tctgtggttt    5820 ttttttgaatc caaatctgtc ctctgtagta tttttaaat aaatcagtgt ttacattaga    5880
a                                                                    5881
```

<210> SEQ ID NO 8
<211> LENGTH: 24
<212> TYPE: DNA
<213> ORGANISM: Artificial sequence
<220> FEATURE:
<223> OTHER INFORMATION: Synthetic

<400> SEQUENCE: 8

```
gatcaacact gcttctgatg gcaa                                              24
```

<210> SEQ ID NO 9
<211> LENGTH: 25
<212> TYPE: DNA
<213> ORGANISM: Artificial sequence
<220> FEATURE:
<223> OTHER INFORMATION: Snythetic

<400> SEQUENCE: 9

```
ccaccgttga atgatgatga accaa                                             25
```

<210> SEQ ID NO 10
<211> LENGTH: 20
<212> TYPE: DNA
<213> ORGANISM: Artificial sequence
<220> FEATURE:
<223> OTHER INFORMATION: Snythetic

```
<400> SEQUENCE: 10
cctccgagag ccgcttcaac                                               20

<210> SEQ ID NO 11
<211> LENGTH: 20
<212> TYPE: DNA
<213> ORGANISM: Artificial sequence
<220> FEATURE:
<223> OTHER INFORMATION: Snythetic

<400> SEQUENCE: 11
cctccgagag ccgcttcaac                                               20

<210> SEQ ID NO 12
<211> LENGTH: 20
<212> TYPE: DNA
<213> ORGANISM: Artificial sequence
<220> FEATURE:
<223> OTHER INFORMATION: Snythetic

<400> SEQUENCE: 12
cctccgagag ccgcttcaac                                               20

<210> SEQ ID NO 13
<211> LENGTH: 22
<212> TYPE: DNA
<213> ORGANISM: Artificial sequence
<220> FEATURE:
<223> OTHER INFORMATION: Snythetic

<400> SEQUENCE: 13
ttgaagagct gcgaagtcag at                                            22

<210> SEQ ID NO 14
<211> LENGTH: 21
<212> TYPE: DNA
<213> ORGANISM: Artificial sequence
<220> FEATURE:
<223> OTHER INFORMATION: Snythetic

<400> SEQUENCE: 14
tgaagtcctc agcagccagt t                                             21

<210> SEQ ID NO 15
<211> LENGTH: 26
<212> TYPE: DNA
<213> ORGANISM: Artificial sequence
<220> FEATURE:
<223> OTHER INFORMATION: Snythetic

<400> SEQUENCE: 15
tcaactgcaa aatgctcggt gtgtcc                                        26

<210> SEQ ID NO 16
<211> LENGTH: 20
<212> TYPE: DNA
<213> ORGANISM: Artificial sequence
<220> FEATURE:
<223> OTHER INFORMATION: Snythetic

<400> SEQUENCE: 16
cgcggcttct acttcagcag                                               20

<210> SEQ ID NO 17
<211> LENGTH: 20
```

```
<212> TYPE: DNA
<213> ORGANISM: Artificial sequence
<220> FEATURE:
<223> OTHER INFORMATION: Snythetic

<400> SEQUENCE: 17
gcggaaacag cactcctcaa                                              20

<210> SEQ ID NO 18
<211> LENGTH: 20
<212> TYPE: DNA
<213> ORGANISM: Artificial sequence
<220> FEATURE:
<223> OTHER INFORMATION: Snythetic

<400> SEQUENCE: 18
tgtgagccgt cgcagccgtg                                              20

<210> SEQ ID NO 19
<211> LENGTH: 18
<212> TYPE: DNA
<213> ORGANISM: Artificial sequence
<220> FEATURE:
<223> OTHER INFORMATION: Snythetic

<400> SEQUENCE: 19
acccggctca cctgcgaa                                                18

<210> SEQ ID NO 20
<211> LENGTH: 18
<212> TYPE: DNA
<213> ORGANISM: Artificial sequence
<220> FEATURE:
<223> OTHER INFORMATION: Snythetic

<400> SEQUENCE: 20
ggactcccgc ggacacaa                                                18

<210> SEQ ID NO 21
<211> LENGTH: 23
<212> TYPE: DNA
<213> ORGANISM: Artificial sequence
<220> FEATURE:
<223> OTHER INFORMATION: Snythetic

<400> SEQUENCE: 21
tcctgggaag cgagtgcccc taa                                          23

<210> SEQ ID NO 22
<211> LENGTH: 21
<212> TYPE: DNA
<213> ORGANISM: Artificial sequence
<220> FEATURE:
<223> OTHER INFORMATION: Snythetic

<400> SEQUENCE: 22
ctgggaagcg agtgccccta a                                            21

<210> SEQ ID NO 23
<211> LENGTH: 22
<212> TYPE: DNA
<213> ORGANISM: Artificial sequence
<220> FEATURE:
<223> OTHER INFORMATION: Snythetic

<400> SEQUENCE: 23
```
ggctattctc ctcttggcag at                                              22

<210> SEQ ID NO 24
<211> LENGTH: 22
<212> TYPE: DNA
<213> ORGANISM: Artificial sequence
<220> FEATURE:
<223> OTHER INFORMATION: Snythetic

<400> SEQUENCE: 24
tgcttgagct ccagtcccta ag                                              22

<210> SEQ ID NO 25
<211> LENGTH: 22
<212> TYPE: DNA
<213> ORGANISM: Artificial sequence
<220> FEATURE:
<223> OTHER INFORMATION: Snythetic

<400> SEQUENCE: 25
agccgagaag gcggagtctg gc                                              22

<210> SEQ ID NO 26
<211> LENGTH: 27
<212> TYPE: DNA
<213> ORGANISM: Artificial sequence
<220> FEATURE:
<223> OTHER INFORMATION: Snythetic

<400> SEQUENCE: 26
gtgaaacaag tttatgcaat cgatcaa                                         27

<210> SEQ ID NO 27
<211> LENGTH: 22
<212> TYPE: DNA
<213> ORGANISM: Artificial sequence
<220> FEATURE:
<223> OTHER INFORMATION: Snythetic

<400> SEQUENCE: 27
gattgaaatt gggagctggg aa                                              22

<210> SEQ ID NO 28
<211> LENGTH: 29
<212> TYPE: DNA
<213> ORGANISM: Artificial sequence
<220> FEATURE:
<223> OTHER INFORMATION: Snythetic

<400> SEQUENCE: 28
tcatccctga ggttaacaat taccatcaa                                       29

<210> SEQ ID NO 29
<211> LENGTH: 25
<212> TYPE: DNA
<213> ORGANISM: Artificial sequence
<220> FEATURE:
<223> OTHER INFORMATION: Snythetic

<400> SEQUENCE: 29
cgactacagt gcatattaca gacaa                                           25

<210> SEQ ID NO 30
<211> LENGTH: 24
<212> TYPE: DNA
<213> ORGANISM: Artificial sequence

```
<220> FEATURE:
<223> OTHER INFORMATION: Snythetic

<400> SEQUENCE: 30
cagcagccag tttagcatta tcaa                                              24

<210> SEQ ID NO 31
<211> LENGTH: 26
<212> TYPE: DNA
<213> ORGANISM: Artificial sequence
<220> FEATURE:
<223> OTHER INFORMATION: Snythetic

<400> SEQUENCE: 31
tcaactgcaa aatgctcggt gtgtcc                                            26

<210> SEQ ID NO 32
<211> LENGTH: 20
<212> TYPE: DNA
<213> ORGANISM: Artificial sequence
<220> FEATURE:
<223> OTHER INFORMATION: Snythetic

<400> SEQUENCE: 32
ggaccgcggc ttctacttca                                                   20

<210> SEQ ID NO 33
<211> LENGTH: 19
<212> TYPE: DNA
<213> ORGANISM: Artificial sequence
<220> FEATURE:
<223> OTHER INFORMATION: Snythetic

<400> SEQUENCE: 33
ccaggtcaca gctgcggaa                                                    19

<210> SEQ ID NO 34
<211> LENGTH: 20
<212> TYPE: DNA
<213> ORGANISM: Artificial sequence
<220> FEATURE:
<223> OTHER INFORMATION: Snythetic

<400> SEQUENCE: 34
tgtgagccgt cgcagccgtg                                                   20

<210> SEQ ID NO 35
<211> LENGTH: 19
<212> TYPE: DNA
<213> ORGANISM: Artificial sequence
<220> FEATURE:
<223> OTHER INFORMATION: Snythetic

<400> SEQUENCE: 35
tgcgaagcgc ctgggaagc                                                    19

<210> SEQ ID NO 36
<211> LENGTH: 18
<212> TYPE: DNA
<213> ORGANISM: Artificial sequence
<220> FEATURE:
<223> OTHER INFORMATION: Snythetic

<400> SEQUENCE: 36
ggactcccgc ggacacaa                                                     18
```

<210> SEQ ID NO 37
<211> LENGTH: 21
<212> TYPE: DNA
<213> ORGANISM: Artificial sequence
<220> FEATURE:
<223> OTHER INFORMATION: Snythetic

<400> SEQUENCE: 37
tgcccctaac atgcggctgc c                                     21

<210> SEQ ID NO 38
<211> LENGTH: 19
<212> TYPE: DNA
<213> ORGANISM: Artificial sequence
<220> FEATURE:
<223> OTHER INFORMATION: Snythetic

<400> SEQUENCE: 38
tcagcgctgc aatgcacaa                                        19

<210> SEQ ID NO 39
<211> LENGTH: 22
<212> TYPE: DNA
<213> ORGANISM: Artificial sequence
<220> FEATURE:
<223> OTHER INFORMATION: Snythetic

<400> SEQUENCE: 39
ggccagccat cacatctttg aa                                    22

<210> SEQ ID NO 40
<211> LENGTH: 23
<212> TYPE: DNA
<213> ORGANISM: Artificial sequence
<220> FEATURE:
<223> OTHER INFORMATION: Snythetic

<400> SEQUENCE: 40
tagagcatgt atggccggga cct                                   23

<210> SEQ ID NO 41
<211> LENGTH: 24
<212> TYPE: DNA
<213> ORGANISM: Artificial sequence
<220> FEATURE:
<223> OTHER INFORMATION: Snythetic

<400> SEQUENCE: 41
gatcaacact gcttctgatg gcaa                                  24

<210> SEQ ID NO 42
<211> LENGTH: 25
<212> TYPE: DNA
<213> ORGANISM: Artificial sequence
<220> FEATURE:
<223> OTHER INFORMATION: Snythetic

<400> SEQUENCE: 42
ccaccgttga atgatgatga accaa                                 25

<210> SEQ ID NO 43
<211> LENGTH: 20
<212> TYPE: DNA
<213> ORGANISM: Artificial sequence
<220> FEATURE:
<223> OTHER INFORMATION: Snythetic

```
<400> SEQUENCE: 43
cctccgagag ccgcttcaac                                                    20

<210> SEQ ID NO 44
<211> LENGTH: 22
<212> TYPE: DNA
<213> ORGANISM: Artificial sequence
<220> FEATURE:
<223> OTHER INFORMATION: Snythetic

<400> SEQUENCE: 44
ggctattctc ctcttggcag at                                                 22

<210> SEQ ID NO 45
<211> LENGTH: 22
<212> TYPE: DNA
<213> ORGANISM: Artificial sequence
<220> FEATURE:
<223> OTHER INFORMATION: Snythetic

<400> SEQUENCE: 45
tgcttgagct ccagtcccta ag                                                 22

<210> SEQ ID NO 46
<211> LENGTH: 22
<212> TYPE: DNA
<213> ORGANISM: Artificial sequence
<220> FEATURE:
<223> OTHER INFORMATION: Snythetic

<400> SEQUENCE: 46
agccgagaag gcggagtctg gc                                                 22

<210> SEQ ID NO 47
<211> LENGTH: 500
<212> TYPE: RNA
<213> ORGANISM: Artificial sequence
<220> FEATURE:
<223> OTHER INFORMATION: Snythetic

<400> SEQUENCE: 47
gaugcucacu ucaucuaugg uuacccuggg acuuuuacac caacagaacu agcaucaucc        60
ucugcauggu caggucaugg aucggcaucc ugacaguuuc gggaauuagg caucugcagu       120
cuuacugcuc aucggcugau gaugcugcug uaaucccccau ccaagcaagc uugugauccu      180
ccgccauuau cccaaauggu auaacauuua ggacuuaaag cuaugcaauu acaccuugu        240 uuuucaacag caagaccuaa uauuuucuuu ucaucauuaa ugccuuuuga uggaucaggc       300
aaccauuuau aaauauguuc accagccgaa gucaguagug auugggguggu uccuggcuug      360 ggaucaugcc gcugcagagg cuauucuccu cuuggcagau ugucuguagc cgagaaggcg       420
gagucuggca augaugaugc auacagugua cgacagccuu agggacugga gcucaagcag       480
uguuuccuca accagucaca                                                   500

<210> SEQ ID NO 48
<211> LENGTH: 20
<212> TYPE: DNA
<213> ORGANISM: Artificial sequence
<220> FEATURE:
<223> OTHER INFORMATION: Snythetic

<400> SEQUENCE: 48
```
ctgcaatgca caaaggatga                                                    20

<210> SEQ ID NO 49
<211> LENGTH: 10661
<212> TYPE: DNA
<213> ORGANISM: Homo sapiens

<400> SEQUENCE: 49
cgagatcccg gggagccagc ttgctgggag agcgggacgg tccggagcaa gcccagaggc    60
agaggaggcg acagagggaa aaagggccga gctagccgct ccagtgctgt acaggagccg   120
aagggacgca ccacgccagc cccagcccgg ctccagcgac agccaacgcc tcttgcagcg   180
cggcggcttc gaagccgccg cccggagctg cccttcctc ttcggtgaag ttttaaaag    240
ctgctaaaga ctcggaggaa gcaaggaaag tgcctggtag gactgacggc tgcctttgtc   300
ctcctcctct ccaccccgcc tcccccacc ctgccttccc ccctcccc gtcttctctc    360
ccgcagctgc ctcagtcggc tactctcagc caacccccct caccacccctt ctccccaccc   420
gcccccccgc cccgtcggc ccagcgctgc cagcccgagt ttgcagagag gtaactccct   480
ttggctgcga gcgggcgagc tagctgcaca ttgcaaagaa ggctcttagg agccaggcga   540
ctggggagcg gcttcagcac tgcagccacg acccgcctgg ttaggctgca cgcggagaga   600
accctctgtt ttcccccact ctctctccac ctcctcctgc cttccccacc ccgagtgcgg   660
agccagagat caaaagatga aaaggcagtc aggtcttcag tagccaaaaa acaaaacaaa   720
caaaaacaaa aaagccgaaa taaaagaaaa agataataac tcagttctta tttgcaccta   780
cttcagtgga cactgaattt ggaaggtgga ggattttgtt tttttctttt aagatctggg   840
catcttttga atctacccctt caagtattaa gagacagact gtgagcctag cagggcagat   900
cttgtccacc gtgtgtcttc ttctgcacga gactttgagg ctgtcagagc gcttttttgcg   960
tggttgctcc cgcaagtttc cttctctgga gcttcccgca ggtgggcagc tagctgcagc  1020
gactaccgca tcatcacagc ctgttgaact cttctgagca agagaagggg aggcggggta  1080
agggaagtag gtggaagatt cagccaagct caaggatgga agtgcagtta gggctgggaa  1140
gggtctaccc tcggccgccg tccaagacct accgaggagc tttccagaat ctgttccaga  1200
gcgtgcgcga agtgatccag aacccgggcc ccaggcaccc agaggccgcg agcgcagcac  1260
ctccccggcgc cagtttgctg ctgctgcagc agcagcagca gcagcagcag cagcagcagc  1320
agcagcagca gcagcagcag cagcagcagc agcaagagac tagccccagg cagcagcagc  1380
agcagcaggg tgaggatggt tctccccaag cccatcgtag aggccccaca ggctacctgg  1440
tcctggatga ggaacagcaa ccttcacagc cgcagtcggc cctggagtgc caccccgaga  1500
gaggttgcgt cccagagcct ggagccgccg tggccgccag caaggggctg ccgcagcagc  1560
tgccagcacc tccggacgag gatgactcag ctgccccatc cacgttgtcc ctgctgggcc  1620
ccactttccc cggcttaagc agctgctccg ctgaccttaa agacatcctg agcgaggcca  1680
gcaccatgca actccttcag caacagcagc aggaagcagt atccgaaggc agcagcagcg  1740
ggagagcgag ggaggcctcg ggggctccca cttcctccaa ggacaattac ttaggggggca  1800
cttcgaccat ttctgacaac gccaaggagt tgtgtaaggc agtgtcggtg tccatgggcc  1860
tgggtgtgga ggcgttggag catctgagtc caggggaaca gcttcggggg gattgcatgt  1920
acgccccact tttgggagtt ccaccgcctg tgcgtcccac tccttgtgcc ccattggccg  1980
aatgcaaagg ttctctgcta gacgacacgc caggcaagag cactgaagat actgctgagt  2040
attccccttt caagggaggt tacaccaaag gctagaagg cgagagccta ggctgctctg  2100

```
gcagcgctgc agcagggagc tccgggacac ttgaactgcc gtctaccctg tctctctaca   2160
agtccggagc actggacgag gcagctgcgt accagagtcg cgactactac aactttccac   2220
tggctctggc cggaccgccg ccccctccgc cgcctcccca tccccacgct cgcatcaagc   2280
tggagaaccc gctggactac ggcagcgcct gggcggctgc ggcggcgcag tgccgctatg   2340
gggacctggc gagcctgcat ggcgcgggtg cagcgggacc cggttctggg tcaccctcag   2400
ccgccgcttc ctcatcctgg cacactctct tcacagccga agaaggccag ttgtatggac   2460
cgtgtggtgg tggtgggggt ggtggcggcg gcggcggcgg cggcggcggc ggcggcggcg   2520
gcggcggcgg cggcgaggcg ggagctgtag cccctacgg ctacactcgg cccctcagg   2580 ggctggcggg ccaggaaagc gacttcaccg cacctgatgt gtggtaccct ggcggcatgg   2640
tgagcagagt gccctatccc agtcccactt gtgtcaaaag cgaaatgggc cctggatgg   2700 atagctactc cggaccttac ggggacatgc gtttggagac tgccagggac catgttttgc   2760
ccattgacta ttactttcca ccccagaaga cctgcctgat ctgtggagat gaagcttctg   2820
ggtgtcacta tggagctctc acatgtggaa gctgcaaggt cttcttcaaa agagccgctg   2880
aagggaaaca gaagtacctg tgcgccagca gaaatgattg cactattgat aaattccgaa   2940
ggaaaaattg tccatcttgt cgtcttcgga atgttatga agcagggatg actctgggag   3000
cccggaagct gaagaaactt ggtaatctga aactacagga ggaaggagag gcttccagca   3060
ccaccagccc cactgaggag acaacccaga agctgacagt gtcacacatt gaaggctatg   3120
aatgtcagcc catctttctg aatgtcctgg aagccattga gccaggtgta gtgtgtgctg   3180
gacacgacaa caaccagccc gactcctttg cagccttgct ctctagcctc aatgaactgg   3240
gagagagaca gcttgtacac gtggtcaagt gggccaaggc cttgcctggc ttccgcaact   3300
tacacgtgga cgaccagatg gctgtcattc agtactcctg gatggggctc atggtgtttg   3360
ccatgggctg gcgatccttc accaatgtca actccaggat gctctacttc gcccctgatc   3420
tggttttcaa tgagtaccgc atgcacaagt cccggatgta cagccagtgt gtccgaatga   3480
ggcacctctc tcaagagttt ggatggctcc aaatcacccc ccaggaattc ctgtgcatga   3540
aagcactgct actcttcagc attattccag tggatgggct gaaaaatcaa aaattctttg   3600
atgaacttcg aatgaactac atcaaggaac tcgatcgtat cattgcatgc aaaagaaaaa   3660
atcccacatc ctgctcaaga cgcttctacc agctcaccaa gctcctggac tccgtgcagc   3720
ctattgcgag agagctgcat cagttcactt ttgacctgct aatcaagtca cacatggtga   3780
gcgtggactt tccggaaatg atggcagaga tcatctctgt gcaagtgccc aagatccttt   3840
ctgggaaagt caagcccatc tatttccaca cccagtgaag cattggaaac cctatttccc   3900 cacccccagct catgccccct ttcagatgtc ttctgcctgt tataactctg cactactcct   3960
ctgcagtgcc ttggggaatt tcctctattg atgtacagtc tgtcatgaac atgttcctga   4020
attctatttg ctgggctttt ttttttctctt tctctcctttt cttttttcttc ttccctccct   4080 atctaaccct cccatggcac cttcagactt tgcttcccat tgtggctcct atctgtgttt   4140
tgaatggtgt tgtatgcctt taaatctgtg atgatcctca tatggcccag tgtcaagttg   4200
tgcttgttta cagcactact ctgtgccagc cacacaaacg tttacttatc ttatgccacg   4260
ggaagtttag agagctaaga ttatctgggg aaatcaaaac aaaacaagc aaacaaaaaa   4320 aaaaagcaaa aacaaaacaa aaaataagcc aaaaaccctt gctagtgttt tttcctcaaa   4380
aataaataaa taaataaata aatacgtaca tacatacaca catacataca aacatataga   4440
```

```
aatccccaaa gaggccaata gtgacgagaa ggtgaaaatt gcaggcccat ggggagttac    4500
tgattttttc atctcctccc tccacgggag actttatttt ctgccaatgg ctattgccat    4560
tagagggcag agtgacccca gagctgagtt gggcagggg gtggacagag aggagaggac    4620
aaggagggca atggagcatc agtacctgcc cacagccttg gtccctgggg gctagactgc    4680
tcaactgtgg agcaattcat tatactgaaa atgtgcttgt tgttgaaaat ttgtctgcat    4740
gttaatgcct cacccccaaa ccctttttctc tctcactctc tgcctccaac ttcagattga    4800
cttttcaatag tttttctaag acctttgaac tgaatgttct cttcagccaa aacttggcga   4860
cttccacaga aaagtctgac cactgagaag aaggagagca gagatttaac cctttgtaag   4920
gccccatttg gatccaggtc tgctttctca tgtgtgagtc agggaggagc tggagccaga   4980
ggagaagaaa atgatagctt ggctgttctc ctgcttagga cactgactga atagttaaac   5040
tctcactgcc actaccttt ccccaccttt aaaagacctg aatgaagttt ctgccaaac    5100
tccgtgaagc cacaagcacc ttatgtcctc ccttcagtgt tttgtgggcc tgaatttcat   5160
cacactgcat ttcagccatg gtcatcaagc ctgtttgctt cttttgggca tgttcacaga   5220
ttctctgtta agagccccca ccaccaagaa ggttagcagg ccaacagctc tgacatctat   5280
ctgtagatgc cagtagtcac aaagatttct taccaactct cagatcgctg gagcccttag   5340
acaaactgga agaaggcat caaagggatc aggcaagctg ggcgtcttgc ccttgtcccc    5400
cagagatgat accctcccag caagtggaga agttctcact tccttcttta gagcagctaa   5460
aggggctacc cagatcaggg ttgaagagaa aactcaatta ccagggtggg aagaatgaag   5520
gcactagaac cagaaaccct gcaaatgctc ttccttgtcac ccagcatatc cacctgcaga   5580
agtcatgaga agagaaagg aacaaagagg agactctgac tactgaatta aaatcttcag    5640
cggcaaagcc taaagccaga tggacaccat ctggtgagtt tactcatcat cctcctctgc   5700
tgctgattct gggctctgac attgcccata ctcactcaga ttccccacct tgttgctgc    5760
ctcttagtca gagggaggcc aaaccattga gactttctac agaaccatgg cttcttccgg   5820
aaaggtctgg ttggtgtggc tccaatactt tgccacccat gaactcaggg tgtgccctgg   5880
gacactggtt ttatatagtc ttttggcaca cctgtgttct gttgacttcg ttcttcaagc   5940
ccaagtgcaa gggaaaatgt ccacctactt tctcatcttg gcctctgcct ccttacttag   6000
ctcttaatct catctgttga actcaagaaa tcaagggcca gtcatcaagc tgcccatttt   6060
aattgattca ctctgttttgt tgagaggata gtttctgagt gacatgatat gatccacaag   6120
ggtttccttc cctgatttct gcattgatat taatagccaa acgaacttca aaacagcttt   6180
aaataacaag ggagagggga acctaagatg agtaatatgc caatccaaga ctgctggaga   6240
aaactaaagc tgacaggttc ccttttttggg gtgggataga catgttctgg ttttctttat   6300
tattacacaa tctggctcat gtacaggatc acttttagct gttttaaaca gaaaaaaata    6360
tccaccactc ttttcagtta cactaggtta cattttaata ggtcctttac atctgttttg   6420
gaatgatttt catcttttgt gatacacaga ttgaattata tcattttcat atctctcctt   6480
gtaaatacta gaagctctcc tttacatttc tctatcaaat ttttcatctt tatgggtttc   6540
ccaattgtga ctcttgtctt catgaatata tgttttcat ttgcaaaagc caaaaatcag    6600
tgaaacagca gtgtaattaa agcaacaac tggattactc caaatttcca aatgacaaaa    6660
ctagggaaaa atagcctaca caagccttta ggcctactct ttctgtgctt gggtttgagt   6720
gaacaaagga gattttagct tggctctgtt ctcccatgga tgaaaggagg aggatttttt   6780
ttttcttttg gccattgatg ttctagccaa tgtaattgac agaagtctca ttttgcatgc   6840
```

```
gctctgctct acaaacagag ttggtatggt tggtatactg tactcacctg tgagggactg    6900
gccactcaga cccacttagc tggtgagcta aagatgagg atcactcact ggaaaagtca     6960
caaggaccat ctccaaacaa gttggcagtg ctcgatgtgg acgaagagtg aggaagagaa    7020
aaagaaggag caccagggag aaggctccgt ctgtgctggg cagcagacag ctgccaggat    7080
cacgaactct gtagtcaaag aaaagagtcg tgtggcagtt tcagctctcg ttcattgggc    7140
agctcgccta ggcccagcct ctgagctgac atgggagttg ttggattctt tgtttcatag    7200
cttttctat gccataggca atattgttgt tcttggaaag tttattattt ttttaactcc     7260
cttactctga gaaagggata ttttgaagga ctgtcatata tctttgaaaa aagaaaatct    7320
gtaatacata tatttttatg tatgttcact ggcactaaaa aatatagaga gcttcattct    7380
gtcctttggg tagttgctga ggtaattgtc caggttgaaa aataatgtgc tgatgctaga    7440
gtccctctct gtccatactc tacttctaaa tacatatagg catacatagc aagttttatt    7500
tgacttgtac tttaagagaa aatatgtcca ccatccacat gatgcacaaa tgagctaaca    7560
ttgagcttca agtagcttct aagtgtttgt ttcattaggc acagcacaga tgtggccttt    7620
ccccccttct ctcccttgat atctggcagg gcataaaggc ccaggccact tcctctgccc    7680
cttcccagcc ctgcaccaaa gctgcatttc aggagactct ctccagacag cccagtaact    7740
acccgagcat ggcccctgca tagccctgga aaaataagag gctgactgtc tacgaattat    7800
cttgtgccag ttgcccaggt gagagggcac tgggccaagg gagtggtttt catgtttgac    7860
ccactacaag gggtcatggg aatcaggaat gccaaagcac cagatcaaat ccaaaactta    7920
aagtcaaaat aagccattca gcatgttcag tttcttggaa aaggaagttt ctaccctga    7980
tgcctttgta ggcagatctg ttctcaccat taatcttttt gaaaatcttt taaagcagtt    8040
tttaaaaga gagatgaaag catcacatta tataaccaaa gattacattg tacctgctaa    8100
gataccaaaa ttcataaggg caggggggga gcaagcatta gtgcctcttt gataagctgt   8160
ccaaagacag actaaaggac tctgctggtg actgacttat aagagctttg tgggtttttt    8220
tttccctaat aatatacatg tttagaagaa ttgaaaataa tttcgggaaa atgggattat   8280
gggtccttca ctaagtgatt ttataagcag aactggcttt cctttctct agtagttgct    8340
gagcaaattg ttgaagctcc atcattgcat ggttggaaat ggagctgttc ttagccactg    8400
tgtttgctag tgcccatgtt agcttatctg aagatgtgaa acccttgctg ataagggagc    8460
atttaaagta ctagatttg cactagaggg acagcaggca gaaatcctta tttctgccca    8520
cttttggatgg cacaaaaagt tatctgcagt tgaaggcaga aagttgaaat acattgtaaa    8580
tgaatatttg tatccatgtt tcaaaattga aatatatata tatatatata tatatatata    8640
tatatatata tagtgtgtgt gtgtgttctg atagctttaa ctttctctgc atctttatat    8700
ttggttccag atcacacctg atgccatgta cttgtgagag aggatgcagt tttgtttgg    8760
aagctctctc agaacaaaca agacacctgg attgatcagt taactaaaag tttcctcccc    8820
tattgggttt gacccacagg tcctgtgaag gagcagaggg ataaaaagag tagaggacat    8880
gatacattgt actttactag ttcaagacag atgaatgtgg aaagcataaa aactcaatgg    8940
aactgactga gatttaccac agggaaggcc caaacttggg gccaaaagcc tacccaagtg    9000
attgaccagt ggcccctaa tgggacctga gctgttggaa gaagagaact gttccttggt    9060
cttcaccatc cttgtgagag aagggcagtt tcctgcattg gaacctggag caagcgctct    9120
atctttcaca caaattccct cacctgagat tgaggtgctc ttgttactgg gtgtctgtgt   9180
```

```
gctgtaattc tggttttgga tatgttctgt aaagattttg acaaatgaaa atgtgttttt      9240
ctctgttaaa acttgtcaga gtactagaag ttgtatctct gtaggtgcag gtccatttct      9300
gcccacaggt agggtgtttt tctttgatta agagattgac acttctgttg cctaggacct      9360
cccaactcaa ccatttctag gtgaaggcag aaaaatccac attagttact cctcttcaga      9420
catttcagct gagataacaa atcttttgga attttttcac ccatagaaag agtggtagat      9480
atttgaattt agcaggtgga gtttcatagt aaaaacagct tttgactcag ctttgattta      9540
tcctcatttg atttggccag aaagtaggta atatgcattg attggcttct gattccaatt      9600
cagtatagca aggtgctagg ttttttcctt tccccacctg tctcttagcc tggggaatta      9660
aatgagaagc cttagaatgg gtggcccttg tgacctgaaa cacttcccac ataagctact      9720
taacaagatt gtcatggagc tgcagattcc attgcccacc aaagactaga acacacacat      9780
atccatacac caaaggaaag acaattctga aatgctgttt ctctggtggt tccctctctg      9840
gctgctgcct cacagtatgg gaacctgtac tctgcagagg tgacaggcca gatttgcatt      9900
atctcacaac cttagccctt ggtgctaact gtcctacagt gaagtgcctg ggggttgtc       9960
ctatcccata agccacttgg atgctgacag cagccaccat cagaatgacc cacgcaaaaa      10020
aaagaaaaaa aaaattaaaa agtcccctca caacccagtg acacctttct gctttcctct      10080
agactggaac attgattagg gagtgcctca gacatgacat tcttgtgctg tccttggaat      10140
taatctggca gcaggaggga gcagactatg taaacagaga taaaaattaa ttttcaatat      10200
tgaaggaaaa aagaaataag aagagagaga gaaagaaagc atcacacaaa gatttcctta      10260
aaagaaacaa ttttgcttga aatctcttta gatggggctc atttctcacg gtggcacttg      10320
gcctccactg ggcagcagga ccagctccaa gcgctagtgt tctgttctct ttttgtaatc      10380
ttggaatctt ttgttgctct aaatacaatt aaaaatggca gaaacttgtt tgttggacta      10440
catgtgtgac tttgggtctg tctctgcctc tgctttcaga aatgtcatcc attgtgtaaa      10500
atattggctt actggtctgc cagctaaaac ttggccacat cccctgttat ggctgcagga      10560
tcgagttatt gttaacaaag agacccaaga aaagctgcta atgtcctctt atcattgttg      10620
ttaatttgtt aaaacataaa gaaatctaaa atttcaaaaa a                          10661

<210> SEQ ID NO 50
<211> LENGTH: 2060
<212> TYPE: DNA
<213> ORGANISM: Homo sapiens

<400> SEQUENCE: 50
acctgggtcg ggtgcagact gcggagcggg ccctaccgtg tgcgcagaaa gaggaggcgc        60
ttgccttcag cttgtgggaa atcccgaaga tggccaaaga caactcaact gttcgttgct       120
tccagggcct gctgattttt ggaaatgtga ttattggttg ttgcggcatt gccctgactg       180
cggagtgcat cttctttgta tctgaccaac acagcctcta cccactgctt gaagccaccg       240
acaacgatga catctatggg gctgcctgga tcggcatatt tgtgggcatc tgcctcttct       300
gcctgtctgt tctaggcatt gtaggcatca tgaagtccag caggaaaatt cttctggcgt       360
atttcattct gatgtttata gtatatgcct ttgaagtggc atcttgtatc acagcagcaa       420
cacaacaaga ctttttcaca cccaacctct tcctgaagca gatgctagag aggtaccaaa       480
acaacagccc tccaaacaat gatgaccagt ggaaaaacaa tggagtcacc aaaacctggg       540
acaggctcat gctccaggac aattgctgtg gcgtaaatgg tccatcagac tggcaaaaat       600
acacatctgc cttccggact gagaataatg atgctgacta tccctggcct cgtcaatgct       660
```

-continued

```
gtgttatgaa caatcttaaa gaacctctca acctggaggc ttgtaaacta ggcgtgcctg    720
gtttttatca caatcagggc tgctatgaac tgatctctgg tccaatgaac cgacacgcct    780
ggggggttgc ctggtttgga tttgccattc tctgctggac tttttgggtt ctcctgggta    840
ccatgttcta ctggagcaga attgaatatt aagcataaag tgttgccacc atacctcctt    900
ccccgagtga ctctggattt ggtgctggaa ccagctctct cctaatattc cacgtttgtg    960
ccccacacta acgtgtgtgt cttacattgc caagtcagat ggtacggact tcctttagga   1020
tctcaggctt ctgcagttct catgactcct acttttcatc ctagtctagc attctgcaac   1080
atttatatag actgttgaaa ggagaatttg aaaaatgcat aataactact tccatccctg   1140
cttattttta atttgggaaa ataaatacat tcgaaggaac ctgtgttatc acagtaaccc   1200
agagctgtat ttggctagca atctgcctgt atctctcact attatctaaa agaaaccttc   1260
caatgcttct gttgatctca gtattgtcag gggaacagag aagttgggaa aagattactg   1320
aaatatacct tttgcatttc tttctagagt agctcccata tatggagatg ggtgattctc   1380
ttgatgccac cttcagatcc ttttattctc cagaataatt cttaacagtg gttcaaattt   1440
cctttcatac cttgaagtat gtgtttagta gcctcaattc tccattaatt aaaagtgtgg   1500
gctgggcgtg gggctcatg cctgtaatcc cagcactttg ggaggccgag gtgggcagat   1560
cacctgaggt caggagttca agaccagcct ggccaacatg gtgaaacccc gtctctacaa   1620
aaatacaaaa attagccagg cgtgatggca ggtgcctgta atcctagcta cttggcaggc   1680
taacgcagga gaatcacttg accgggagac agaggttgca gtgagctgag atcgtaccta   1740
ttgcactcca tcctggatga aagagccaga ctctgtctca aacaaacaaa aaaagcgtgg   1800
ggacttctgg ggacagacaa ggtgcctgtt atatatttac tcagtctttg ccctgaatgg   1860
tctcagcttg agaccatttc aaactggaga gaagcaagcc agccaataga atggggtgat   1920
ttacagggat ttctgtttac tgtcaaaata tttctcatct gcactatgtt tccatttgtg   1980
gtcctgaagg aaattcttat aactcaacat ttgtctggtc ttataagtaa agacagcttt   2040
aaaatctgtt cactttcaaa                                               2060
```

```
<210> SEQ ID NO 51
<211> LENGTH: 23
<212> TYPE: DNA
<213> ORGANISM: Artificial sequence
<220> FEATURE:
<223> OTHER INFORMATION: Snythetic

<400> SEQUENCE: 51
cggactgaga ataatgatgc tga                                             23

<210> SEQ ID NO 52
<211> LENGTH: 21
<212> TYPE: DNA
<213> ORGANISM: Artificial sequence
<220> FEATURE:
<223> OTHER INFORMATION: Snythetic

<400> SEQUENCE: 52
gatcagttca tagcagccct g                                               21

<210> SEQ ID NO 53
<211> LENGTH: 27
<212> TYPE: DNA
<213> ORGANISM: Artificial sequence
<220> FEATURE:
```

<223> OTHER INFORMATION: Snythetic

<400> SEQUENCE: 53
tctcaacctg gaggcttgta aactagg        27

<210> SEQ ID NO 54
<211> LENGTH: 19
<212> TYPE: DNA
<213> ORGANISM: Artificial sequence
<220> FEATURE:
<223> OTHER INFORMATION: Snythetic

<400> SEQUENCE: 54
ggactccgtg cagcctatt        19

<210> SEQ ID NO 55
<211> LENGTH: 21
<212> TYPE: DNA
<213> ORGANISM: Artificial sequence
<220> FEATURE:
<223> OTHER INFORMATION: Snythetic

<400> SEQUENCE: 55
agaaaggatc ttgggcactt g        21

<210> SEQ ID NO 56
<211> LENGTH: 30
<212> TYPE: DNA
<213> ORGANISM: Artificial sequence
<220> FEATURE:
<223> OTHER INFORMATION: Snythetic

<400> SEQUENCE: 56
tcagttcact tttgacctgc taatcaagtc        30

<210> SEQ ID NO 57
<211> LENGTH: 8112
<212> TYPE: DNA
<213> ORGANISM: Homo sapiens

<400> SEQUENCE: 57

| | | | | | |
|---|---|---|---|---|---|
| gctgcgagca | gagagggatt | cctcggaggt | catctgttcc | atcttcttgc | ctatgcaaat | 60 |
| gcctgcctga | agctgctgga | ggctggcttt | gtaccggact | ttgtacaggg | aaccagggaa | 120 |
| acgaatgcag | agtgctcctg | acattgcctg | tcactttttc | ccatgatact | ctggcttcac | 180 |
| agtttggaga | ctgccaggga | ccatgttttg | cccattgact | attactttcc | accccagaag | 240 |
| acctgcctga | tctgtggaga | tgaagcttct | gggtgtcact | atggagctct | cacatgtgga | 300 |
| agctgcaagg | tcttcttcaa | aagagccgct | gaagggaaac | agaagtacct | gtgcgccagc | 360 |
| agaaatgatt | gcactattga | taaattccga | aggaaaaatt | gtccatcttg | tcgtcttcgg | 420 |
| aaatgttatg | aagcagggat | gactctggga | gcccggaagc | tgaagaaact | tggtaatctg | 480 |
| aaactacagg | aggaaggaga | ggcttccagc | accaccagcc | ccactgagga | gacaacccag | 540 |
| aagctgacag | tgtcacacat | tgaaggctat | gaatgtcagc | ccatctttct | gaatgtcctg | 600 |
| gaagccattg | agccaggtgt | agtgtgtgct | ggacacgaca | acaaccagcc | cgactccttt | 660 |
| gcagccttgc | tctctagcct | caatgaactg | ggagagagac | agcttgtaca | cgtggtcaag | 720 |
| tgggccaagg | ccttgcctgg | cttccgcaac | ttacacgtgg | acgaccagat | ggctgtcatt | 780 |
| cagtactcct | ggatggggct | catggtgttt | gccatgggct | ggcgatcctt | caccaatgtc | 840 |
| aactccagga | tgctctactt | cgcccctgat | ctggttttca | atgagtaccg | catgcacaag | 900 |

```
tcccggatgt acagccagtg tgtccgaatg aggcacctct ctcaagagtt tggatggctc    960
caaatcaccc cccaggaatt cctgtgcatg aaagcactgc tactcttcag cattattcca   1020
gtggatgggc tgaaaaatca aaaattcttt gatgaacttc gaatgaacta catcaaggaa   1080
ctcgatcgta tcattgcatg caaaagaaaa atcccacat cctgctcaag acgcttctac    1140
cagctcacca agctcctgga ctccgtgcag cctattgcga gagagctgca tcagttcact   1200
tttgacctgc taatcaagtc acacatggtg agcgtggact ttccggaaat gatggcagag   1260
atcatctctg tgcaagtgcc caagatcctt tctgggaaag tcaagcccat ctatttccac   1320
acccagtgaa gcattggaaa ccctatttcc ccaccccagc tcatgccccc tttcagatgt   1380
cttctgcctg ttataactct gcactactcc tctgcagtgc cttggggaat tcctctatt    1440 gatgtacagt ctgtcatgaa catgttcctg aattctattt gctgggcttt tttttctct    1500 ttctctcctt tcttttttctt cttccctccc tatctaaccc tcccatggca ccttcagact   1560
ttgcttccca ttgtggctcc tatctgtgtt ttgaatggtg ttgtatgcct ttaaatctgt   1620
gatgatcctc atatggccca gtgtcaagtt gtgcttgttt acagcactac tctgtgccag   1680
ccacacaaac gtttacttat cttatgccac gggaagttta gagagctaag attatctggg   1740
gaaatcaaaa caaaacaag caaacaaaaa aaaaagcaa aacaaaaca aaaataagc       1800 caaaaaacct tgctagtgtt ttttcctcaa aaataaataa ataaataaat aaatacgtac   1860
atacatacac acatacatac aaacatatag aaatccccaa agaggccaat agtgacgaga   1920
aggtgaaaat tgcaggccca tggggagtta ctgatttttt catctcctcc ctccacggga   1980
gactttattt tctgccaatg ctattgcca ttagagggca gagtgacccc agagctgagt    2040
tgggcagggg ggtggacaga gaggagagga caaggagggc aatggagcat cagtacctgc   2100
ccacagcctt ggtccctggg ggctagactg ctcaactgtg gagcaattca ttatactgaa   2160
aatgtgcttg ttgttgaaaa tttgtctgca tgttaatgcc tcaccccaa accctttct    2220 ctctcactct ctgcctccaa cttcagattg actttcaata gtttttctaa gacctttgaa   2280
ctgaatgttc tcttcagcca aaacttggcg acttccacag aaaagtctga ccactgagaa   2340
gaaggagagc agagatttaa ccctttgtaa ggccccattt ggatccaggt ctgctttctc   2400
atgtgtgagt cagggaggag ctggagccag aggagaagaa aatgatagct tggctgttct   2460
cctgcttagg acactgactg aatagttaaa ctctcactgc cactacccttt tccccacctt   2520 taaaagacct gaatgaagtt ttctgccaaa ctccgtgaag ccacaagcac cttatgtcct   2580
cccttcagtg ttttgtgggc ctgaatttca tcacactgca tttcagccat ggtcatcaag   2640
cctgtttgct tcttttgggc atgttcacag attctctgtt aagagccccc accaccaaga   2700
aggttagcag gccaacagct ctgacatcta tctgtagatg ccagtagtca caaagatttc   2760
ttaccaactc tcagatcgct ggagccctta dacaaactgg aaagaaggca tcaaagggat   2820
caggcaagct gggcgtcttg cccttgtccc cagagatga taccctccca gcaagtggag   2880
aagttctcac ttccttcttt agagcagcta aagggctac ccagatcagg gttgaagaga    2940
aaactcaatt accagggtgg gaagaatgaa ggcactagaa ccagaaaccc tgcaaatgct   3000
cttcttgtca cccagcatat ccacctgcag aagtcatgag aagagagaag gaacaaagag   3060
gagactctga ctactgaatt aaaatcttca gcggcaaagc ctaaagccag atggacacca   3120
tctggtgagt ttactcatca tcctcctctg ctgctgattc tgggctctga cattgcccat   3180
actcactcag attccccacc tttgttgctg cctcttagtc agagggaggc caaaccattg   3240
```

```
agactttcta cagaaccatg gcttctttcg gaaaggtctg gttggtgtgg ctccaatact   3300
ttgccaccca tgaactcagg gtgtgccctg ggacactggt tttatatagt cttttggcac   3360
acctgtgttc tgttgacttc gttcttcaag cccaagtgca agggaaaatg tccacctact   3420
ttctcatctt ggcctctgcc tccttactta gctcttaatc tcatctgttg aactcaagaa   3480
atcaagggcc agtcatcaag ctgcccattt taattgattc actctgtttg ttgagaggat   3540
agtttctgag tgacatgata tgatccacaa gggtttcctt ccctgatttc tgcattgata   3600
ttaatagcca aacgaacttc aaaacagctt taaataacaa gggagagggg aacctaagat   3660
gagtaatatg ccaatccaag actgctggag aaaactaaag ctgacaggtt ccctttttgg   3720
ggtgggatag acatgttctg gttttcttta ttattacaca atctggctca tgtacaggat   3780
cacttttagc tgttttaaac agaaaaaaat atccaccact cttttcagtt acactaggtt   3840
acattttaat aggtccttta catctgtttt ggaatgattt tcatcttttg tgatacacag   3900
attgaattat atcattttca tatctctcct tgtaaatact agaagctctc ctttacattt   3960
ctctatcaaa ttttcatct ttatgggttt cccaattgtg actcttgtct tcatgaatat   4020
atgttttca tttgcaaaag ccaaaaatca gtgaaacagc agtgtaatta aaagcaacaa   4080
ctggattact ccaaatttcc aaatgacaaa actagggaaa aatagcctac aaagcctttt   4140
aggcctactc tttctgtgct tgggtttgag tgaacaaagg agattttagc ttggctctgt   4200
tctcccatgg atgaaggag gaggattttt ttttctttt ggccattgat gttctagcca   4260
atgtaattga cagaagtctc attttgcatg cgctctgctc tacaaacaga gttggtatgg   4320
ttggtatact gtactcacct gtgagggact ggccactcag acccacttag ctggtgagct   4380
agaagatgag gatcactcac tggaaaagtc acaaggacca tctccaaaca agttggcagt   4440
gctcgatgtg gacgaagagt gaggaagaga aaagaagga gcaccaggga gaaggctccg   4500
tctgtgctgg gcagcagaca gctgccagga tcacgaactc tgtagtcaaa gaaaagagtc   4560
gtgtggcagt ttcagctctc gttcattggg cagctcgcct aggcccagcc tctgagctga   4620
catgggagtt gttggattct ttgtttcata gctttttcta tgccataggc aatattgttg   4680
ttcttggaaa gttatttatt ttttaactc ccttactctg agaaagggat attttgaagg   4740
actgtcatat atctttgaaa aagaaaaatc tgtaatacat atatttttat gtatgttcac   4800
tggcactaaa aaatatagag agcttcattc tgtcctttgg gtagttgctg aggtaattgt   4860
ccaggttgaa aaataatgtg ctgatgctag agtccctctc tgtccatact ctacttctaa   4920
atacatatag gcatacatag caagtttat ttgacttgta cttaagaga aaatatgtcc   4980
accatccaca tgatgcacaa atgagctaac attgagcttc aagtagcttc taagtgtttg   5040
tttcattagg cacagcacag atgtggcctt tcccccttc tctcccttga tatctggcag   5100
ggcataaagg cccaggccac ttcctctgcc ccttcccagc cctgcaccaa agctgcattt   5160
caggagactc tctccagaca gcccagtaac tacccgagca tggcccctgc atagccctgg   5220
aaaaataaga ggctgactgt ctacgaatta tcttgtgcca gttgcccagg tgagagggca   5280
ctgggccaag ggagtggttt tcatgtttga cccactacaa ggggtcatgg gaatcaggaa   5340
tgccaaagca ccagatcaaa tccaaaactt aaagtcaaaa taagccattc agcatgttca   5400
gtttcttgga aaaggaagtt tctacccctg atgcctttgt aggcagatct gttctcacca   5460
ttaatctttt tgaaaatctt ttaaagcagt ttttaaaaag agagatgaaa gcatcacatt   5520
atataaccaa agattacatt gtacctgcta agataccaaa attcataagg gcagggggg   5580
agcaagcatt agtgcctctt tgataagctg tccaaagaca gactaaagga ctctgctggt   5640
```

```
gactgactta taagagcttt gtgggttttt ttttccctaa taatatacat gtttagaaga    5700
attgaaaata atttcgggaa aatgggatta tgggtccttc actaagtgat tttataagca    5760
gaactggctt tccttttctc tagtagttgc tgagcaaatt gttgaagctc catcattgca    5820
tggttggaaa tggagctgtt cttagccact gtgtttgcta gtgcccatgt tagcttatct    5880
gaagatgtga aacccttgct gataagggag catttaaagt actagatttt gcactagagg    5940
gacagcaggc agaaatcctt atttctgccc actttggatg cacaaaaag ttatctgcag     6000 ttgaaggcag aaagttgaaa tacattgtaa atgaatattt gtatccatgt ttcaaaattg    6060
aaatatatat atatatatat atatatatat atatatatat atagtgtgtg tgtgtgttct    6120
gatagcttta actttctctg catctttata tttggttcca gatcacacct gatgccatgt    6180
acttgtgaga gaggatgcag ttttgttttg gaagctctct cagaacaaac aagacacctg    6240
gattgatcag ttaactaaaa gttttctccc ctattgggtt tgacccacag gtcctgtgaa    6300
ggagcagagg gataaaaaga gtagaggaca tgatacattg tactttacta gttcaagaca    6360
gatgaatgtg gaaagcataa aaactcaatg gaactgactg agatttacca cagggaaggc    6420
ccaaacttgg ggccaaaagc ctacccaagt gattgaccag tggcccccta atgggacctg    6480
agctgttgga agaagagaac tgttccttgg tcttcaccat ccttgtgaga aagggcagt    6540 ttcctgcatt ggaacctgga gcaagcgctc tatctttcac acaaattccc tcacctgaga    6600
ttgaggtgct cttgttactg ggtgtctgtg tgctgtaatt ctggttttgg atatgttctg    6660
taaagatttt gacaaatgaa aatgtgtttt tctctgttaa aacttgtcag agtactagaa    6720
gttgtatctc tgtaggtgca ggtccatttc tgcccacagg tagggtgttt ttctttgatt    6780
aagagattga cacttctgtt gcctaggacc tcccaactca accatttcta ggtgaaggca    6840
gaaaaatcca cattagttac tcctcttcag acatttcagc tgagataaca aatcttttgg    6900
aattttttca cccatagaaa gagtggtaga tatttgaatt tagcaggtgg agtttcatag    6960
taaaaacagc ttttgactca gctttgattt atcctcattt gatttggcca gaaagtaggt    7020
aatatgcatt gattggcttc tgattccaat tcagtatagc aaggtgctag gttttttcct    7080
ttccccacct gtctcttagc ctggggaatt aaatgagaag ccttagaatg ggtggccctt    7140
gtgacctgaa acacttccca cataagctac ttaacaagat tgtcatggag ctgcagattc    7200
cattgcccac caaagactag aacacacaca tatccataca ccaaaggaaa gacaattctg    7260
aaatgctgtt tctctggtgg ttccctctct ggctgctgcc tcacagtatg gaacctgta    7320 ctctgcagag gtgacaggcc agatttgcat tatctcacaa ccttagccct tggtgctaac    7380
tgtcctacag tgaagtgcct gggggttgt cctatcccat aagccacttg gatgctgaca    7440
gcagccacca tcagaatgac ccacgcaaaa aaagaaaaa aaaattaaa aagtcccctc     7500 acaacccagt gacacctttc tgctttcctc tagactggaa cattgattag ggagtgcctc    7560
agacatgaca ttcttgtgct gtccttggaa ttaatctggc agcaggaggg agcagactat    7620
gtaaacagag ataaaaatta attttcaata ttgaaggaaa aagaaataa gaagagagag     7680 agaaagaaag catcacacaa agattttctt aaaagaaaca attttgcttg aaatctcttt    7740
agatggggct catttctcac ggtggcactt ggcctccact gggcagcagg accagctcca    7800
agcgctagtg ttctgttctc ttttgtaat cttggaatct tttgttgctc taaatacaat     7860 taaaatggc agaaacttgt tgttggact acatgtgtga ctttgggtct gtctctgcct      7920
ctgctttcag aaatgtcatc cattgtgtaa aatattggct tactggtctg ccagctaaaa    7980
```

```
cttggccaca tcccctgtta tggctgcagg atcgagttat tgttaacaaa gagacccaag    8040
aaaagctgct aatgtcctct tatcattgtt gttaatttgt taaaacataa agaaatctaa    8100
aatttcaaaa aa                                                        8112
```